United States Patent [19]

Moreno et al.

[11] 4,333,475

[45] Jun. 8, 1982

[54] AMBULATORY CARDIAC MONITORING SYSTEM

[75] Inventors: John R. Moreno, Cherry Hill, N.J.; Richard J. Byrne; Charles B. Shakespeare, both of Philadelphia, Pa.

[73] Assignee: Medical Concepts, Inc., Mount Laurel, N.J.

[21] Appl. No.: 100,903

[22] Filed: Dec. 6, 1979

[51] Int. Cl.³ .............................................. A61B 5/04
[52] U.S. Cl. ................................................... 128/711
[58] Field of Search ............... 128/696, 710, 711, 901, 128/902, 702, 703, 704

[56] References Cited

U.S. PATENT DOCUMENTS

| | | | |
|---|---|---|---|
| 3,611,164 | 10/1971 | Day | 128/704 |
| 3,651,280 | 3/1972 | Streckmann | 128/711 |
| 3,699,948 | 10/1972 | Ota et al. | 128/710 |
| 3,903,874 | 9/1975 | Shakespeare | 128/901 |
| 4,023,564 | 5/1977 | Valiquette et al. | 128/704 |
| 4,090,505 | 5/1978 | Mortara | 128/710 |
| 4,183,354 | 1/1980 | Sibley et al. | 128/711 |

OTHER PUBLICATIONS

Simmons, "3rd Annual Symposium on Computer Applications in Medicine", Washington, D.C., Oct. 14-17, 1979, pp. 448-449.

Ruiz et al., "Proceedings of an International Symposium", Toulouse, France, Mar. 22-25, 1977, pp. 117-127.

Antila et al., "Proceedings of the 1st National Meeting on Biophysics and Biotechnology in Finland", Helsinki, Jan. 4-5, 1973, pp. 162-164.

*Primary Examiner*—William E. Kamm
*Attorney, Agent, or Firm*—Maleson, Rosenberg & Bilker

[57] ABSTRACT

An ambulatory cardiac monitoring system (10) to event record and monitor ECG signals (20) from a patient (12) for a predetermined time interval. The ambulatory cardiac monitoring system (10) includes a recorder system (18) which is carried by the patient (12). The recorder system (10) is coupled to the patient through leads (16) and electrodes (14) positionally located contiguous to the patient (12). The recorder system (18) includes an analog pre-processor (32), a first microcomputer (34) coupled in a feedback manner to analog pre-processor (32), and a cassette recorder (38). The analog pre-processor (32) has incorporated both automatic gain control and conditioning circuitry that normalizes and filters the basic ECG signal (20). The analog pre-processor (32) produces a plurality of extraction signals which are input to microcomputer (34). The microcomputer (34) continuously monitors the signal inputs from the analog pre-processor (32) as well as digitized ECG signal (20) from an analog/digital converter (36). The microcomputer (34) includes decision algorithms for classification of each heartbeat and tallies abnormal events. The memory of microcomputer (34) is used as a temporary storage area of the ECG signal (20) in order to delay the ECG signal (20) for a predetermined time interval in order that analysis of a particular signal may be obtained.

48 Claims, 22 Drawing Figures

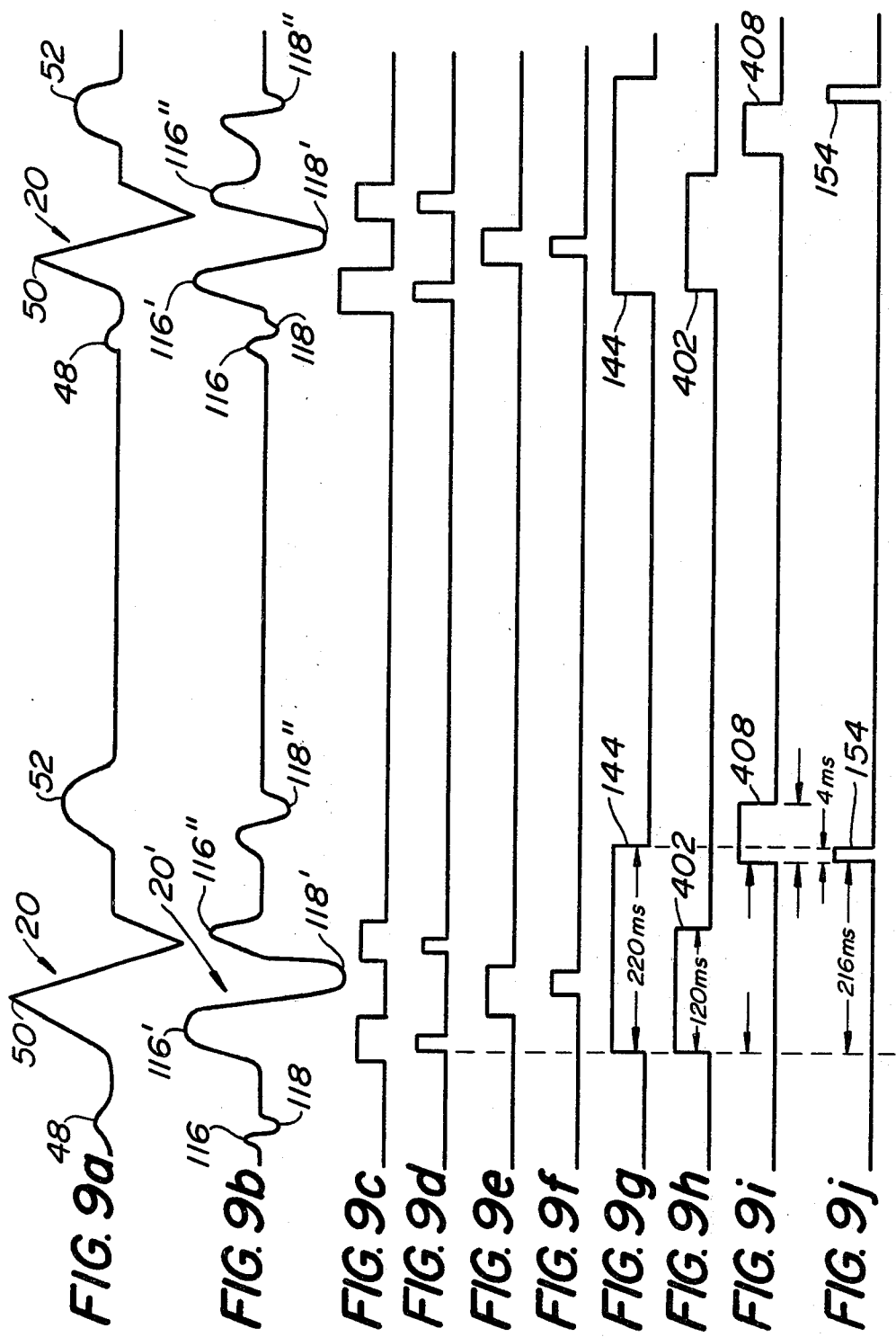

AMBULATORY CARDIAC MONITORING SYSTEM

BACKGROUND OF THE INVENTION

1. Field of the Invention

This invention pertains to cardiac monitoring systems. In particular, this invention relates to ambulatory cardiac monitoring systems where a patient is monitored for a predetermined interval. More in particular, this invention relates to an ambulatory cardiac monitoring system where the patient carries a recorder system and the recorder system is coupled to the patient for continuous monitoring of ECG signals.

Still further, this invention relates to an ambulatory cardiac monitoring system where abnormal ECG signals are recorded on a mini-cassette carried within the recorder system. Further, this invention relates to an ambulatory cardiac monitoring system where the cassette is removed from the recording system after the predetermined time interval and inserted into a scanner system remote from the patient for production of both a trend report and an ECG strip for diagnostic purposes.

More in particular, this invention pertains to an ambulatory cardiac monitoring system where the recorder carried by the patient includes both an analog pre-processor and a first microcomputer which is coupled in feedback relation to the analog pre-processor. Still further, this invention relates to an ambulatory cardiac monitoring system having a recorder system which delays the ECG signal passing from the patient in order to provide a time frame interval within which a particular ECG signal may be analyzed and determinations made of various heart arrhythmias and abnormal events based on a particular patient's ECG signal output.

2. Prior Art

Systems for monitoring and analyzing ECG signals are well-known in the art. In general, there are four types of cardiograms being utilized, i.e., resting cardiograms, stress cardiograms, echo cardiograms, and ambulatory cardiograms. Resting cardiograms systems generally take a sample of an ECG signal over a short period of time in a non-ambulatory environment. Thus, heart arrhythmias which may be chronic or transient, are only displayed in the resting cardiograms when they are chronic. If the heart arrhythmias are transient, there is a low probability that resting cardiogram systems will describe such due to the short time interval period within which they are taken.

Ambulatory electro-cardiogram systems to monitor both the chronic and transient heart arrhythmias are carried by the patient during the performance of his or her activities throughout a predetermined time interval. In some prior art ambulatory electrocardiogram systems, the patient's heartbeat signals are recorded continuously for a predetermined time interval on a portable tape recorder carried by the patient. Subsequent to the recording time interval, a scanning device is used that plays back the tape at an accelerated speed. A technically trained operator monitors an oscilloscope and a tone produced by the scanner to observe and/or monitor any heart arrhythmias. In such prior systems the analysis is highly subjective dependent on the skill of the operator.

Additionally, in such prior art systems, the continuous monitoring of the heartbeat of the patient produces a stream of unwanted data and utilizes expensive scanner system equipment in cooperation with highly skilled technicians for diagnosis of the ECG. Some such prior art systems do not analyze the heart arrhythmias to the quantitative extent of the subject ambulatory cardiac monitoring system, which thus results in some arrhythmias going unnoticed with possible deleterious results.

Ambulatory monitoring devices are generally divided into two categories, the first category being Holter monitoring and the second category being commonly referred to as Event recording. In prior art Holter monitoring devices, the patient is monitored continuously for a predetermined time interval with the subsequent disadvantages as has been previously described.

In Event recording, the system is carried by the patient and includes systems for arrhythmia detection and such is condensed to provide salient events of the arrhythmia. In some prior Event recording systems, chronological logs are not provided to permit a quantitating capability, as is provided in the subject system. In other prior art Event recorders, detected arrhythmias are recorded once each predetermined time interval so that when the system records a specific arrhythmia, the system does not analyze any further incidents of the specific arrhythmia for the predetermined time interval and such is incapable of quantifying data. Thus, in some prior art systems of this type, important arrhythmia data is lost to the diagnostician.

Other prior art Event recording systems do not normalize output signals as a function of a particular patient being monitored. Thus, in such prior art Event recording systems, unwanted data may be taken into account based on a false signal that an arrhythmia has occurred when in fact, that signal is normal when related to that particular patient being monitored.

BRIEF DESCRIPTION OF THE DRAWINGS

FIGS. 9(a)-(j) is a timing diagram presenting a graphical representation of the ECG signal and the differentiated ECG signals for actuating signals within the ambulatory cardiac monitoring system.

DESCRIPTION OF THE PREFERRED EMBODIMENTS

Figure 1:
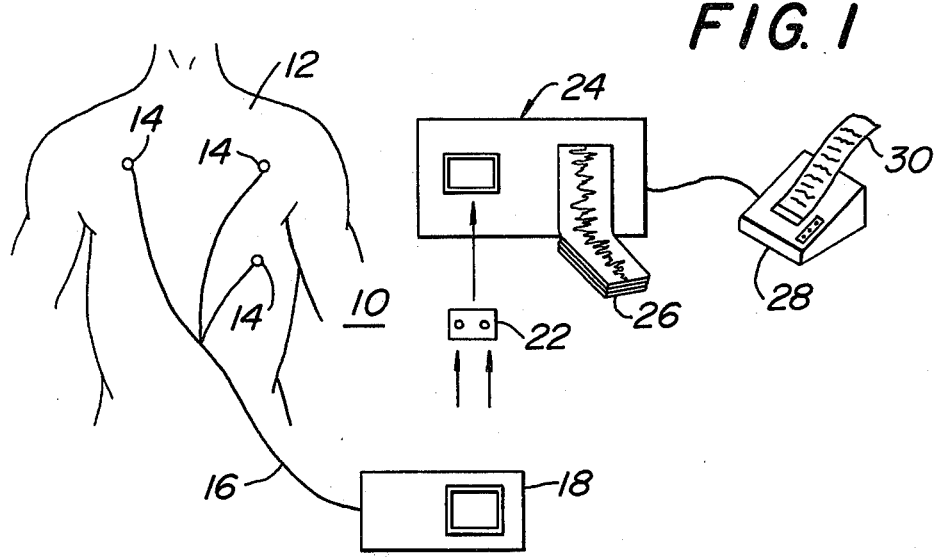
FIG. 1 is a flow diagram of the ambulatory cardiac monitoring system, showing the recorder system coupled to the patient, as well as the scanner system for generating both ECG strip booklets and trend reports.

Referring now to FIG. 1, there is shown an overall system flow representation of ambulatory cardiac monitoring system 10 to provide an information flow report based on ECG signals 20 being issued from patient or user 12. In overall concept, ambulatory cardiac monitoring system 10 continuously monitors, classifies, and quantizes predetermined portions of ECG signals 20 from patient 12. Abnormal portions of ECG signals 20 are classified as to the pattern abnormality and real time of occurrence. Abnormal or significant signals are printed on ECG strips 26 and quantified information is printed in ECG report 30 at the conclusion of a predetermined monitoring period.

During the time interval monitoring period, patient 12 is continuously monitored for ECG signals 20 in an ambulatory manner. A detailed record of abnormal ECG signals 20 is written on a storage mechanism such as cassette tape 22, as will be detailed in following paragraphs. Subsequent to the monitoring period, cassette tape 22 is removed from the portion of cardiac monitoring system 10 carried by patient 12 and is inserted into report generation system 24 wherein ECG strips 26 and report 30 are printed out or otherwise detailed to a doctor or technician for diagnostic purposes.

Thus, in general, ambulatory cardiac monitoring system 10 is provided to event record and monitor ECG signals 20 from patient 12 for a predetermined time interval on recording medium 22. Recording medium 22 is subsequently removed from patient 12 after the predetermined time interval and is inserted into scanner or report generation system 24 for producing printed outputs of the events recorded on recording medium 22. Of significant importance to overall ambulatory cardiac monitoring system 10 is recorder system 18, which is releasably coupled to patient 12 during the predetermined time interval. Recorder system 18 is electrically coupled to patient 12 for (1) continuously monitoring ECG signals 20 of patient 12 during the predetermined time interval, and (2) entering a record signal on recording medium 22 responsive to prior ECG signals 20 monitored from patient 12 during the predetermined time interval.

During the monitoring period or predetermined time interval, recorder system 18 is carried by user or patient 12 and is adapted to continuously pick up ECG signals 20 from user or patient 12. The readings are entered into mini-cassette tape 22 during the monitoring period. Subsequent to the monitoring time interval period, cassette tape 22 is removed from recorder system 18 and is inserted into scanner system 24. Scanner system 24 generates ECG strips 26 and is further coupled to printer 28 which prints out report 30 based upon the information contained within cassette tape 22.

Report 30 issuing from printer 28 coupled to scanner system 24 is a printed chronological listing of arrhythmia events, heart rate, and ECG signal 20 quality. Entries are made for predetermined time intervals taken during the monitoring period. ECG strips 26 issuing from scanner system 24 are oscillographic recordings of significant events.

Particular information is chosen by first micro-computer 34 contained within recorder system 18. Although event recordings may be variably programmed, in general, events are chosen based on severity and repetition. Detected events of ventricular tachycardia, ventricular fibrillation, and dropped beats are recorded in conjunction with significant samples of premature ventricular contractions (PVC's), bigeminal PVC's, which are premature ventricular contractions alternating with normal beats, supra-ventricular tachycardia, supra ventricular, ectopic beats, and conditions of unstable rhythm where R-R intervals vary more than a predetermined amount from a median.

Figure 3A:
FIGS. 3(a)-(e) shows a graphical representation of the ECG signal, the differentiated ECG signal, the positive pulse of the differentiated and automatic gain controlled ECG signal, the positive pulse low threshold detect signal, and the positive pulse high threshold detect signal.

Referring now to FIGS. 3a and 9a, there is shown ECG signals 20 upon which ambulatory cardiac monitoring system 10 operates. For purposes of clarification in following paragraphs, ECG signals 20 for the purposes of the discussion and description of the inventive concepts, as is herein described, consists of QRS wave complex 50, P wave 48, and T wave form 52. For the purposes of this invention concept description, ECG signals 20 are thus composed of wave signals 48, 50 and 52.

One of the important invention concepts, as provided herein, is in the delineation of the particular wave form being monitored. Morphology measurements are only made during QRS wave complex 50 time intervals. Morphology of P wave 48, and T wave 50 are obviated, due to the fact that such has been found in prior art systems to provide confusing and inaccurate information from first micro-computer or micro-processor 34. Thus, determination of which complex 48, 50, and/or 52 is under consideration, is an important concept of the subject invention.

However, the aforementioned consideration of the determination of a particular type signal provides for an operating time domain where first micro-computer or micro-processor 34 is unable to provide the appropriate signal based upon real time signal wave input. Thus, morphology detectors are provided which utilize delayed ECG signals 20 initially normalized as will be discussed in following paragraphs.

Figure 2:
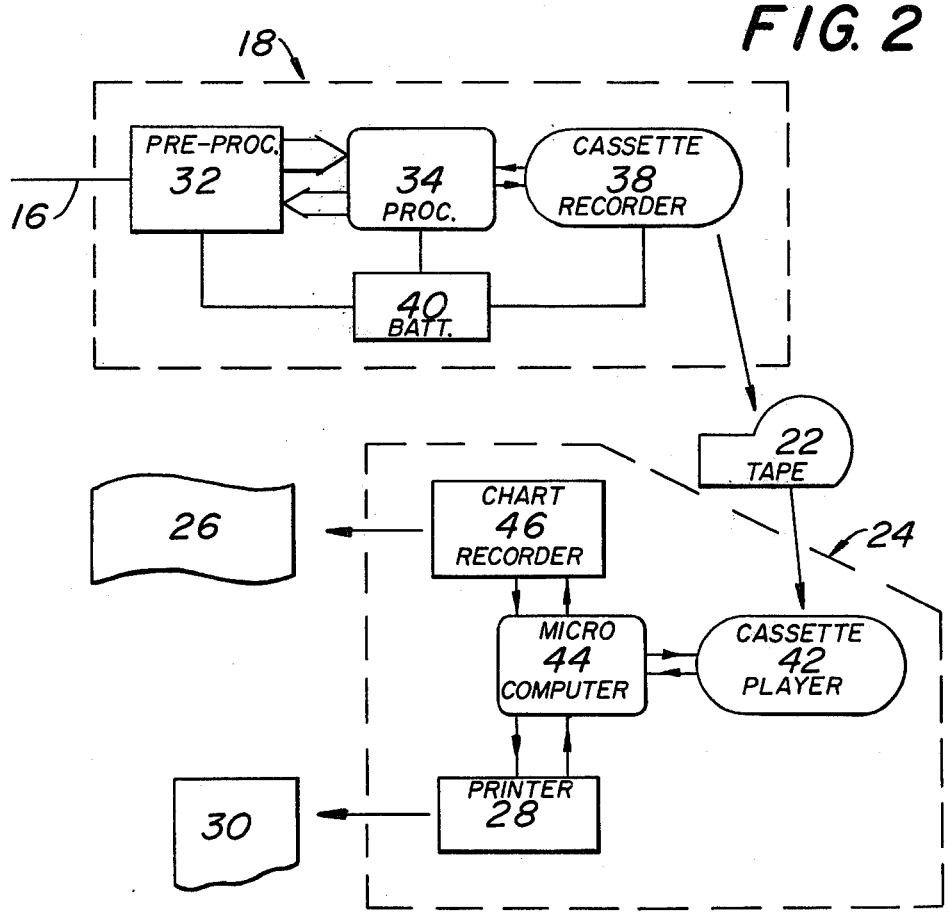
FIG. 2 is an overall block diagram of the ambulatory cardiac monitoring system.
Figure 4:
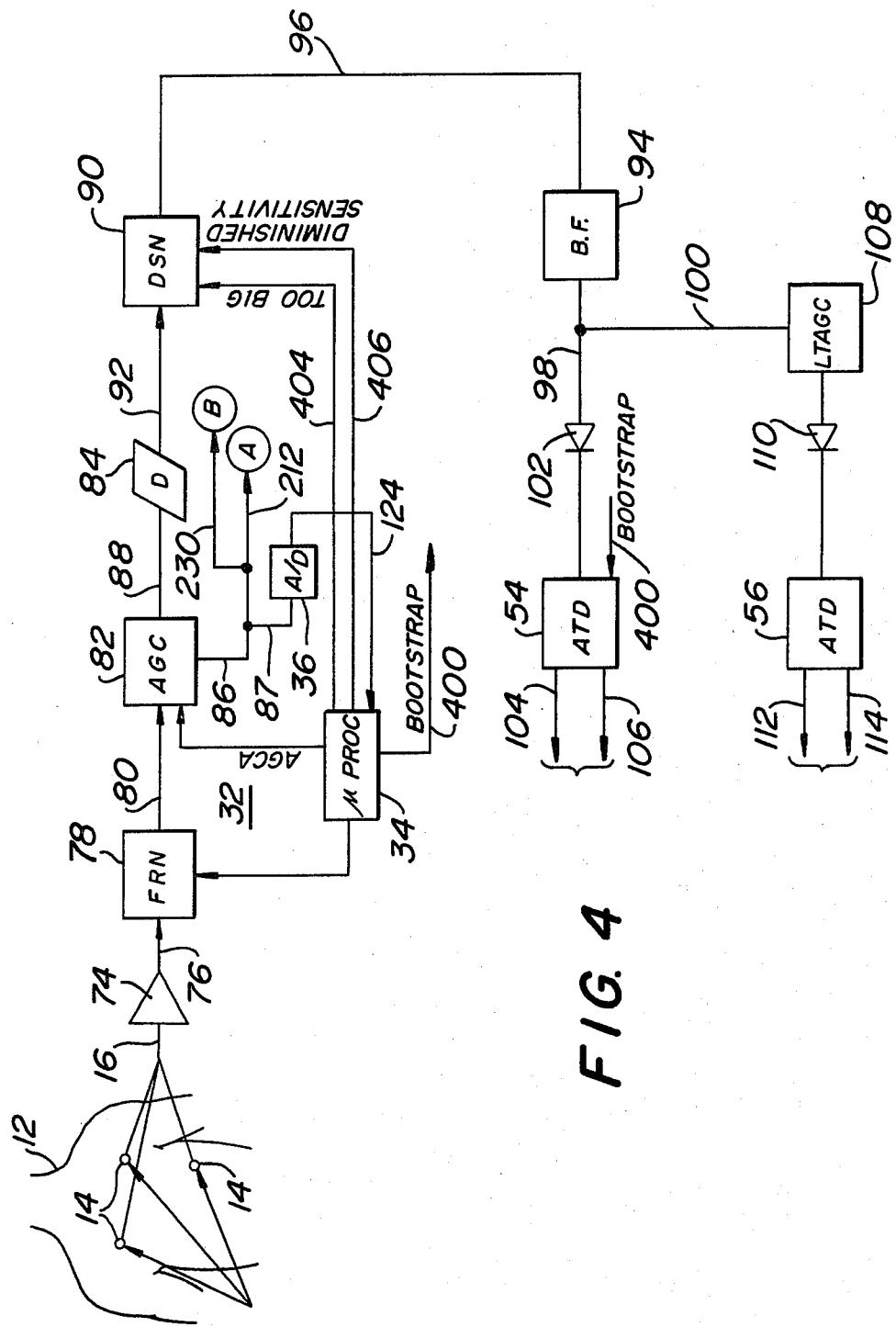
FIG. 4 is an electrical block diagram showing the analog pre-processor coupled to the patient.

In summary, the concept of delaying ECG signals 20 is important in the fact that where such signals 20 are not delayed, there is not sufficient time for pre-processor 32 to make appropriate measurements from the onset of QRS wave 50. The delay is thus required by pre-processor 32 which is measuring morphological features of QRS wave 50. As is evident, detection of QRS wave 50 is subsequent to the on-set which would cause a loss of information. Therefore a delayed signal is used in order that QRS wave 50 is detected before the on-set of the delayed QRS signal and total measurements may be made. Referring now to FIGS. 1, 2 and 4, it is seen that electrodes 14 are mounted on the body of user or patient 12 in the normal, well-known positional location adapted to read ECG signals 20. ECG signals 20 are input to portable recorder system 18 which is carried by patient or user 12 during the predetermined or ECG monitoring time interval.

Portable recorder system 18, to be described in following paragraphs, provides for analysis, classification, quantization of abnormal ECG signals 20, counting of abnormal beats, artifacts, and heart rate during the monitoring period or predetermined time interval. Cassette tape 22 is positionally located within portable recorder system 18 for producing a bulk memory of significant ECG signals 20 passing from the patient 12 on leads 16.

At the conclusion of the monitoring period, cassette tape 22 is removed from portable recording system 18, and is inserted into scanner or report generator 24. Report generator 24 may be located in a laboratory or a doctor's office, and the information contained on cassette tape 22 is read by scanner system 24 to produce trend report 30 on printer 38, as well as a detailed record of ECG signals on ECG strips 26.

Referring to the overall system block diagram shown and described in FIG. 2, recording system 18 includes analog pre-processor system 32 which provides for automatic gain control and various conditioning circuitry for normalization and filtering of ECG signals 20 passing from patient 12 on leads 16.

As will be seen in following paragraphs, analog pre-processor system 32 provides an output of twelve signals to act as input to first micro-computer 34. First micro-computer 34 is coupled in a feedback manner to analog pre-processor 32 for extracting significant ECG signals 20 and adapting them to a patient's particular ECG signal record.

Referring to FIG. 4, first micro-computer 34 is continuously utilized during the monitoring time interval for monitoring signal inputs from analog pre-processor 32, as well as digitized ECG signals 20 from analog to digital converter 36. First micro-computer 34 may be assembled from one of a number of standard micro-computer systems commercially available, such as RCA 1800 Cosmac Systems. First micro-computer 34 applies the signals to various decision algorithms for classification as to normal, abnormal, or artifact and analysis of each heart beat for an abnormal event. First micro-computer 34 is coupled to cassette recorder 38 (shown in FIG. 2), which is contained within portable recorder system 18.

Thus, ambulatory cardiac monitoring system 10, as is herein described, has recorder system 18 as the basis of the inventive concept, as herein detailed. Recorder system 18 in broad concept, includes analog pre-processor 32 which is electrically coupled to user or patient 12 for (1) normalization, (2) filtering, and (3) gain control of patient's ECG signals 20 to produce a plurality of pre-processor output signals. Additionally, recorder system 18 includes first micro-computer 34 which is connected to analog pre-processor 32 in a feedback coupling for producing record signals responsive to prior ECG signals 20 inserted to analog pre-processor 32 during the predetermined time interval.

Cassette recorder 38 may be one of a number of well-known commercially available recording systems and essentially provides a non-volatile bulk storage device for recorder system 18. Due to the fact that portable recorder system 18 is mounted on patient 12 throughout the monitoring time interval, battery pack 40 is utilized as an energy source, as is seen in FIG. 2. Battery pack system 40 is coupled to analog pre-processor 32, first micro-computer 34, and cassette recorder 38 in a normal electrical coupling mode for power source.

Cassette tape 22 is the linking or communication transport between portable recorder system 18 and scanner or report generation system 24. It is significant to note that the recording technique, as applied in the subject ambulatory cardiac monitoring system 10, is a digital recording system.

In this manner, tape speed errors and general noise is minimized in the final report being generated. Thus, any distortion or other errors found when analog recording techniques are utilized is brought to a minimum. Mini-cassette tape 22 is inserted into cassette player 42 contained within report generator 24. For optimization of time criteria restraints, cassette player 42, which may be one of a number of standard player systems commercially available, is actuated at a multiple of the record speed on cassette recorder 38 within recorder system 18.

Cassette player 42 is coupled to second micro-computer 44 contained within report generator system 24. Second micro-computer 44 essentially controls the automatic generation of ECG signals 20 to both ECG strips 26 and printer 28. Second micro-computer system 44 may also contain error diagnostic programs to provide for a checking of system 10 performance criteria. Micro-computer 44 is coupled to both printer 28, as well as to chart recorder 46 wherein strip chart recorder 46 provides a hard copy of the final ECG signals 20.

Referring now to FIG. 3a, it is seen that the overall ECG wave form 20 is composed of P signal 48, QRS wave complex 50, and T signal wave 52. Of paramount interest in ambulatory cardiac monitoring system 10 is the morphology and timing relationship of one QRS wave complex 50 to another. In many instances, the P wave 48 and T wave 52 causes anomalies in the analysis of QRS complex 50. Thus, system 10 circuitry is directed to ignore P wave form 48 and T wave form 52 through appropriate circuitry, as will be seen and described in following paragraphs.

Analog pre-processor 32, as shown in FIG. 4, is directed to detecting each QRS wave complex 50. In the QRS detection section shown in block FIG. 4, four signals are subsequently inserted into first micro-computer 34. A first set of signals is emitted from first adaptive threshold detector 54 on lines 104 and 106. The first set of signals includes a high threshold positive pulse (on line 104) and a low threshold positive pulse (on line 106).

A second set of signals emitted in the overall detection scheme are provided from second adaptive threshold detector 56 on lines 112 and 114. The second set of signals include the low threshold negative pulse (on line 114) and the high threshold negative pulse (on line 112).

Figure 5:
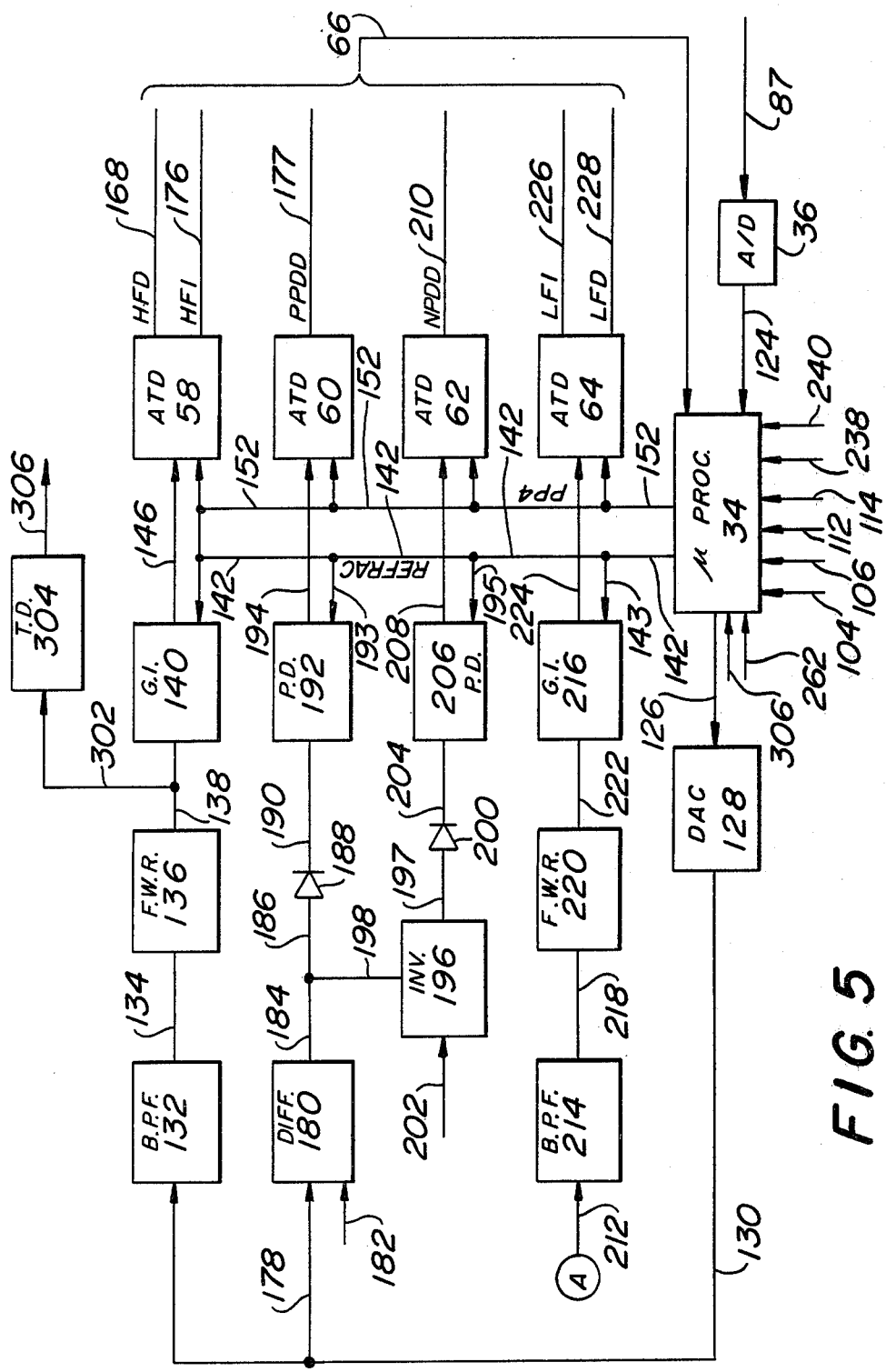
FIG. 5 is a block diagram showing a portion of the analog pre-processor in combination with a first microcomputer for morphology and temporal detection.

Each of the signals being emitted from first and second adaptive threshold detectors 54 and 56 are coupled to first micro-computer 34 and are inserted on the coupling lines 104, 106, 112 and 114, shown in FIG. 5. The decision of whether a particular series of pulses is being emitted from first adaptive threshold detector 54 and/or second adaptive threshold detector 56 is made within first micro-computer 34.

The second functional objective of analog pre-processor 32 in combination with micro-computer 34 is in the area of morphology detection, shown in FIG. 5. Analog pre-processor 32 and micro-computer 34 are in a closed loop feedback circuit each with respect to the other.

In general, analog pre-processor 32 extracts a predetermined number of features from ECG signal 20, and if there is a detection of a predetermined feature, such sends a signal to micro-processor 34. Micro-processor 34 receives the input from analog pre-processor 32 and decisions are made which are fed back into pre-processor 32 for the purposes of adapting analog pre-processor 32 to the particular user's signal. Thus, system 10 is adapted automatically to the patient's ECG signal 20 in order that there is obviated the need for switches or adjustment to set such up for a given patient 12, as has been found necessary in prior art systems.

In the area of morphology detection shown in block diagram 5, six signals are emitted from adaptive threshold detectors 58, 60, 62 and 64 within analog pre-processor 32. Output of adaptive threshold detector 58 is provided on lines 168 and 176, and are directed to a high frequency increase signal and a high frequency decrease signal, respectively.

Adaptive threshold detector 60 emits a positive peak differential decrease signal on line 177. A negative peak differential decrease signal is output from adaptive threshold detector 62 on line 210. Additionally, adaptive threshold detector 64 provides for a pair of signals being the low frequency increase signal and the low frequency decrease signal output from element 64 on lines 226 and 228, respectively.

Each of the signals emitted from respective adaptive threshold detectors 58, 60, 62 and 64 are fed back into first micro-computer 34 on a series of input lines, schematically represented for the purposes of clarity, as input line 66 into micro-computer 34.

Figure 6:
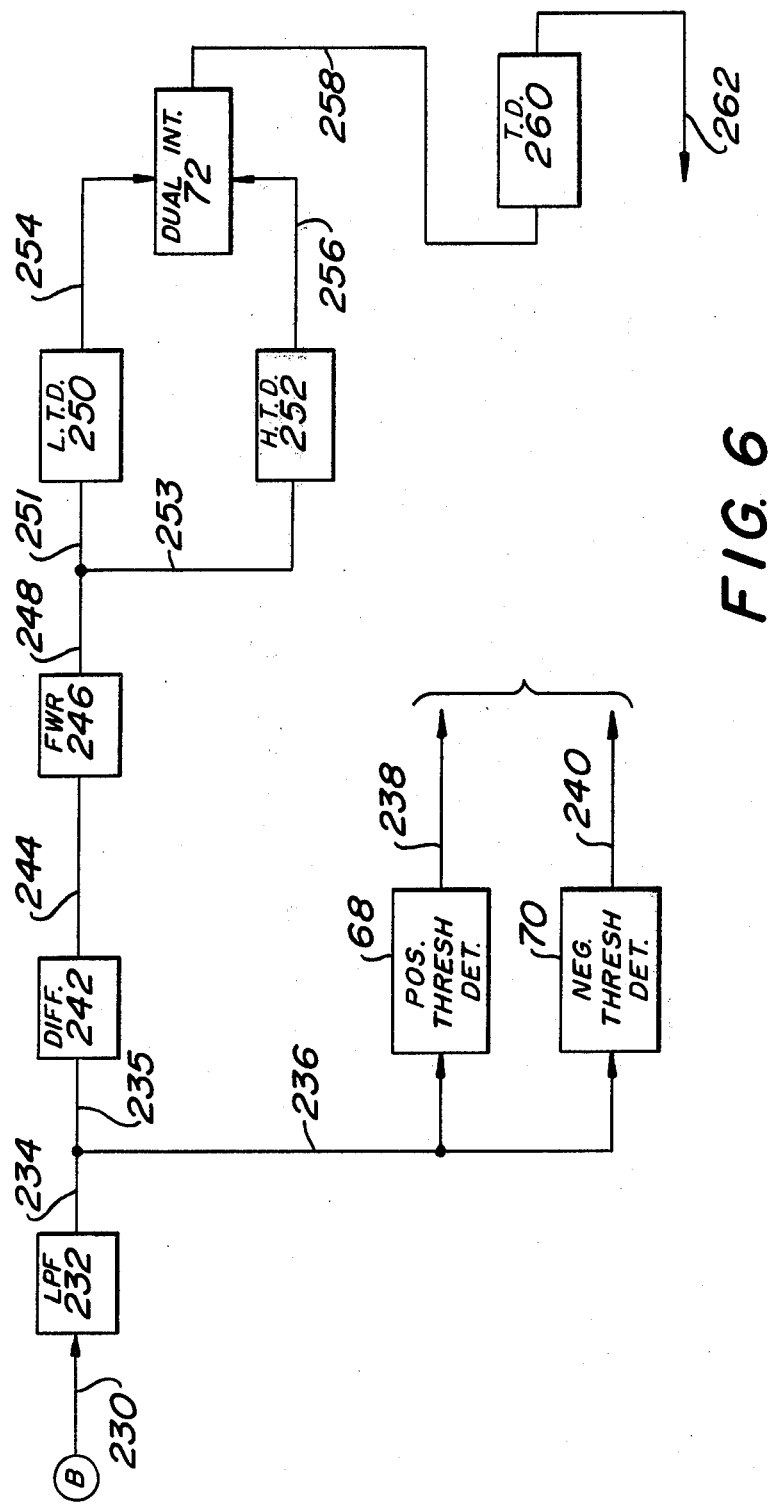
FIG. 6 is a block diagram of the base line artifact detectors.

A third functional area of pre-processor 32 is directed to a base line artifact detection. Referring to FIG. 6, signal emitted from positive threshold detector 68 and negative threshold detector 70 are output on respective lines 238 and 240, and are then fed back to first micro-computer 34, as is shown in FIG. 5. Additionally, signals emitted from dual rate integrator 72 are passed through threshold detector 260 and emitted on output line 262 for insert into first micro-computer 34 for appropriate analysis and decision making, as will be seen in following paragraphs.

Referring now in particular to QRS signal detection scheme in analog pre-processor 32, as shown in FIG. 4, it is seen that signals from patient or user 12 are input on lines 16 to differential input amplifier 74. Differential input amplifier 74 may be a field effect transistor input differential amplifier type system. The output of amplifier 74 having a gain approximating 1000, appears on amplifier output line 76, and as is the usual case, is a function of a difference between the signals applied at the input shown on line 16.

Amplifier output signals on line 76 are input into frequency response network 78, which may be one of a number of commercially available type systems currently on the commercial market. In particular use within ambulatory cardiac monitoring system 10 of the subject invention, frequency response control network 78 is set to a controlled boundary approximating 0.5 Hertz or 0.05 Hertz through a simple RC change.

The output signal from frequency response control network 78 is passed and directed on line 80 into automatic gain control system 82. Automatic gain control system 82 is a substantially standard circuit used to maintain the output in a substantially constant signal regardless of variations of signals being input on line 80. The circuit used in system 10 is found in Linear Applications Handbook 2, published by National Semiconductor and in particular, is found in Section AN129-1.

Dual output lines 86 and 88 exit the output signal from automatic gain control circuit 82 to analog/digital converter 36 and differentiator network 84 respectively. Differentiator network 84 is a standard differentiating network circuit found in Philbrick Applications Manual for Operational Amplifiers, published by Philbrick Nexus Research, Second Edition, and is found in Section II.21.

Figure 3B:
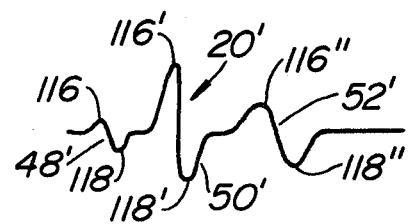

Output of differentiated network 84 on line 92 is a differentiated ECG signal 20, as shown in FIG. 3b. It is important to note that differentiator network 84 is used in coupled relation with automatic gain control system 82 to provide the differentiated ECG signal 20 on line 92. It has been found that utilization of differentiator network 84 provides a clear signal output as to initiation and termination of particular sections of overall ECG signal 20 complexes.

The use of differentiator network 84 has been found to be far more effective than any possible filter circuitry systems in use in prior art cardiac monitoring networks.

The signal emitted from differentiator network 84 is then applied to diminished sensitivity circuit 90 on line 92. As is the usual case, the signal emitted from differentiator network 84 is a bi-phase signal having both a positive pulse and a negative pulse. Automatic gain control circuit 82 does provide for a substantially nominal signal level for the positive pulse of the overall differentiated signal, however, the negative pulse of the differentiated signal passing from differentiator network 84 may be of any amplitude. The standardization of the negative pulse of the differentiated ECG signal 20 will be provided in following paragraphs concerning negative pulse automatic gain control circuit 108.

Output from diminished sensitivity circuit 90 is inserted into four pole low pass Bessel filter 94, having a cut-off value of approximately 40.0 Hertz on line 96. Bessel filter 94 is a standard filter system which is found in Function Circuits—Design & Applications, published by Burr Brown Research Corp., and is found in Paragraph 6.2.

The positive pulse having the nominal signal level passes from filter system 94 on line 98 and is driven through diode 102 into first adaptive threshold detector 54 which, as has been previously described, is a two level threshold detector, having outputs on lines 104 and 106 which are directed to micro-computer 34, as is shown in FIG. 5. Thus, threshold detector 54 is a high/low level detector system, and provides for a high positive pulse on line 104 and a low positive pulse on line 106.

The negative pulse passing from filter 94 is not standardized to a nominal signal level, and thus is passed through line 100 into long term negative pulse automatic gain control circuit 108 and is then driven through diode 110 into second adaptive threshold detector 56. Second adaptive threshold detector 56 is a high/low type detector system and emits a high negative pulse and a low negative pulse on respective lines 112 and 114. Long term negative pulse automatic gain control circuit 108 is found in Linear Applications Handbook 2, in Section AN129-1, published by National Semiconductor Corp.

Each of the pulses on lines 104, 106 and 112, 114 are inserted into first micro-computer 34 as is shown in FIG. 5, and as has been previously described. Adaptive threshold detectors 54 and 56 shown in FIG. 4 are both of the high/low detector type systems.

For clarification of the use and objectives of detectors 54 and 56, reference is now made to FIGS. 3a–e, where ECG signal 20 is shown and includes a high value QRS complex 50, as well as smaller wave signals such as P wave 48 and T wave form 52. The low portion or section of detectors 54 and 56 responds to QRS wave form 50 and in a majority of cases, may also response to P wave 48 and T wave 52. The low threshold of adaptive threshold detectors 54 and 56 is nominally set at approximately 22.0 percent of the average pulse peak amplitude.

However, as has been previously noted, the subject matter of P wave 48 and T wave form 52 for the purposes and objectives of the subject system 10 represent generally unwanted information. The high level detector of threshold detectors 54 and 56 predominantly respond to QRS wave form 50, however, in order to avoid detection of P wave form 48 and T wave form 52, the high level threshold is set in a manner such that waves 48 and 52 are normally ignored. Thus, the high threshold detector is incapable of detecting the beginning of QRS wave 50, since such will be below the detection point of the high threshold level detector. The high level threshold is therefore nominally set at 33.0 percent of the average pulse peak amplitude. In order to detect the beginning or initiation of QRS wave complex 50, the low threshold detector of adaptive threshold detectors 54 and 56 are provided.

Referring now to FIG. 3b, there is shown differentiated ECG signal 20' corresponding to ECG signal 20, shown in FIG. 3a. Differentiated ECG signal 20' includes both positive and negative pulses for each of the corresponding signals 48, 50 and 52, as provided in FIG. 3a. Thus, differentiated P wave 48' includes positive pulse 116 and negative pulse 118. Correspondingly, differentiated QRS complex 50' includes positive pulse 116' and negative pulse 118'. Similarly, differentiated T wave 52' includes both positive pulse 116'' and negative pulse 118''.

FIG. 3 provides for the positive pulse information of differentiated wave signal 20', as was depicted in FIG. 3b. Thus, the positive pulse information in FIG. 3c includes wave forms 116, 116', and 116''. In FIG. 3c, the negative pulse information has been stripped from differentiated ECG signal 20', as was shown in FIG. 3b.

Figure 3C:
Figure 3D:
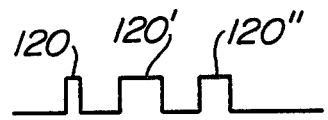
Figure 3E:
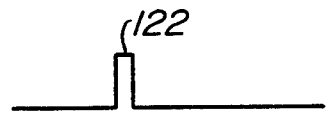

FIGS. 3d and 3e provide for the graphical representation of the representative signals of the positive pulse low threshold detector output, and the positive pulse high threshold detector output, respectively. As shown in FIG. 3d, the positive pulse low threshold detector of detector systems 54 and 56, present corresponding wave signals to positive pulses 116, 116', and 116'', as shown in FIG. 3c. It is noted that in this case, since what is being represented is a low threshold detector, all of the positive pulse information sections are represented.

The positive pulse low threshold detector signal representation is shown in FIG. 3d, and is represented by information signals 120, 120', and 120''. The positive pulse high threshold detector signal 122 is shown in FIG. 3e.

The combination of signals is passed to micro-computer 34 and if a high threshold detect signal 122 is seen, then a search is made within micro-computer 34 to determine whether there is a low threshold detect such as signal 120, which would be contiguous to the high threshold detect signal 122. Where a signal 120 is noted, the high threshold detect signal 122 is recognized as QRS signal 50 at the off-set or the on-set of that particular pulse. Both on-set and off-set are used in micro-computer 34 to measure the width of the QRS complex 50. In this manner, detection of QRS signal 50 is determined responsive to the system analysis, as has been previously described in preceding paragraphs.

Referring now to the morphology detection system of overall cardiac monitoring system 10, it is seen in FIG. 4 that subsequent to passage of ECG signal 20 through automatic gain control circuit 82, that such signal 20 exits on branch lead line 86 and is coupled through line 87 to analog/digital converter 36. The automatic gain controlled ECG signal 20 is converted to a digital format within analog/digital (A/D) converter 36 which is then inserted to micro-processor 34 on line 124. It is to be noted that line 124, A/D converter 36, and input lead line 87 is reproduced in FIG. 5 for purposes of clarity, since the following paragraphs are directed to a description of the elements and processes involved in FIG. 5.

The digital quantization of ECG signal 20 is placed into the memory portion of micro-processor 34 subsequent to being inserted therein on lead line 124 from A/D converter 36. The digital ECG signal 20 is maintained in the memory portion of micro-processor 34 for a predetermined time approximating 80.0 milliseconds and is then exited on micro-processor exit lines 126.

Obviously, the digital signal exiting from micro-processor 34 is an eight bit signal and correspondingly exit line 126 is actually eight lines, one line per bit. However, for purposes of clarity, micro-processor exit line 126 shown in FIG. 5, is schematically represented by one exit line. With the digital quantization of ECG signal 20 being maintained in memory for the aforementioned predetermined time of approximately 80.0 milliseconds, a digital delay is provided and such digital delayed quantized ECG signal information is then input to digital/analog converter 128. Digital/analog converter 128 re-forms ECG information signal into an analog signal, however, such analog signal is delayed by approximately 80.0 milliseconds, as has herein been described. Digital/analog converter 128 is well-known and commercially available in the field.

Of extreme importance in the overall medical analysis of patient or user 12 is the ability to determine changes or variations in particular spectral elements in QRS complex 50, and in particular, to investigate spectral elements in the 0.05 to 40.0 Hertz bandpass.

In order to accomplish this analysis phase of user 12, the output delayed automatic gain controlled signal of ECG signal 20 is provided on line 130 to bandpass filter system 132 which is a 40.0 Hertz Bessel bandpass filter of the two pole variety. Bandpass filter system 132 is chosen as a Bessel filter, due to the fact that phase distortion is generally minimized which would result in overshoot filter response. Additionally, bandpass filter system 132 is shown in Function Circuits Design Applications in Section 6.1.3.

The output signal of Bessel bandpass filter 132 is provided on line 134 and is a bi-phasic series of pulses predominantly occurring during a QRS interval. The bi-phasic series of pulses occur during the QRS interval due to the fact that it has been found a high percentage of 40.0 Hertz energy occurs within the QRS interval range. The bi-phasic signal passes to full wave rectifier 136 where the input bi-phasic signal is rectified and exited on line 138 for insert to gated integrator element 140. The full wave rectifier 136 is well-known in the art and is clearly shown in Philbrick Applications Manual for Operational Amplifiers, in Section III.54.

Gated integrator 140 is actuated responsive to REFRAC signal 144 shown in FIG. 9g, which is developed in micro-processor 34 and inserted to gated integrator 140 on REFRAC signal line 142. Gated integrator 140 is well-known in the art and is clearly described in Linear Applications, published by National Semiconductor and is shown in Section AN20-4.

As is seen in FIG. 9g, REFRAC signal 144 is a step signal extending for approximately 225.0 milliseconds and is initiated upon detection of QRS signal 50, as is shown in FIG. 9a. REFRAC signal 144 controls gated integrator 140 and allows integration during the 225.0 millisecond period of time that REFRAC signal pulse 144 is in an actuated state. REFRAC signal 144 is thus the actuating control of integrator system 140 operating on the signal being inserted on line 138 from full wave rectifier 136.

Thus, the signal energy from QRS wave complex 50 is delayed within micro-processor 34, filtered within bandpass filter 132, rectified within rectifier system 136, and passes from gated integrator 140 on line 146 in an integrated state.

Figure 7:
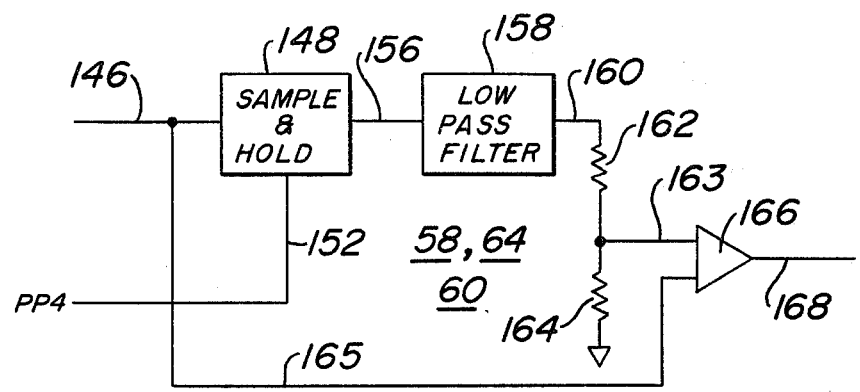
FIG. 7 is an electrical block diagram of the adaptive threshold detectors.
Figure 8:
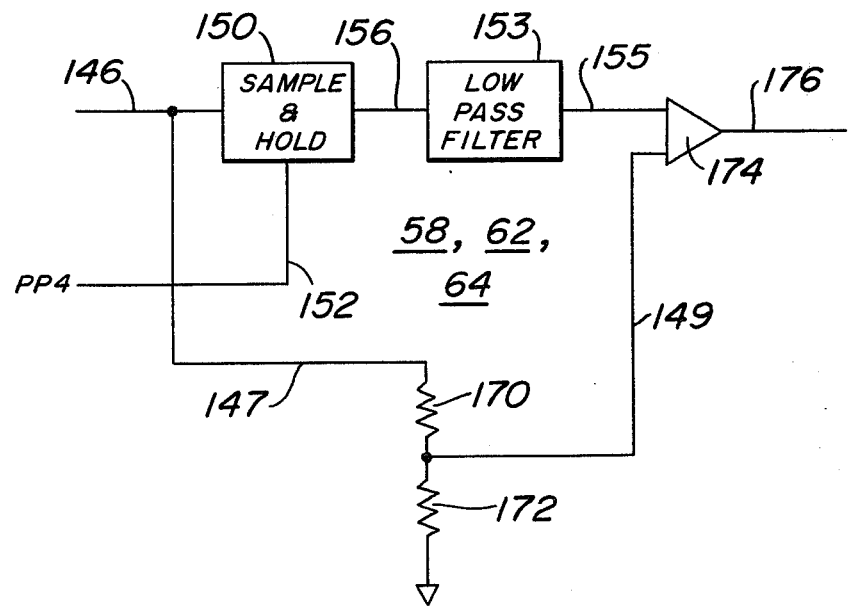
FIG. 8 is an electrical block diagram of the adaptive threshold detectors.

Output signal from gated integrator 140 is a pedestal signal and is applied to adaptive threshold detector 58 shown in FIGS. 7 and 8. The overall adaptive threshold detector 58 is seen to be actually formed of two adaptive threshold detectors. The pedestal signal on line 146 is input to both sample and hold circuits 148 and 150 on common line 146, as shown in FIGS. 7 and 8. The input command for sample and hold circuits 148 and 150 are provided by micro-processor 34 and inserted to each of sample and hold elements 148, 150 on line 152, upon which there is input PP4 signal 154.

The overall concept of signal PP4 being inserted into adaptive threshold detectors 58, 60, 62, and 64 on line 152 is seen in FIG. 5. Referring to the timing diagram of FIG. 9, the signal PP4 is seen in FIG. 9j and is a pulse lasting approximately 4.0 milliseconds and being actuated approximately 216.0 milliseconds after the initiation of REFRAC signal 144 shown in FIG. 9g.

The input command on line 152 to both sample and hold circuits 148 and 150 is initiated for normal beats of the heart of user 12. If a particular heartbeat is determined to be premature or to be another type of morphological measurement which would be classified abnormal, then the command to sample and hold circuits 148 and 150 are not provided. Thus, sample and hold circuits 148 and 150 shown in FIGS. 7 and 8 hold the previous signal from the next adjacent normal heartbeat.

The components of the overall adaptive threshold detector shown in FIGS. 7 and 8 are provided in FIG. 7 to not exit a signal when the input signal on line 146 is less than a predetermined percentage value. The corresponding component set in FIG. 8 is provided to detect and output a signal when an input signal on line 146 is greater than a predetermined value.

Referring now to FIG. 7, the output signal on line 156 from sample and hold circuit 148 is input to low pass filter 158. The subsequent filtered signal exits on line 160 and is further voltage-divided through resistive elements 162 and 164 for insert into comparator 166. This input to comparator 166 is thus a filtered signal, however, being voltage-divided and is inserted on line 163.

Another input to comparator 166 is the tapped signal from line 146 and is input on line 165 to comparator 166 in the normal fashion. Thus, the input signal on 165 in combination with the low pass filter signal on line 163 provides for the total input of comparator 166. Both low pass filter 158 shown in FIG. 7 and low pass filter 153 shown in FIG. 8 are standard low pass filter systems clearly shown in Function Circuits Design and Application, and found in Section 6.1.1.

If the tapped signal on line 165 is nominally greater than a predetermined threshold percentage value, then such provides an appropriate signal for comparator 166 for output of information on comparator line 168. However, if an input signal passing on line 165 from input line 146 is less than the predetermined threshold value for a pathological or physiological reason, such will not exceed the threshold of comparator 166 and there will be no signal developed on output line 168. It is to be noted for purposes of clarity, that overall adaptive threshold detector 58 and corresponding output line 168 leading to micro-processor input line 66 is also shown on FIG. 5.

Referring now to FIG. 8, it is seen that the input signal on line 146 is tapped on line 147 for insert into voltage divide elements 170 and 172. In general, a normal heartbeat does not exceed the reference signals passing on line 160 from low pass filter 158 (shown in FIG. 7) due to the fact that such has been voltage-divided, as has been described. The voltage-divided signal from line 147 is input to comparator 174 on comparator input line 149. Where the normal heartbeat does not exceed the reference signal, there is no output from comparator 174 on comparator line 176. However, if the input signal on line 146 is higher than the nominal value, the result will exceed the reference signal and comparator 174 develops an information signal on line 176. The output of comparators 166 and 174 are provided on respective lines 168 and 176, which are in turn fed back through micro-processor 34 as schematically represented by line 66 shown in FIG. 5.

As shown in FIG. 5, the high frequency decrease signal (HFD) passing on line 168 developed in comparator 166, shown in FIG. 7, provides a signal for each heartbeat of user 12 and only in the absence of a signal emanating from comparator 166 is there an indication of detection. On high frequency increase line 176, there is normally no high frequency increase signal (HFI) being exited from comparator 174 until a morphology change occurs which causes an output signal from comparator 174 on line 176. For purposes of operation, the high frequency increase threshold is generally set at approximately 20.0 percent greater than the average signal from first gated integrator 140, whereas the high frequency decrease threshold is generally set at approximately 20.0 percent less than the average signal from first gated integrator 140.

Thus, the two signals passing on line 168 and 176, respectively referred to as HFD and HFI, indicate that either the amount of 40.0 Hertz energy is within a nominal range in which case there will be a high frequency decrease signal (HFD) on line 168, and in the absence of the high frequency increase signal on line 176. If there is a sudden decrease of signal, or a sudden increase in 40.0 Hertz energy, the high frequency decrease signal line 168 will have an absence of a signal imposed thereon and the high frequency increase line 176 will sense the presence of an information signal. Each of the signals on line 176 and 168 are passed to micro-processor 34 on multiple line 66, wherein a program is initiated to be discussed in following paragraphs.

Referring now to the low frequency morphology detection scheme shown in both FIGS. 4 and 5, it is seen that the non-delayed AGC'D ECG signal 20 emitted from automatic gain control system 82 passes in one path through line 86 to connector line 212. Connector line 212 is coupled to bandpass filter 214, shown in FIG. 5, and the connection input is provided in the block diagrams through the coupling letter "A".

Bandpass filter 214 is a 2.0–30.0 Hertz bandpass filter of the two pole variety, having inherent delays contained therein. The inherent delays of element system 214 obviate the need for use of a delaying signal, as has been previously described in other circuitry schemes within this concept. Further, it is to be understood that by not delaying signals from second gated integrator 216 during a particular time frame, energy from QRS signal 50 in addition to signals from T wave form 52, are allowed to pass, and such includes information relative to any abnormal beats from patient or user 12.

Bandpass filter 214 is of the Bessel type, in order that the non-delayed signal avoids any phase distortion. Output of bandpass filter 214 is a bi-phasic signal passing on line 218 and is inserted into full wave rectifier 220 in order to provide a single phase signal on output line 222. The single phase signal on output line 222 is then inserted into previously referred to second gated integrator 216.

The signal on line 222 is integrated within integrator 216 during the time of REFRAC signal 144 shown in FIG. 9g, passing from micro-processor 34 on line 142, and being tapped on line 143 into gated integrator 216. As shown in FIGS. 9g and 9a, this time interval of the operational phase of REFRAC signal 144 occurs for approximately 225.0 milliseconds and is initiated at the beginning of detection of QRS wave complex 50.

The gated integrated signal emanating from second gated integrator 216 exits on line 224 and is inserted into adaptive threshold detector 64, which includes the circuit elements as shown and previously described in FIGS. 7 and 8.

In this manner, two output signals are provided from adaptive threshold detector 64. A low frequency increase signal (LFI) on line 226 and a low frequency decrease signal (LFD) on line 228 is derived as a signal when there is an abnormal change in energy within the 2.0–30.0 Hertz bandpass filter system 214. The low frequency increase threshold is set at approximately 20.0 percent greater than the average signal from second gated integrator 216. Further, the low frequency decrease signal is set at approximately 20.0 percent less than the average signal from second gated integrator 216.

Each of the low frequency increase and low frequency decrease signals are applied to micro-processor 34 on respective lines 226 and 228, and are utilized as signal elements in the decision making process for classifying the heartbeat of user 12 in micro-processor 34. Both the LFI and LFD signals on lines 226 and 228 are input to coupling line 66 for insert into micro-processor 34.

Referring now to another path circuitry scheme in the overall morphology system in FIG. 5, there is the branch phase for determination of whether there is a change in QRS wave complex 50 morphology. Such a change or variation is represented in overall concept by a change in a differentiator output. The output from digital to analog converter and low pass filter element system 128 exists on line 130 and is inserted to differentiator 180 on differentiator input line 178.

A forcing or off-set voltage is also input to differentiator 180 on line 182. The off-set voltage input on line 182 compensates for the nominal junction voltage drops in various diodes contained within the overall circuit system. With the input on input line 182 set to cause a 0.6 voltage off-set, the output of differentiator 180 on line 184 is a differentiated ECG signal 20', except delayed approximately 80.0 milliseconds, as is clearly shown in FIGS. 3b and 9b.

The signal passing on line 184 is branched into signal lines 186 and 198. The differentiated signal is passed on diode input line 185 through diode 188 having an associated diode junction voltage drop. The off-set voltage of approximately 0.6 volts input on line 182 is thus shed to provide an output from diode 188 having a positive pulse which represents a full pulse as referred to a predetermined base line.

It is to be understood that if the off-set voltage input on line 182 was not presented to differentiator 180, then the positive pulse leaving or exiting diode 188 on exit line 190 would be exclusive of the 0.6 off-set voltage. Thus, any signal magnitude from a set base line or zero condition up to 0.6 volts would be excluded by diode 188 in the junction drop.

The signal on line 190 passing from diode 188 is inserted to first gated peak detector 192 and exits on line 194 for insert into third adaptive threshold detector 60, as has been shown and described in FIG. 7. First gated peak detector 192 charges to the peak value of the particular lobe, as provided by diode 188, and holds that voltage signal until sample and hold amplifier 148 in adaptive threshold detector 60 incorporates the signal. REFRAC signal is a gating signal which, when active, allows gated peak detector 192 to charge to the differentiated QRS signal peak. When the REFRAC signal returns to a zero or base line condition, peak detector 192 discharges. REFRAC signal 144 is inserted to first gated peak detector 192 on input line 193 from REFRAC micro-processor line 142. Thus, as has been shown, REFRAC signal 144 shown in FIG. 9g is the control signal for first gated peak detector 192.

Subsequent to first gated peak detector 192 being discharged, the detector 192 is in condition for charging to a next successive value, however, such will not charge unless REFRAC signal 144 is in an active state. It is to be noted that the signal from the heartbeat which has previously occurred, is maintained in sample and hold circuit 148 as is shown in FIG. 7.

As can be seen in FIG. 5, passage of the input signal to third adaptive threshold detector 60 exits on line 177 to provide a positive peak differential decrease signal (PPDD). The positive peak differential decrease signal on line 177 is then inserted into multiple micro-processor input line 66 for insert into micro-processor 34.

It is to be understood as previously described, that the signal on input line 178 to differentiator 180 is bi-phasic in nature, and the passage through diode elements 188, first gated peak detector 192, and third adaptive threshold detector 60, accounts for only one-half of the differentiated and delayed ECG signal input on line 130 from system 128.

In order to account and provide for the secondary portion of the signal, inverter 196 is coupled to output line 184 through inverter line 198. An off-set voltage on line 202 is applied to inverter 196 to compensate for the threshold of diode 200 having an input signal on line 197 from inverter 196.

Since the input signal to inverter 196 is inserted subsequent to the actuation of differentiator 180, it is noted that the input signal is off-set from differentiator 180. Thus, inverter 196 is coupled to a separate and distinct off-set voltage input which is input on line 202 in order to null out the off-set voltage of the preceding state of differentiator 180.

The output of diode 200 passes on line 204 into second gated peak detector 206, which is similar in construction to gated peak detector 192 as previously described. Both gated peak detectors 192 and 206 are well-known circuits, and are provided in Philbrick Operations Manual for Operational Amplifiers, Section III.49.

Output of gated peak detector 206 passes on line 208 into fourth adaptive threshold detector 62 which is similar in nature to adaptive threshold detector 60, as shown in FIG. 7 and results in a negative peak differential decrease signal (NPDD) on output line 210. In a similar manner to gated peak detector 192, second gated peak detector 206 is controlled by REFRAC signal 144, shown in FIG. 9g being input on line 195, which is tapped from REFRAC signal line 142 emanating from micro-processor 34. The threshold of fourth adaptive threshold detector 62 is nominally set at 80.0 percent of the average peak amplitude signal from second gated peak detector 206.

Referring now to FIG. 6, there is shown the circuit block diagram for the base line artifact detector for sensing the excursion of a base line beyond certain predefined limits or to detect a change in the base line voltage, in which the rate of change is such as to cause a misinterpretation within ambulatory cardiac monitoring system 10.

The input to base line artifact detector system as shown in FIG. 6, is made on input line 230, where the coupling letter "B" is provided. Input on line 230 passes from automatic gain control system 82 on exit line 86 shown in FIG. 4, to input line 230. The AGC'D ECG signal is filtered by 2.0 Hertz low pass Bessel filter element 232 to remove both T wave form 52 and QRS wave complex 50 from the energy signal.

The exit signal from low pass filter element 232 on line 234 is predominantly and essentially the base line of ECG signal 20. The output signal from element 232 is provided in a dual path where the output on line 236 passes to threshold detectors 68 and 70.

Positive threshold detector 68 senses when the excursion of the base line is exceeded at a predetermined positive threshold level. Alternatively, negative threshold detector element 70 senses when the base line provides an excursion below, or in a negative mode beyond a predetermined value. Output signals from positive threshold detector 68 and negative threshold detector 70 is outputted on respective output lines 238 and 240, which are inserted into micro-processor 34, as is clearly shown in FIG. 5.

The signal emanating from low pass filter element 232 is also directed to line 235, which is an input line for differentiator element 242. The base line signal derived from 2.0 Hertz low pass filter 232 is differentiated within differentiator 242, and exited on line 244, as a differentiated signal for insert into full wave rectifier 246.

Subsequent to full wave rectification, the differentiated signal passes on line 248 and is inserted into low threshold detector 250 and high threshold detector 252 on respective lines 251 and 253. Low threshold detector 250 and high threshold detector 252 are not adaptive threshold detectors, but absolute voltage detectors well-known in the art. Both detectors 250 and 252 circuitry is clearly shown in Linear Applications published by National Semi-Conductor, and shown in Section AN4-1.

Exit signals from low threshold detector 250 and high threshold detector 252 are inserted into dual rate integrator 72 on input lines 254 and 256. The overall concept of dual rate integrator 72 is to allow the integrator to reach a threshold of threshold detector 260 by a plurality of mechanism. Integrator 72 may reach the threshold of threshold detector 260 (1) where a signal is high but of short duration wherein integrator 72 will climb in a rapid fashion; (2) where a signal of a lower threshold persists over a long time duration such will cause integrator 72 to climb to the threshold of detector 260; and/or (3) where there is a combination of a high signal for a short duration of time and a low signal for a longer duration of time. The circuitry for dual rate integrator 72 is clearly defined in Philbrick Applications Manual for Operational Amplifiers and shown in Section II.10.

The output on lines 258 from dual rate integrator 72 depends upon the signal level and duration of time from the input source signals on lines 254 and 256. Threshold detector 260 is coupled to integrator 72 through line 258, as is shown. The output of threshold detector 260 on line 262 is then fed back to micro-processor 34 as is shown by input line 262 in FIG. 5. The output of threshold detector 260 is only determined when integrator 72 exceeds a predetermined signal level.

Referring now to FIG. 5, there is also provided a base line noise circuit system based around threshold detector 304. As is seen, an eighty millisecond delayed AGC'D ECG signal 20 is input into 40.0 Hertz band filter 132. This signal passing on line 134 is inserted into full wave rectifier 136, as has previously been described. Full wave rectifier 136 provides for a uni-phasic signal to threshold detector 304 on threshold detector input line 302. Threshold detector 304 is set at a threshold which is at a predetermined point where signal levels in the 40.0 Hertz pass band would not be normally exceeded during the period between QRS signals 50, as is shown is FIG. 9a.

During QRS signals 50, there is enough 40.0 Hertz energy in QRS signals 50 to exceed the level of threshold detector 304. Signals exiting on line 306 are input to micro-processor 34, as is shown. The signal line 306 is normally activated resulting from QRS signals 50, and during times of artifacts where 40.0 Hertz signal levels exist during the period between QRS signal inputs.

Micro-computer 34 is programmed to ignore signals on line 306 during the time interval in which QRS signals are known to exist.

Referring now to FIG. 4, there is shown output line 400 exiting from micro-processor 34 to provide input to adaptive threshold detector 54. Impressed on output line 400 is BOOTSTRAP signal 402, shown in timing diagram FIG. 9h. As is seen, BOOTSTRAP signal 402 is a 120.0 milli-second signal developed by micro-computer 34. Signal 402 relates only to the high level positive pulse detector and for the 120.0 milli-second time duration, increases the sensitivity of the positive pulse high level detection. The increased sensitivity occurs at the onset of either the positive pulse detection, or the negative pulse detection and remains in such a condition for 120.0 milli-seconds. Once QRS signal 20 is detected, the sensitivity is increased due to the fact that there may be pulses in the QRS signal 20 that have insufficient amplitude to cross a normal threshold level, yet such pulses may still define and are necessary to define the overall QRS signal 20.

As is seen in FIG. 4, output line 404 from micro-computer 34 is inserted into diminished sensitivity element 90. The signal on line 404 is referred to as TOO BIG and is provided when a premature ventricular contraction has a very high amplitude ratio relative to normal beats from patient 12.

In some cases, the premature ventricular contraction may be misinterpreted as an artifact. In order to prevent any misinterpretation, the TOO BIG signal is sensed by analog/digital converter 36 having an output at its maximum or minimum points. In such cases, A/D converter 36 would either have all "1's" or "0's" outputs. Such a designation in all eight bits would indicate that the amplitude of the input signal has exceeded the A/D converter 36 range. It is to be understood that the use of eight bit A/D and/or D/A converters is purely illustrative in relation to the overall concept. For purposes of operation, twelve bit A/D and/or D/A converters may be used with a plurality of operable thresholds adaptable for use.

Micro-computer 34 is coded to sense the either high or low condition, as has been previously described, and outputs a squelch signal (TOO BIG) which is input to diminished sensitivity element 90. This signal input to diminished sensitivity element 90 squelches the total ECG signal 20 for a period approximating 225.0 milliseconds after detection, in order that no unusually high amplitude signals are sent to the QRS detection circuit and the bandpass filter circuits 94. The TOO BIG signal 20 may further be caused by base line off-set and in such condition will extend until a next beginning of a QRS signal detection.

Referring now to a further control signal labeled DIMINISHED SENSITIVITY in FIG. 4, it is seen that such exits micro-processor 34 on line 406 and is inserted into diminished sensitivity circuitry 90. Diminished sensitivity signal 408, as shown in FIG. 10i, is initiated after a predetermined time from the beginning of QRS detection and is terminated at a subsequent time interval which is rate dependent and calculated by the coded micro-computer 34 in the program listing as provided in following paragraphs.

Diminished sensitivity signal 408 suppresses T wave 52 in order that the QRS detectors will not respond falsely. Thus, during actuation of signal 408 subsequent to the QRS detect, the sensitivity of the QRS detector is diminished by approximately 50.0 percent to avoid T wave detection. The particular time period of signal 408 is a function of heart rate, as determined by the coded program within micro-computer 34.

A further signal AGCA is shown in FIG. 4 emitted by micro-processor or micro-computer 34 to automatic gain control system 82. The AGCA signal is sent to AGC 82 for each heartbeat of user 12, but is not emitted upon a premature beat or when the TOO BIG signal occurs.

Micro-computer 34 is programmed in assembly language. The program function is to receive predetermined signals from pre-processor 32 regarding morphology and timing and to make detection decisions for functions such as premature ventricular heart contractions, ventricular tachycardia, alternate normal premature ventricular contractions, low threshold premature ventricular contractions, and artifacts which are essentially signals other than signals generated by the heart of patient 12.

Micro-computer 34 is also in a control loop with pre-processor 32 and the program provides control functions to pre-processor 32 which include REFRAC signal 144 being a 225.0 milli-second pedestal signal occurring at the on-set of the detection of QRS signal 50. Another control signal is DIMINISHED SENSITIVITY signal 408 which is initiated at a predetermined time after the beginning of QRS signal 50 detection and terminating at a subsequent time which is rate dependent and calculated by the coded micro-processor program. A still further control function is PP4 signal 154 occurring at 216.0 milli-seconds after the initiation of QRS signal 50 and extending to 225.0 milli-seconds, which is only developed if micro-processor 34 in its other determination has found the heartbeat to be within the normal range.

In order to provide a full and complete description for ambulatory cardiac monitoring device 10, the computer program in Assembly Language for microprocessor 34 is detailed in the following pages:

```
RECLST   CSOP    P ID=MEDICAL    13.10.13   SATURDAY 27 OCTOBER 1979
   NATIONAL CSS, INC. (STAMFORD DATA CENTER)              EAST

FL LOC   COSMAC CODE     LNNO  SOURCE LINE
  0000                    1   ..MEDICAL CONCEPTS INC.
  0000                    2   ..UNIVERSAL SYMBOLS  COPYRIGHT:20OCT78
  0000                    3   ..
  0000                    4   ..WORKSPACE ADDRESSES :
  0000                    5   UPDNCT=#5800      ..UP DOWN ART TIME CNTR.
  0000                    6   ARTFAG=UPDNCT+1   ..#QRS'S TO REMOVE ART
  0000                    7   WQRSTK=ARTFAG+10  ..QRS WIDTH STACK
  0000                    8   QRSWID=WQRSTK+1   ..CURRENT WIDTH
  0000                    9   SETWID=QRSWID+1   ..SHR(2)LDCDE
  0000                   10   PPMREF=SETWID+5   ..PPM NORMAL STACK
  0000                   11   PNLDCT=PPMREF+1   ..PLD,NLD CTR.
  0000                   12   PLDMRK=PNLDCT+1   ..1=PLD (POSITIVE LEVEL DETECT)
  0000                   13   INPWRD=PLDMRK+1   ..INPUT WORD
  0000                   14   INBFWD=INPWRD+1   ..INP.BUFFERED WORD
  0000                   15   INPDAT=INBFWD+1   ..INPUT DATA(CHAS)
  0000                   16   CODWDS=INPDAT+9   ..CODE WORDS STACK(9)
  0000                   17   MODCTL=CODWDS+1   ..MODE CONTROL BYTE
  0000                   18   MO2CTL=MODCTL+1   ..MODCTL NO.2
  0000                   19   OLDTIM=MO2CTL+42  ..OLDTIM.1,T(N-I) STCK(40)
  0000                   20   SCRSTK=OLDTIM+10  ..SCRATCH STACK(9)
  0000                   21   TCP10Q=SCRSTK+1   ..1/4 *TCP10
  0000                   22   TCP10E=TCP10Q+2   ..1/8 *TCP10
  0000                   23   TCP10H=TCP10E+2   ..1/2 *TCP10
  0000                   24   TCP10=TCP10H+2    ..TIME COMP.PAUSE * 10
  0000                   25   TCP11=TCP10+2     ..1.1 * TCP10
  0000                   26   ITPSHT=TCP11+2    ..INTERPOLATED SHORT TIME
```

```
 27 ITPLNG=ITPSHT+2  ..INTERPOLATED LONG TIME
 28 TCP09=ITPLNG+2   ..TCP10 *.9
 29 TCP27=TCP09+2    ..TCP09 *3
 30 TP32=TCP27+2     ..PREM.TIME * 32
 31 HLDLNG=TP32+2    ..HOLD (TCP20-20*300MS.)
 32 TCP105=HLDLNG+2  ..(TCP10/2)+(TCP11/2)
 33 OLDT5=TCP105+2   ..OLDTIM*5
 34 OLDT6=OLDT5+2    ..OLDTIM*6
 35 OLDT10=OLDT6+2   ..OLDTIM*10
 36 LTHTME=OLDT10+2  ..LOW THRESH. TIME
 37 TLAG=LTHTME+2    ..TLD-TLLD
 38 TLLD=TLAG+2      ..TIME LOW LEVEL DET.
 39 TLD=TLLD+2       ..TIME HIGH LEVEL DETECT
 40 SAMECT=TLD+2     ..=0 FOR PPM REPEAT
 41 BEATBK=SAMECT+1  ..BEAT#(BACKGROUND)
 42 REFADR=BEATBK+1  ..A(REFRAC ONSET) *
 43 TOLGCT=REFADR+1  ..#R-R*S >210%
 44 BKUPCT=TOLGCT+1  ..# BACKUPS TOLERATED
 45 SVSTKX=BKUPCT+1  ..SAVE INTRPT _DSTKX
 46 UPDCTM=SVSTKX+1  ..UPDCOM COMPLETION TIME.0,1
 47 SOTME=UPDCTM+2   ..BACKGD REFRAC COMPLETION TIME.0
 48 DIMTME=SOTME+2   ..DIMSENK- OFF
 49 T5P10=DIMTME+2   ..TCP10(SUM OVER 5)
 50 ALGART=T5P10+2   ..STRETCHES ARTS
 51 ARTBAG=ALGART+1  ..ARTFAG,BUT BY BEATS
 52 STABCT=ARTBAG+1  ..STABLE? UP DOWN COUNTER
 53 NL0PNL=STABCT+1  ..PNLDCT T(N) FINGERPRINT
 54 NL0MRK=NL0PNL+1  ..PLOMRK
 55 NL0INP=NL0MRK+1  ..INPWRD
 56 NL0WID=NL0INP+1  ..QRSWID
 57 NL1PNL=NL0WID+1  ..          T(N-1)
 58 NL1MRK=NL1PNL+1
 59 NL1INP=NL1MRK+1
 60 NL1WID=NL1INP+1
 61 NL2PNL=NL1WID+1
 62 PV1PNL=NL2PNL+4  ..          OLD PVC#1
 63 PV1MRK=PV1PNL+1
 64 PV1INP=PV1MRK+1
 65 PV1WID=PV1INP+1
 66 PV2PNL=PV1WID+1  ..          OLD PVC#2
 67 PV2MRK=PV2PNL+1
 68 PV2INP=PV2MRK+1
 69 PV2WID=PV2INP+1
 70 SVLNGX=PV1PNL+36 ..SAVE LNGX CONTENTS
 71 BKLNGX=SVLNGX+2  ..SVLNGX IN BACKGROUND
 72 OUTIND=BKLNGX+2  ..OUTPUT INDICATIONS
 73 ADAOLD=OUTIND+1  ..A/D CONV. ART. OLD
 74 ADANEW=ADAOLD+1  ..A/D CONV. ART. NEW
 75 WIDAIN=ADANEW+1  ..WIDE LTE.ARTS INHIB.
 76 ENDCHR=WIDAIN+1  ..END CHAR ADDR.0
 77 CASCTL=ENDCHR+2  ..CASSETTE CONTROL BYTE
 78 RECTRL=CASCTL+1  ..RECORD CONTROL MODE
 79 DATQUE=RECTRL+1  ..HOLDS DATA RECORD REQUEST
 80 EKGQUE=DATQUE+1  ..HOLDS EKG RECORD REQUEST
 81 EKGCTR=EKGQUE+1  ..# EKG BLOCKS REMAINING
 82 EKGAL2=EKGCTR+1  ..EKG ALARM CODES 2
 83 EKGAL1=EKGAL2+1  ..  "   "    "    1
 84 EKGBF2=EKGAL1+1  ..EKGAL2 BUFFER
 85 EKGBF1=EKGBF2+1  ..EKGAL1 BUFFER
 86 TIMER=EKGBF1+1   ..SCRATCH TIMER
 87 NARTSC=TIMER+1   ..NO ARTS 1/4 SECS.
 88 MRKPVC=NARTSC+1  ..MARKS BEAT AS PVC
 89 MRKRUN=MRKPVC+1  ..MARKS BEAT AS RUN
 90 MRKSVT=MRKRUN+1  ..MARKS BEAT AS SVT
 91 MRKPRM=MRKSVT+1  ..MARKS SUPRA PREM BEAT
 92 NLTWCT=MRKPRM+1  ..#SINGLE LEVEL DETECT T WAVES
 93 BTTWCT=NLTWCT+1  ..#NORMALS BETWEEN NLTW.
 94 RNBEAT=BTTWCT+1  ..#BEATS DURING RUN
 95 BKPERD=RNBEAT+1  ..SAVES PERIOD(')
 96 STBLNK=BKPERD+1  ..POST STARTUP BLANKING
 97 OUTMK2=STBLNK+1  ..OUTMSK'
 98 OUTMSK=OUTMK2+1  ..OUTPUT MASK
 99 LTEBTS=OUTMSK+1  ..LATE ARTIFACTS INHIBIT BITS
100 ARTBTS=LTEBTS+1  ..ARTIFACT BITS(BEATS)
101 LTUPDN=ARTBTS+1  ..LATE ARTIFACTS INHIB. UP/DN CT
102 LLDCTR=LTUPDN+1  ..LOW LEVEL DET. CTR
103 OLLD=LLDCTR+1    ..OLD LOW LEVEL DETECT
```

```
0000    104 CTRVFB=OLLO+1      ..VFIB CTR(1 SEC)
0000    105 CTRVRF=CTRVFB+1    ..VFIB SHORT REFRACTORY
0000    106 VFICTR=CTRVRF+1    ..VFIB INHIBIT UP/DOWN CTR.
0000    107 LLARTS=VFICTR+1    ..LOW LEVEL ARTS TIMER
0000    108 RECONO=LLARTS+2    ..RECORD #
0000    109 SHTBGN=RECONO+1    ..SHORT DELAY BUFF(BEGIN)
0000    110 SHTEND=SHTBGN+9    ..SHORT DELAY END
0000    111 SHTSVR=SHTEND+1    ..SAVES SHRT DLY PNTR
0000    112 ..
0000    113 ..
0000    114 STCKTP=#58FF       ..INTRPT STACK TOP
0000    115 BEATNU=STCKTP-8    ..BEAT #(INTERRUPT)
0000    116 OUTCTL=BEATNU-1    ..OUTPUT CONTROL BYTE
0000    117 REFADR=OUTCTL-1    ..A(REFRAC ONSET) INTERPT.
0000    118 ..
0000    119 LDSTKB=#5900       ..LD STACK BOTTOM
0000    120 LDSTKT=LDSTKB+#FF  ..LD STACK TOP
0000    121 ..
0000    122 DATBUF=#5A00       ..TAPE DATA BUFFER
0000    123 SYNCHD=DATBUF+4    ..SYNCHR.HEADER
0000    124 WRTRCN=SYNCHD+5    ..WRITE RECORD #
0000    125 WRTMOD=WRTRCN+1    ..WRITE MODE(ECG OR DATA)
0000    126 PERIOD=WRTMOD+1    ..15MIN PERIOD OF DAY
0000    127 MINUTE=PERIOD+1    ..0-14 MINUTES
0000    128 CODES1=MINUTE+1    ..CODES
0000    129 CODES2=CODES1+1
0000    130 CODES3=CODES2+1
0000    131 RUNCT=CODES3+1     ..RUNS CTR.(15 BIT BINARY)
0000    132 DROPCT=RUNCT+2     ..DROP BEAT CTR(BINARY)
0000    133 BEAT15=DROPCT+1    ..#BEATS IN 15SECS
0000    134 PVCMIN=BEAT15+15   ..#PVC'S/MIN
0000    135 ARTSEC=PVCMIN+15   ..COUNTS ARTIFACTS 1/4S.
0000    136 SVEBCT=ARTSEC+15   ..COUNTS S.V.E.B.'S
0000    137 SVCT=SVEBCT+15     ..SVT COUNTER(16BIT BINARY)
0000    138 CPLCT=SVCT+2       ..COUPLET 16 BIT COUNTER
0000    139 LLASCT=CPLCT+2     ..LOW LEV. ARTS SEC COUNT
0000    140 ENDATA=LLASCT+1    ..END OF DATA
0000    141 ..
0000    142 LNGBGN=#5C00       ..LONG DELAY BEGIN
0000    143 LNGEND=#5FFF       ..LONG DELAY END
0000    144 LNGLTH=#0400       ..LONG BUFFER LENGTH
0000    145 ..
0000    146 ..ADDRESS DISPLACEMENT CONSTANTS:
0000    147 DSMNRN=4   ..SECOND TO RUNCT
0000    148 DSMNDB=6   ..SECOND TO DROPCT
0000    149 DSMNBT=7   ..MINUTE TO BEAT15
0000    150 DSBTPV=15  ..BEAT15 TO PVCMIN
0000    151 DSMNAR=37  ..MINUTE TO ARTSEC
0000    152 DSPVSV=30  ..PVCMIN TO SVEBCT
0000    153 DMNSVT=67  ..MINUTE TO SVCT
0000    154 DMNCPL=69  ..MINUTE TO CPLCT
0000    155 DPOLAR=72  ..MINUTE TO LLASCT
0000    156 ..
0000    157 ..COSMAC T REGISTER CONSTANTS :
0000    158 DSTTME=#66 ..X=DST,P=RFT
0000    159 SRCCLL=#54 ..X=SRC,P=CALL
0000    160 SRCMNE=#53 ..X=SRC,P=MPC
0000    161 MNEMNE=#33 ..X,P=MPC
0000    162 CLLCLL=#44 ..X,P=CALL
0000    163 DSTMNE=#63 ..X=DST,P=MPC
0000    164 DSTCLL=#64 ..X=DST,P=CALL
0000    165 ..
0000    166 ..MISCELLANEOUS CONSTANTS:
0000    167 REFRAC=220 ..220MS.
0000    168 MAXDIM=325 ..325MS. MAX. DIMTME
0000    169 LTHRBK=#EC ..#BACKUPS TOLERATED(LTHPVC)
0000    170 ONLECT=28  ..JPONCT ON LOOSE ELECTRODES
0000    171 HALFCT=42  ..JPONCT HALF COUNT
0000    172 SEXCT=51   ..JPONCT 60% COUNT
0000    173 FULLCT=84  ..JPONCT FULL COUNT
0000    174 STABMX=30  ..STABCT MAX CNT
0000    175 MEDSTB=15  ..STABCT THRESHOLD
0000    176 MAXLL=190  ..LTUPDN MAX.
0000    177 LTETHR=62  ..LATE ARTIFACTS INHIBIT THRESHOLD
0000    178 TWOSEC=2000 ..TWO SECS.=2000MS.
0000    179 TREHUN=3000 ..10 * 300MS.
0000    180 SECS15=59  ..59*256MS.=15SECS.
```

```
0000              181 SECS60=234 ..234*256MS.=60SECS.
0000              182 KS1=#7717 ..ONE SECOND DELAY
0000              183 KMS200=#1711 ..200MS. DELAY
0000              184 MS1500=#00BB ..#*8MS.=1.5SEC.
0000              185 MS3000=#0177 ..#*8MS.=3.0SEC.
0000              186 HD3SEC=#183 ..3SEC.+HEADER
0000              187 MSKLTH=13 ..HEADER MASK LENGTH
0000              188 MS5500=#2AF ..#*8MS.=5.5 SEC.
0000              189 ..
0000              190 ..CASSETTE CONTROL CODES:
0000              191 STOPW=#1E ..STOP AFTER WRITING
0000              192 STOP=#16   ..STOP
0000              193 OFF=#14    ..CASSETTE<-OFF
0000              194 WRITE=#0E ..WRITE TO CASSETTE
0000              195 REW=#22    ..REWIND
0000              196 ..
0000              197 ..INPUT DEVICES :
0000              198 TSTIN1=1   ..TEST SWITCH #1
0000              199 TSTIN2=2   ..TEST SWITCH #2
0000              200 ADCONV=3   ..A/D CONVERTER
0000              201 CHASIG=4   ..CHARLIE'S SIGNALS
0000              202 LD=5       ..QRS LEVEL DETECT
0000              203 ..
0000              204 ..OUTPUT DEVICES:
0000              205 SHALGD=1 ..SHRT.ANLG.DELAY
0000              206 LGALGD=0 ..LONG  "    "
0000              207 FIFO=2     ..FIFO BUFFER
0000              208 CLCHAS=3 ..CLEAR CHAS LATCH
0000              209 TESTOT=4 ..TEST (4*8 S.S.R.)
0000              210 OUTSIG=5 ..SIGNALS TO ANALOG CIRCUITS
0000              211 MODPRT=0 ..LOAD MODE LED OUT PORT
0000              212 CASOUT=6 ..CONTROLS CASSETTE
0000              213 IND=7      ..LOAD INDICATING LEDS
0000              214 ..
0000              215 ..REGISTER ASSIGNMENTS :
0000              216 RFT=0 ..INIT.P.C.,QRS.SYNCHR.FUNC.TIMER
0000              217 IPC=1 ..INTERUPT P.C.
0000              218 STK=2 ..STACK POINTER
0000              219 MPC=3 ..MAIN P.C.
0000              220 CALL=4 ..SUBROUTINE P.C.
0000              221 SRC=5 ..SOURCE PNTR. (BACKGROUND)
0000              222 DST=6 ..DESTINATION PNTR.   "
0000              223 ADR=DST ..ADDRESS POINTER (INTERRUPT)
0000              224 SUM=7 ..HOLDS 2 BYTE SUM
0000              225 GR=8 ..GENERAL REGISTER(BACKGROUND)
0000              226 LDSTKX=9 ..QRS LEVEL DET. STCK. INDEX
0000              227 WRT=#0A ..WRITE TO TAPE INDEX
0000              228 LNGX=#0B ..LONG DELAY INDEX
0000              229 CPC=#0C ..CASSETTE PROGRAM COUNTER
0000              230 DAT=#0D ..DATA BUFFER POINTER
0000              231 CLK=#0E .."REAL TIME" TIMER (CLOCK)
0000              232 FPC=#0F ..DOFUNC P.C.
0000              233 ..............................
0000              234 ..MEDICAL CONCEPTS INC.
0000              235 ..INIT. & BACKGROUND ROUTS. COPYRIGHT:23OCT78
0000              236 ..INIT.ROJT. :
0000  7160        237         DIS,DSTTME         ..X<- ADR
0002              238 ..MPC<- P.C.
F 0002 F80043     239         LDI A.0(INITLZ);PLO MPC
F 0005 F800B3D3   240         LDI A.1(INITLZ);PHI MPC;SEP MPC
0009              241 ..DISABLE INTERRUPTS AGAIN FOR TEST:
0009 E37163       242 INITLZ: SEX MPC;DIS,#63
000C              243 ..INIT.RFT
000C F901B0F800A0 244         LDI 1;PHI RFT;LDI 0;PLO RFT
0012 AE           245         PLO CLK      ..CLK<- 0
0013              246 ..INIT. SECOND COUNTER TO 60 SECONDS:
0013 F8EABE       247         LDI SECS60;PHI CLK
0016 F859B2       248         LDI A.1(STCKTP);PHI STK ..INIT STK
0019 F8FFA2       249         LDI A.0(STCKTP);PLO STK
001C              250 ..INIT. INTERRUPT ROUT. P.C.
F 001C F80081     251         LDI A.1(INTRPT);PHI IPC
F 001F F80041     252         LDI A.0(INTRPT);PLO IPC
F 0022 F8008F     253         LDI A.1(MSBGN);PHI FPC
F 0025 F800AF     254         LDI A.0(MSBGN);PLO FPC
0028              255 ..CLEAR MONITR'S QRS LEVEL DETECT STACK:
0028 F859B9       256         LDI A.1(LDSTKB);PHI LDSTKX
002B B5B6         257         PHI SRC;PHI DST
```

```
      0020 F800A9           258             LDI A.0(LOSTKB);PLO LOSTKX
      0030 F80059           259             LDI 0;STR LOSTKX
F     0033 F800B4           260             LDI A.1(MOVE);PHI CALL
F     0036 F800A4           261             LDI A.0(MOVE);PLO CALL
      0039 040001FF         262             SEP CALL,A.0(LOSTKB),A.0(LOSTKB+1),#FF
      003D                  263      ..(ALL REFERENCES BY CALL,SRC,DST,ADR TO BE
      003D                  264      ..ON THE SAME PAGE,ELIMINATING THE NEED TO
      003D                  265      ..REINIT. REG.1 AGAIN)
      003D                  266      ..CLEAR WORKSPACE :
      003D F85BB6           267             LDI A.1(UPDNCT);PHI ADR
      0040 B5B5             268             PHI SRC;PHI DST
      0042 F80DA656         269             LDI 0;PLO ADR;STR ADR
F     0046 F800A404         270             LDI A.0(MOVE);PLO CALL;SEP CALL
      0049 0001FE           271             ,A.0(UPDNCT),A.0(UPDNCT+1),#FE
      004D                  272      ..INIT T(N),OLDTIM STCK :
      004D F824A6           273             LDI A.0(OLDTIM-41);PLO ADR
      0050 F8E656           274             LDI 230;STR ADR
F     0053 F800A4           275             LDI A.0(MOVE);PLO CALL
      0056 04242628         276      SEP CALL,A.0(OLDTIM-41),A.0(OLDTIM-39),40
      005A F86FA6E6         277             LDI A.0(TCP105+1);PLO ADR;SEX ADR
      005E F8FF7373         278             LDI #FF;STXD;STXD         ..TCP105
      0062 F863A6           279             LDI A.0(ITPSHT+1);PLO ADR
      0065 F8FF73737373     280             LDI #FF;STXD;STXD;STXD;STXD ..ITPSHT,TCP
      006B F87EA6           281             LDI A.0(SAMECT);PLO ADR
      006E F8FF73           282             LDI #FF;STXD    ..SAMECT
      0071 F883A6           283             LDI A.0(SVSTKX);PLO ADR
      0074 F8FF73           284             LDI #FF;STXD    ..SVSTKX
      0077 F822A6           285             LDI A.0(MODCTL);PLO ADR
      007A F80856           286             LDI #08;STR ADR
      007D F8F7A6           287             LDI A.0(BEATNU);PLO ADR
      0080 F80273           288             LDI 2;STXD ..BEATNU
      0083 F889A6           289             LDI A.0(DIMTME+1);PLO ADR
      0086 F80173           290             LDI 1;STXD      ..DIMTME.1
      0089 F82C73           291             LDI #2C;STXD    ..DIMTME.0
      008C F803A6           292             LDI A.0(NARTSC);PLO ADR
      008F F83B56           293             LDI SECS15;STR ADR
      0092 F8DCA6           294             LDI A.0(STBLNK);PLO ADR
      0095 F81456           295             LDI 20;STR ADR
      0098 F8CDA6           296             LDI A.0(EKGCTR);PLO ADR
      009B F85A56           297             LDI 90;STR ADR  ..EKGCTR
      009E                  298      ..INIT.LNG,SHRT DELAY PNTRS:
      009E F8F4A6           299             LDI A.0(SHTSVR);PLO ADR
      00A1 F8EA56           300             LDI A.0(SHTBGN);STR ADR
      00A4 F8CBB8           301             LDI A.1(LNGBGN);PHI LNGX
      00A7                  302      ..INIT. CASSETTE PROGRAM COUNTER
F     00A7 F801AC           303             LDI A.0(NORECD+1);PLO CPC
F     00AA F808BC           304             LDI A.1(NORECD+1);PHI CPC
      00AD                  305      ..
      00AD                  306      ..INIT. DATA BUFFERS: FIRST ZERO THEM:
      00AD F85AB7           307             LDI A.1(DATBUF);PHI SUM
      00B0 F800A7           308             LDI A.0(DATBUF);PLO SUM
      00B3 F80057           309             LDI 0;STR SUM
      00B6 4757             310      DATIMV: LDA SUM;STR SUM
      00B8 87F3FF3AB5       311             GLO SUM;XRI A.0(DATBUF-1);BNZ DATIMV
      00BD                  312      ..MOVE MASKS TO BUFFER:
      00BD F800AD           313             LDI A.0(DATBUF);PLO DAT
      00C0 F85ABD           314             LDI A.1(DATBUF);PHI DAT
F     00C3 F800A8           315             LDI A.0(HDRMSK);PLO GR
F     00C6 F800B8           316             LDI A.1(HDRMSK);PHI GR
      00C9 48501D           317      DATMK1: LDA GR;STR DAT;INC DAT
      00CC 8DFB0B3AC9       318             GLO DAT;XRI A.0(PERIOD);BNZ DATMK1
      00D1 F880AD           319             LDI A.0(DATBUF+#80);PLO DAT
      00D4 F85ABD           320             LDI A.1(DATBUF+#80);PHI DAT
F     00D7 F800A8           321             LDI A.0(HDRMSK);PLO GR
F     00DA F800B8           322             LDI A.1(HDRMSK);PHI GR
      00DD 48501D           323      DATMK2: LDA GR;STR DAT;INC DAT
      00E0 8DFB8B3A0D       324             GLO DAT;XRI A.0(PERIOD+#80);BNZ DATMK2
      00E5                  325      ..SET PERIOD' TO 1
      00E5 F8015D           326             LDI 1;STR DAT
      00E8                  327      ..POINT DAT TO MINUTE
      00E8 F8CCAD           328             LDI A.0(MINUTE);PLO DAT
F     00EB C00000           329             LBR INITCA
      00EE                  330      ..................................
      0100                  331             PAGE
      0100                  332      ..INITIALIZE CASSETTE RECORDER:
      0100                  333      ..FIND BEGINING OF TAPE AND STOP:
      0100 F8C9A6           334      INITCA: LDI A.0(CASCTL);PLO DST
```

```
    0103 F81656         335         LDI STOP;STR DST
    0106 E66526         336         SEX DST;OUT CASOUT;DEC DST
    0109 7A             337         REQ  ..DATA<-OFF
    010A                338 ..WAIT FOR 150MS. CASSETTE PRESENCE
    010A F817A7         339         LDI #17;PHI SUM
    010D 3E00           340 WTPRCA: BN3 INITCA
    010F 27973A0D       341         DEC SUM;GHI SUM;BNZ WTPRCA
    0113                342 ..REWIND AND WAIT FOR 1 SEC CLR LEADER
    0113 F822566626     343         LDI REW;STR DST;OUT CASOUT;DEC DST
    0119 F877B7         344 WTCLR:  LDI A.1(KS1);PHI SUM
    011B F817A7         345         LDI A.0(KS1);PLO SUM
    011E 3E00           346 WTCLOP: BN3 INITCA ..WAIT CLEAR LOOP
    0120 3519           347         B2 WTCLR
    0122 27873A1E       348         DEC SUM;GLO SUM;BNZ WTCLOP
    0126 973A1E         349         GHI SUM;BNZ WTCLOP
    0129                350 ..STOP CASSETTE AND WAIT 150 MS.
    0129 F81656         351         LDI STOP;STR DST
    012C 6626           352         OUT CASOUT;DEC DST
    012E F817B7         353         LDI #17;PHI SUM
    0131 27973A31       354 STOPLP: DEC SUM;GHI SUM;BNZ STOPLP
    0135                355 ..FIND B.O.T.(WAIT NO CLR LDR)
    0135 F80F56         356 FINBOT: LDI WRITE;STR DST
    0138 6626           357         OUT CASOUT;DEC DST
    013A F817B7         358         LDI #17;PHI SUM
    013D 3E003035       359 FINCLP: BN3 INITCA;BN2 FINBOT
    0141 27973A3D       360         DEC SUM;GHI SUM;BNZ FINCLP
    0145 3E00           361         BN3 INITCA ..NO CASSETTE?
    0147 F81556         362         LDI STOPW;STR DST
    014A 6626           363         OUT CASOUT;DEC DST
    014C                364 ..
    014C                365 ..WAIT 150MS. CASSETTE<- OFF
    014C F817B8         366         LDI #17;PHI GR
    014F 28983A4F       367 BOTLP:  DEC GR;GHI GR;BNZ BOTLP
    0153 F81456         368         LDI OFF;STR DST
    0156 6626           369         OUT CASOUT;DEC DST
    0158                370 ..CASSETTE INITIALIZED
    0158                371 ..
    0158                372 ..........BACKGROUND ROUTINES: ............
    0158                373 ............................................
    0158                374 ..CHECK CASSETTE AND QUE
F   0158 F80A4DD        375 BACKGD: LDI A.0(CKCASQ);PLO CALL;SEP CALL
    015C                376 ..
    015C                377 ..
    015C                378 ..LOOSE ELECTRODES? :
    015C F800A5         379         LDI A.0(UPDNCT);PLO SRC
    015F F8F6A6         380         LDI A.0(OUTCTL);PLO DST
F   0162 05FF1C5B00     381         LDN SRC;SMI ONLECT;BM OFFLSE
    0167 F813A5E5       382 ONLSE:  LDI A.0(PPMREF);PLO SRC;SEX SRC
    016B F8007373       383         LDI 0;STXD;STXD ..CLEAR PPMREF
    016F 73737373       384         STXD;STXD;STXD;STXD
    0173 F822A5         385         LDI A.0(MODCTL);PLO SRC ..CLEAR RUNCTL
    0176 05FAEF55       386         LDN SRC;ANI #EF;STR SRC
    017A E37133         387         SEX MPC;DIS,MNEMNE
    017D 06F98056       388         LDN DST;ORI #80;STR DST
F   0181 3000           389         BR SETLSE
    0183                390 ..
    0183 E37133         391 OFFLSE: SEX MPC;DIS,MNEMNE
    0186 06FA7F56       392         LDN DST;ANI #7F;STR DST
    018A 706365         393 SETLSE: RET,DSTMNE;OUT OUTSIG
    018D                394 ..
    018D                395 ..
    018D                396 ..
    018D                397 ..
    018D                398 ..CHECK FOR RFT OVERFLOW(3 SECS)
F   018D 98F80C3A00     399         GHI RFT;XRI #0C;BNZ CKRFLG
    0192                400 ..RFT OVERFLOW!!!!
    0192 F81746         401 OFLART: LDI A.0(INBFWD);PLO DST
    0195 E37133         402         SEX MPC;DIS,MNEMNE
    0198 06F98056       403         LDN DST;ORI #80;STR DST ..SET AR3,H.L.
    019C F80DA0         404         LDI A.0(TWOSEC);PLO RFT
    019F F80780         405         LDI A.1(TWOSEC);PHI RFT ..REINIT
    01A2 F8F6A6         406         LDI A.0(OUTCTL);PLO DST ..PRE<- ON
    01A5                407 ..TOOBIG<- OFF;PRE4,AGCA<- ON
    01A5 06FAFDF92456   408         LDN DST;ANI #FD;ORI #24;STR DST
    01AB 308A           409         BR SETLSE
    01AD                410 ..
    01AD 3458           411 CKRFLG: B1 BACKGD   ..BNREF?(WAIT)
```

```
            01AF                412 ............................................
            01AF                413 ..CLEAR STARTUP OR VFIB MODES?
F   01AF  F80088                414         LDI A.1(NRMLSU);PHI GR
F   01B2  F800A4                415         LDI A.0(DETALG);PLO CALL
F   01B5  D41E00                416         SEP CALL,A.0(CODWDS-3),A.0(NRMLSU)
F   01B8  D41A00                417         SEP CALL,A.0(CODWDS-6),A.0(BIGMSU)
F   01BB  D41D00                418         SEP CALL,A.0(CODWDS-4),A.0(TRIGSU)
    01BE  F822A6                419 CLRVFB: LDI A.0(MODCTL);PLO DST ..Y,CLR VFIB
    01C1  05FA7F56              420         LDN DST;ANI #7F;STR DST
F   01C5  FA23A000              421         ANI #02;BNZ BKMON ..H.L.ART?
    01C9  F8F7A5                422         LDI A.0(BEATNU);PLO SRC
F   01CC  05FF203B00            423         LDN SRC;SMI 32;BNF BKMON
    01D1  05FAF756              424         LDN DST;ANI #F7;STR DST ..CLR STRT
    01D5                        425 ............................................
    01D5                        426 ..MONITR BACKGROUND PROCESSOR ROUTINE:
    01D5                        427 ..INIT LOSTKX,BEATBK
    01D5  F8F5A5                428 BKMON:  LDI A.0(REFADR);PLO SRC
    01D8  05A9                  429         LDN SRC;PLO LOSTKX
    01DA  F8F7A5                430         LDI A.0(BEATNU);PLO SRC
    01DD                        431 ..IF BEATNU >150,AND IN STARTUP
    01DD                        432 ..THEN SWITCH LEADS:
F   01DD  05FF963B00            433         LDN SRC;SMI 150;BM CONTBK
    01E2  F822A6                434         LDI A.0(MODCTL);PLO DST
F   01E5  05FA083200            435         LDN DST;ANI #08;BZ CONTBK
    01EA                        436 ..STARTUP! SWITCH LEADS:
    01EA  F8F6A6                437         LDI A.0(OUTCTL);PLO DST
    01ED  E37133                438         SEX NPC;DIS,MNEMNE
    01F0  05F94056              439         LDN DST;ORI #40;STR DST
    01F4  7063                  440         RET,DSTMNE
    01F6  F87FA6                441 CONTBK: LDI A.0(BEATBK);PLO DST
    01F9  05FF0156              442         LDN SRC;SMI 1;STR DST
    01FD                        443 ..BACKUP ONE BLOCK(TO ONSET OF REFRAC)
F   01FD  F800A4                444         LDI A.0(BACKUP);PLO CALL
F   0200  040000                445         SEP CALL,A(FRSTBK)
F   0203  3000                  446         BR PUTTLD
    0205                        447 ..TIME FOR 1ST BEAT = 230MS.
    0205  F800B7                448 FRSTBK: LDI A.1(REFRAC);PHI SUM
    0208  F8DCA7                449         LDI A.0(REFRAC);PLO SUM
    020B                        450 ..LOSTKX NOW POINTING TO REFRAC ONSET
    020B                        451 ..BLOCK LOCDE     TLD<-SUM
    020B  F87CA6                452 PUTTLD: LDI A.0(TLD);PLO DST
    020E  875616                453         GLO SJM;STR DST;INC DST
    0211  9756                  454         GHI SJM;STR DST
    0213                        455 ..SAVE SHIFTED REFRAC ONSET LOCDE:
    0213  F80DA6                456         LDI A.0(SETWID);PLO DST
    0216  09FA03FEFE56          457         LDN LOSTKX;ANI #03;SHL;SHL;STR DST
F   021C  F800A4                458         LDI A.0(BACKUP);PLO CALL
F   021F  040000                459         SEP CALL,A(TLLDNG)
    0222                        460 ..LOSTKX POINTING TO LLD REFRAC ONSET
    0222                        461 ..BLOCK  A(REFADB)<- LOSTKX
    0222  F880A6                462         LDI A.0(REFADB);PLO DST
    0225  8956                  463         GLO LOSTKX;STR DST
    0227                        464 ..LLD=SHR(2) HLD ?
    0227  F80DA5                465         LDI A.0(SETWID);PLO SRC
    022A  E9                    466         SEX LOSTKX
F   022B  05F33200              467         LDN SRC;XOR;BZ TLLDOK
    022F                        468 ..SET TLLD = TLD:
    022F  F87CA5                469 TLLDNG: LDI A.0(TLD);PLO SRC
    0232  45A74517              470         LDA SRC;PLO SUM;LDA SRC;PHI SUM
    0236                        471 ..TLLD <- SUM
    0236  F87AA6                472 TLLDOK: LDI A.0(TLLD);PLO DST
    0239  875616                473         GLO SJM;STR DST;INC DST
    023C  9756                  474         GHI SJM;STR DST
    023E                        475 ..OLDTIM<- SJM<- TLAG+TLLD
F   023E  F800A4                476         LDI A.0(CLRSUM);PLO CALL
    0241  047802                477         SEP CALL,A.0(TLAG),2
    0244  F84DA656              478         LDI A.0(OLDTIM);PLO DST;SEX DST
    0248  9773B773              479         GHI SJM;STXD;GLO SUM;STXD
    024C                        480 ..TLAG<- TLD-TLLD
    024C  F87CA5                481         LDI A.0(TLD);PLO SRC
    024F  F87AA656              482         LDI A.0(TLLD);PLO DST;SEX DST
    0253  45F7A716              483         LDA SRC;SM;PLO SUM;INC DST
    0257  057787                484         LDN SRC;SMB;PHI SUM
    025A  F878A6                485         LDI A.0(TLAG);PLO DST
    025D  875616                486         GLO SJM;STR DST;INC DST
    0260  9756                  487         GHI SJM;STR DST
    0262                        488 ..
```

```
      0262                489  ..
      0262                490  ..T(N) PREM,COMP.P.,OR INTERPOLATED?
      0262                491  ..(SCRSTK-1)<- OLDTIM*2
F     0262  F800A4        492  PPCPCK: LDI A.0(SHFTLT);PLO CALL
      0265  04405601      493          SEP CALL,A.0(OLDTIM-1),A.0(SCRSTK-1),1
      0269                494  ..(SCRSTK-1)<- OLDTIM*4
      0269  04555601      495          SEP CALL,A.0(SCRSTK-1),A.0(SCRSTK-1),1
      026D                496  ..(SCRSTK-3)<- OLDTIM*8
      026D  04555401      497          SEP CALL,A.0(SCRSTK-1),A.0(SCRSTK-3),1
      0271                498  ..(SCRSTK-3)<- OLDTIM*16
      0271  04545401      499          SEP CALL,A.0(SCRSTK-3),A.0(SCRSTK-3),1
      0275                500  ..(SCRSTK-5)<- OLDTIM*32
      0275  04545201      501          SEP CALL,A.0(SCRSTK-3),A.0(SCRSTK-5),1
      0279                502  ..SUM<- OLDTIM
F     0279  F800A4        503          LDI A.0(CLRSUM);PLO CALL
      027C  044C01        504          SEP CALL,A.0(OLDTIM-1),1
      027F                505  ..SUM<- OLDTIM*5
      027F  045501        506          SEP CALL,A.0(SCRSTK-1),1
      0282  F871A6F6      507          LDI A.0(OLDT5+1);PLO DST;SEX DST
      0286  97738773      508          GHI SJM;STXD;GLO SUM;STXD
      028A                509  ..SUM<- OLDTIM*6
      028A  044C01        510          SEP CALL,A.0(OLDTIM-1),1
      028D  F87346F6      511          LDI A.0(OLDT6+1);PLO DST;SEX DST
      0291  97738773      512          GHI SJM;STXD;GLO SUM;STXD
      0295                513  ..SUM<- OLDTIM*10
      0295  045501        514          SEP CALL,A.0(SCRSTK-1),1
      0298  F87546F6      515          LDI A.0(OLDT10+1);PLO DST;SEX DST
      029C  97738773      516          GHI SJM;STXD;GLO SUM;STXD
      02A0                517  ..
      02A0                518  ..
      02A0                519  ..SUM>+=TCP11?;SET COMP.P.
F     02A0  F800A404      520          LDI A.0(COMPBR);PLO CALL;SEP CALL
FM    02A4  6000000000000 521          ,A.0(TCP11),A(ITPCHK),A(STCOMP),A(STCOMP)
      02A8                522  ..SET COMP.PAUSE:
      02A8  F82146        523  STCOMP: LDI A.0(CODWDS);PLO DST
      02AB  06F90256      524          LDN DST;ORI #02;STR DST
      02B2                525  ..IF O_OTIM>210%,SET ART
      02B2                526  ..SUM<- OLDT5
      02B2  F870A5        527          LDI A.0(OLDT5);PLO SRC
      02B5  45A70547      528          LDA SRC;PLO SUM;LDN SRC;PHI SUM
      02B9                529  ..OLDT5< = >TCP105?
F     02B9  F800A404      530          LDI A.0(COMPBR);PLO CALL;SEP CALL
FM    02BD  6E00000000000 531  ,A.0(TCP105),A(CHK180),A(TOOLNG),A(TOOLNG)
      02C4                532  ..
      02C4                533  ..DISABLE LONG R-R ARTIFACTS FOR
      02C4                534  ..REPETITIOUS TOO LONG R-R
      02C4  F88145        535  TOOLNG: LDI A.0(TOLGCT);PLO SRC
F     02C7  05C20000      536          LDN SRC;LBZ SDROUT   ..YES(SET NO ART)
      02CB  FF0155        537          SMI 1;STR SRC
      02CE                538  ..DISABLE DURING U.R..START,RUNCTL:
K     02CE  F322          539  LRRART: LDI A.0(MODCTL);PLO DST
F     02D0  05FA38CA0000  540          LDN DST;ANI #38;LBNZ SDROUT
      02D6  F817A6        541          LDI A.0(INBFWD);PLO DST
      02D9  E37133        542          SEX MPC;DIS,MNEMNE
      02DC  06F90255      543          LDN DST;ORI #02;STR DST ..ART2
F     02E0  7053C00000    544          RET,DSTMNE;LBR SDROUT
      02E5                545  ..
      02E5                546  ..SUM<- OLDT6
      02E5  F872A5        547  CHK180: LDI A.0(OLDT6);PLO SRC
      02E8  45A70547      548          LDA SRC;PLO SUM;LDN SRC;PHI SUM
      02EC                549  ..OLDT6 < = > TCP11 ?
F     02EC  F800A404      550          LDI A.0(COMPBR);PLO CALL;SEP CALL
FM    02F0  6000000000000 551  ,A.0(TCP11),A(SDROUT),A(LTHPVC),A(LTHPVC)
      02F7                552  ..**************************************
      02F7                553  ..LOW THRESHOLD PVC ROUTTINE:
      02F7                554  ..LOST<X STILL POINTING TO LLD REFRAC ONSET
      02F7                555  ..PRESET BACKJP CTR TO -MAX.# BACKUPS TOLERATED
      02F7  F882A6        556  LTHPVC: LDI A.0(BKUPCT);PLO DST
      02FA  F8EC56        557          LDI LTHRBK;STR DST
F     02FD  F800A4        558  LTHRLP: LDI A.0(BACKUP);PLO CALL
F     0300  040000        559          SEP CALL,A(SDROUT)
      0303  F882A6        560          LDI A.0(BKUPCT);PLO DST   ..INCR ITER CTR
      0306  06FC0156      561          LDN DST;ADI 1;STR DST
F     030A  C20000        562          LBZ SDROUT ..TOO MANY ITER. ?
      030D  F876A6        563          LDI A.0(LTHTME);PLO DST   ..SAVE LTHTME
      0310  875616        564          GLO SJM;STR DST;INC DST
      0313  9756          565          GHI SUM;STR DST
      0315                566  ..COMPUTE LTHTME*32
```

```
       0315             567 ..(SCRSTK-1)<- LTHTME*2
F      0315  F800A4      568         LDI A.0(SHFTLT);PLO CALL
       0318  04755601    569         SEP CALL,A.0(LTHTME),A.0(SCRSTK-1),1
       031C             570 ..(SCRSTK-1)<- LTHTME*32
       031C  F804A7      571         LDI 4;PLO SUM
       031F  04555601    572 LTH32L: SEP CALL,A.0(SCRSTK-1),A.0(SCRSTK-1),1
       0323  27873A1F    573         DEC SUM;GLO SUM;BNZ LTH32L
       0327             574 ..SUM<- LTHTME*32
       0327  F855A6      575         LDI A.0(SCRSTK-1);PLO DST
       032A  46A706A7    576         LDA DST;PLO SUM;LDN DST;PHI SUM
       032D             577 ..LTHTME*32 < = > TP32 ?
       032D             578 ..(IF PREM,IS IT ALSO < REFRAC? ELSE CONTINUE
F      032D  F800A404    579         LDI A.0(COMPBR);PLO CALL;SEP CALL
FF     0332  6A0000000002FD 580       ,A.0(TP32),A(LREFCK),A(LREFCK),A(LTHRLP)
       0339             581 ..
       0339             582 ..
       0339             583 ..NO LTHR PVC,DROPPED IF RUNCTL.H.L.A..START
       0339  F822A5      584 LREFCK: LDI A.0(MODCTL);PLO SRC
F      033C  45FA1ACA0000 585         LDA SRC;ANI #1A;LBNZ SDROUT
       0342             586 ..MO2CTL (#02 = MOPH.STRETCH ARTS)
F      0342  05FA02CA0000 587         LDN SRC;ANI #02;LBNZ SDROUT
       0348             588 .. , OR IF RJNS
       0348  F8C3A5      589         LDI A.0(OUTIND);PLO SRC
F      034B  05FA10CA0000 590         LDN SRC;ANI #10;LBNZ SDROUT
       0351  F8DEA6      591         LDI A.0(OUTMSK);PLO DST
       0354             592 ..IS PREM LTHTME ALSO > REFRAC?
       0354  F877A5      593         LDI A.0(LTHTME+1);PLO SRC  ..CK HI BYTE
F      0357  053A00      594         LDN SRC;BNZ LTHSET  ..YES,LTHPVC!
F      035A  2505FFDC3300 595         DEC SRC;LDN SRC;SMI REFRAC;BPZ LTHSET
       0360             596 ..NO DROPPED BEATS IN U.R.
       0360  F822A5      597         LDI A.0(MODCTL);PLO SRC ..U.R.?
F      0363  05FA20CA0000 598         LDN SRC;ANI #20;LBNZ SDROUT
       0369             599 ..NOT LTHR PVC,DROPPED BEAT!
       0369  06F98056    600         LDN DST;ORI #80;STR DST ..DROPPED!
F      036D  3000        601         BR MBTMFX
       036F             602 ..
       036F             603 ..MARK OCCURRENCE OF LTHR PVC!
       036F  06F90856    604 LTHSET: LDN DST;ORI #08;STR DST
       0373             605 ..MISSED BEAT TIMING FIX:
       0373             606 ..OLDTIM<- OLDTIM/2
F      0373  F800A4      607 MBTMFX: LDI A.0(SHFTRT);PLO CALL
       0376  04C4C401    608         SEP CALL,A.0(OLDTIM-1),A.0(OLDTIM-1),1
F      037A  C00000      609         LBR SDROUT
       037D             610 ..
       037D             611 ..
       037D             612 ..IF UPDNCT>50%,DISABLE PREM'S:
       037D  F800A5      613 ITPCHK: LDI A.0(UPDNCT);PLO SRC
F      0380  05FF33C30000 614         LDN SRC;SMI SEXCT;LBDF SDROUT
       0386             615 ..IF STARTUP MODE,DISABLE PREMS:
       0386  F822A5      616         LDI A.0(MODCTL);PLO SRC
F      0389  05FA08CA0000 617         LDN SRC;ANI #08;LBNZ SDROUT
       038F             618 ..INTERPOLATED BEAT CHECK:
       038F  0462        619         SEP CALL,A.0(ITPSHT)
FM     0391  000000000000 620         ,A(PREMCK),A(ITLGCK),A(ITLGCK)
       0397  0464        621 ITLGCK: SEP CALL,A.0(ITPLNG)
FM     0399  000000000000 622         ,A(STITPD),A(STITPD),A(PREMCK)
       039F             623 ..
       039F             624 ..SET INTERPOLATED:
       039F  F821A6      625 STITPD: LDI A.0(CODWDS);PLO DST
       03A2  06F92156    626         LDN DST;ORI #21;STR DST
       03A5             627 ..
       03A5             628 ..PREMATURE CHECK: SUM<- OLDTIM*32
       03A5  F852A5      629 PREMCK: LDI A.0(SCRSTK-5);PLO SRC
       03A8  45A74587    630         LDA SRC;PLO SUM;LDA SRC;PHI SUM
       03AD             631 ..IF UNSTABLE RHYTHYM USE TCP27 FOR PREM
       03AD  F8BEA5      632         LDI A.0(STABCT);PLO SRC
F      03B0  05FF0F3300  633         LDN SRC;SMI MEDSTB;BPZ CKLGPR
       0385  D46A        634         SEP CALL,A.0(TP32)
FM     03B7  000000000000 635         ,A(SJPRCK),A(SJPRCK),A(CKMCHG)
       03BD             636 ..
       03BD             637 ..PREM! ALSO SUPREM (78%) ? :
       03BD             638 ..SUM<-OLDTIM*36
F      03BD  F800A4      639 SUPRCK: LDI A.0(STKSUM);PLO CALL
       03C0  045501      640         SEP CALL,A.0(SCRSTK-1),1  ..**4
F      03C3  F800A4      641         LDI A.0(COMPBR);PLO CALL
       03C6  D46A        642         SEP CALL,A.0(TP32)
FM     03C8  000000000000 643         ,A(SJPRST),A(SJPRST),A(STPREM)
```

```
       03CE                            644 ..
       03CE                            645 ..IF T(N-1) MORPH. CHANGE,PREM. USE TCP27:
       03CE F82046                     646 CKMCHG: LDI A.0(CODWDS-1);PLO DST
F      03D1 05FA0CC20000               647         LDN DST;ANI #9C;LBZ SDROUT
F      03D7 05FA01C20000               648         LDN DST;ANI #01;LBZ SDROUT
       03DD                            649 ..(SUM=OLDTIM*32,CALL=COMPBR)
       03DD D468                       650 CKLGP0: SEP CALL,A.0(TCP27)
F      03DF 03B003B00000               651         ,A(SJPRCK),A(SJPRCK),A(SDROUT)
       03E5                            652 ..
       03E5                            653 ..MARK SUPRA PREM (78%) :
       03E5 F807A6                     654 SUPRST: LDI A.0(MRKPRM);PLO DST
       03E8 05F90156                   655         LDN DST;ORI #01;STR DST
       03EC                            656 ..SET PREMATURE
       03EC F821A6                     657 STPREM: LDI A.0(CODWDS);PLO DST
       03EF 05F90156                   658         LDN DST;ORI #01;STR DST
       03F3                            659 ..........................................
       03F3                            660 ..
       03F3                            661 ..DO SPECTR.DELTA ROUT. AFTER 220MS. :
       03F3 F885A6                     662 SDROUT: LDI A.0(SDTME);PLO DST
       03F6 E37133                     663         SEX MPC;DIS,MNEMNE
       03F9 8055                       664         GLO RFT;STR DST
       03FB 169056                     665         INC DST;GHI RFT;STR DST
       03FE 7063                       666         RET,DSTMNE
       0400                            667 ..
       0400                            668 ..
       0400                            669 ..CHECK CASSETTE AND QUE:
F      0400 F80D4404                   670 WTREFR: LDI A.0(CKCASQ);PLO CALL;SEP CALL
       0404 3C00                       671         BN1 WTREFR ..BREF(WAIT)
       0406                            672 ..
       0406                            673 ..
       0406                            674 ..
       0406                            675 ..SPECTR.DELTA ROUT. :
       0406 F821A6                     676         LDI A.0(CODWDS);PLO DST
       0409 F818A5                     677         LDI A.0(INPDAT);PLO SRC
       040C                            678 ..S.D.=LFINC+NOTLFDEC+NOTHFDEC
       040C 05FA30FA3B                 679         LDN SRC;XRI #30;ANI #3B
F      0411 3200                       680         BZ PKDIFF
       0413 05F91056                   681         LDN DST;ORI #10;STR DST  ..SET SP.DELTA
       0417                            682 ..IF LFINC=1,HFINC<- 0
F      0417 05FA083200                 683         LDN SRC;ANI #08;BZ PKDIFF
       041C 05FAF055                   684         LDN SRC;ANI #F0;STR SRC
       0420                            685 ..
       0420                            686 ..
       0420                            687 ..PEAK DIFF. ROUT.:
       0420 05FA44FA44                 688 PKDIFF: LDN SRC;XRI #44;ANI #44
F      0425 3200                       689         BZ PTAWID
       0427 05F98056                   690         LDN DST;ORI #80;STR DST  ..SET PKDIFF.
       042B                            691 ..
       042B                            692 ..
       042B                            693 ..
       042B                            694 ..
       042B                            695 ..PULSE TIMING,QRS WIDTH ROUT.:
       042B                            696 ..
       042B                            697 ..PLDMRK,PNLOCT<- 0
       042B F815A6E6                   698 PTAWID: LDI A.0(PLDMRK);PLO DST;SEX DST
       042F F8007373                   699         LDI 0;STXD;STXD
       0433                            700 ..POINT LDSTKX TO LLD REFRAC ONSET:
       0433 F80AA5                     701         LDI A.0(REFADB);PLO SRC
       0436 05A9                       702         LDN SRC;PLO LDSTKX
       0438                            703 ..CHECK ONSET BLOCK(BEATNO) FOR INTERRUPT
       0438                            704 ..WRAP AROUND OBLITERATING DATA
F      0438 F80DA4                     705         LDI A.0(FORWRD);PLO CALL
F      043B D40D00                     706         SEP CALL,A(ZERWID)
       043E                            707 ..POINTING TO LD REFRAC ONSET.
       043E                            708 ..INCR BEATBK:
       043E F87FA6                     709         LDI A.0(BEATBK);PLO DST
       0441 05FC0156                   710         LDN DST;ADI 1;STR DST
F      0445 3000                       711         BR PTPLD
       0447                            712 ..
F      0447 F80CA4                     713 PTWDLP: LDI A.0(FORWRD);PLO CALL
F      044A D40D00                     714         SEP CALL,A(ENDPTW)
       044D                            715 ..TIME<REFRAC ?
F      044D 97CA0000                   716         GHI SUM;LBNZ ENDPTW  ..NO
F      0451 87FFDCC30000               717         GLO SUM;SMI REFRAC;LBDF ENDPTW  ..NO
       0457                            718 ..POINT DST TO PLDMRK:
       0457 F815A6E6                   719 PTPLD:  LDI A.0(PLDMRK);PLO DST;SEX DST
       045B                            720 ..YES(<REFRAC),PLD OR NLD = 1?
```

```
F  045B  09FA033200        721          LDN LDSTKX;ANI #03;BZ HLDZER
   045D                    722  ..HLD=1  PLD? :
F  046D  FA023200          723          ANI #02;BZ SHFTMK
   0464                    724  ..YES,MARK PLDCDE:
   0464  06F98056          725          LDN DST;ORI #80;STR DST
   0469  06F673            726  SHFTMK: LDN DST;SHR;STXD  ..SHIFT PLDCDE
   046D  06FC0173          727          LDN DST;ADI 1;STXD  ..INC PNLDCT
   046F                    728  ..SHR(2)LDCDE -> SETWID
   046F  F80DA6            729          LDI A.0(SETWID);PLO DST
   0472  09FA3FEFE56       730          LDN LDSTKX;ANI #03;SHL;SHL;STR DST
   0478  3047              731          BR PTWDLP ..CONTINUE
   047A                    732  ..
   047A                    733  ..
   047A  F80DA6            734  HLDZER: LDI A.0(SETWID);PLO DST
   047D  063247            735          LDN DST;BZ PTWDLP
   0480  09F33247          736          LDN LDSTKX;XOR;BZ PTWDLP
   0484  F80073            737          LDI 0;STXD  ..SETWID<- 0
   0487  8756              738          GLO SUM;STR DST  ..STORE QRSWID
   0489  3047              739          BR PTWDLP
   048B                    740  ..
   048B                    741  ..
   048B                    742  ..QRS WIDTH<- 0 (ERROR)
   048B  F80CA6            743  ZERWID: LDI A.0(QRSWID);PLO DST
   048E  F80056            744          LDI 0;STR DST
   0491                    745  ..DISABLE PDM:
   0491  F87EA6            746          LDI A.0(SAMECT);PLO DST
   0494  F80F56            747          LDI #0F;STR DST
F  0497  3000              748          BR ADAROT
   0499                    749  ..
   0499                    750  ..DONE PROCESSING LD BLOCKS!
   0499                    751  ..QRSWID<- QRSWID+TLAG
   0499  F87BA5E5          752  ENDPTW: LDI A.0(TLAG);PLO SRC;SEX SRC
   049D  06F456            753          LDN DST;ADD;STR DST
   04A0                    754  ..............................
   04A0                    755  ..A/D CONVERTER ARTIFACTS ROUTINE:
   04A0                    756  ..CLEAR WIDE ARTIFACTS INHIBIT CTR.
   04A0  F8C6A6            757  ADAROT: LDI A.0(WIDAIN);PLO DST
   04A3  F800568747        758          LDI 0;STR DST;PHI SUM;PLO SUM
   04A8                    759  ..POINT GR TO ANALOG DELAY BUFFER
   04A8  F8C1A5            760          LDI A.0(BKLNGX);PLO SRC
   04AB  45A805B8          761          LDA SRC;PLO GR;LDN SRC;PHI GR
   04AF  F8C5A5            762          LDI A.0(ADANEW);PLO SRC
F  04B2  98FB603A00        763          GHI GR;XRI A.1(LNGEND+1);BNZ ADAWR1
   04B7  F85CB8            764          LDI A.1(LNGBGN);PHI GR
   04BA  F800A8            765          LDI A.0(LNGBGN);PLO GR
   04BD  4855              766  ADAWR1: LDA GR;STR SRC  ..ADANEW<-T(0)
F  04BF  98FB603A00        767  ADALP1: GHI GR;XRI A.1(LNGEND+1);BNZ ADAWR2
   04C4  F85CB8            768          LDI A.1(LNGBGN);PHI GR
   04C7  F800A8            769          LDI A.0(LNGBGN);PLO GR
   04CA  F8C4A6            770  ADAWR2: LDI A.0(ADAOLD);PLO DST
   04CD  0556              771          LDN SRC;STR DST  ..ADAOLD<-ADANEW
   04CF                    772  ..DIGITAL FILTER T(N)-->ADANEW
   04CF  E5                773          SEX SRC
   04D0  48F47655          774          LDA GR;ADD;SHRC;STR SRC
   04D4  17                775          INC SUM  ..INCR CELL CTR.
F  04D5  87FB1DC20000      776          GLO SUM;XRI 29;LBZ ARTROT ..DONE?
   04DB                    777  ..ADAOLD-ADANEW:
F  04DB  E6D5F7CB0000      778          SEX DST;LDN SRC;SM;LBNF NEGGY
   04E1                    779  ..DOES DIFFERENCE EXCEED ARTIFACT THRESHOLD?
   04E1  FF07CB04BF        780          SMI 7;LBNF ADALP1 ..NO,CONTINUE
   04E6                    781  ..EXCEEDS POSITIVE THRESHOLD! CHANGE?
F  04E6  97FA80CA0000      782  POSTHR: GHI SUM;ANI #80;LBNZ CKWIDI
   04EC  97FC01            783          GHI SUM;ADI 1 ..YES,COUNT
   04EF  FA3FF980B7        784          ANI #3F;ORI #80;PHI SUM ..MARK+
   04F4                    785  ..
   04F4                    786  ..HOW MANY CROSSINGS?
F  04F4  97FA3FFB03C20000  787  CKADA: GHI SUM;ANI #3F;XRI #03;LBZ ADATRE
F  04FC  FB03FB043200      788          XRI #03;XRI #04;BZ ADAFOR
F  0502  FB04FB053200      789          XRI #04;XRI #05;BZ ADAFIV
F  0508  FB05FB063200      790          XRI #05;XRI #06;BZ ADAART ..NEVER!
F  050E  3000              791          BR CKALTE ..CHECK LATE
   0510                    792  ..
   0510                    793  ..MARK CELL PAIR BELOW ARTIFACT THRESHOLDS:
   0510  97FA3FB7C004BF    794  CLRADA: GHI SUM;ANI #3F;PHI SUM;LBR ADALP1
   0517                    795  ..
   0517  FF01              796  NEGGY: SMI 1 ..TWO'S COMPLIMENT
   0519                    797  ..DOES DIFFERENCE EXCEED ARTIFACTS(-)?
```

```
       0519 FC05C304BF          798           ADI 5;LBDF ADALP1 ..NO,CONTINUE
F      051E 97FA403A00          799 NEGTHR: GHI SJM;ANI #40;BNZ CKALTE ..YES;CHANGE?
       0523                     800 ..COUNT & MARK CELL PAIR AS (-):
       0523 97FC01              801           GHI SJM;ADI 1
       0526 FA3FF94087C004F4    802           ANI #3F;ORI #40;PHI SUM;LBR CKADA
       052F                     803 ..
F      052E 87FF043B00          804 ADATRE: GLO SJM;SMI 4;B4 ADAART
F      0533 3000                805           BR CKALTE
       0535                     806 ..
F      0535 87FF063B00          807 ADAFOR: GLO SJM;SMI 6;B4 ADAART
F      053A 3000                808           BR CKALTE
       053C                     809 ..
F      053C 87FF123B00          810 ADAFIV: GLO SJM;SMI 18;B4 ADAART
       0541                     811 ..
       0541                     812 ..A/D CONVERTER ARTIFACTS LATE:
       0541 97FA5FFF03CB04BF    813 CKALTE: GHI SJM;ANI #3F;SMI 3;LBNF ADALP1
       0549                     814 ..IS CELL COUNT .GT. 16?
       0549 87FF10CB04BF        815           GLO SJM;SMI 16;LBNF ADALP1
       054F F80FA6              816 LTEART: LDI A.0(LTEBTS);PLO DST
       0552 06F90156            817           LDN DST;ORI #01;STR DST
       0556 C004BF              818           LBR ADALP1
       0559                     819 ..
       0559                     820 ..SET ARTIFACTS ON:
       0559 F81BA6              821 ADAART: LDI A.0(INPDAT);PLO DST
       055C 06F90256            822           LDN DST;ORI #02;STR DST ..ART2
       0560 C00541              823           LBR CKALTE
       0563                     824 ..
       0563                     825 ..CHECK WIDE INHIBIT:
       0563 F8C6A6              826 CKWIDI: LDI A.0(WIDAIN);PLO DST
       0566 06FC0156            827           LDN DST;ADI 1;STR DST
       056A FB053A41            828           XRI 5;BNZ CKALTE
       056E                     829 ..INHIBIT(WIDE)
       056E F822A6              830 INHWID: LDI A.0(MODCTL);PLO DST
       0571 06F94056            831           LDN DST;ORI #40;STR DST
F      0575 3000                832           BR ARTROT
       0577                     833 ......................................
       0577                     834 ..
       0577                     835 ..
       0577                     836 ..ARTIFACTS ROUT.:
I      0577 E36000              837 ARTROT: SEX MPC;OUT MODPRT,0 ..CLEAR MODPRT
       057A                     838 ..        *******
       057A F858B8              839           LDI A.1(MODCTL);PHI GR
       057D F822A8              840           LDI A.0(MODCTL);PLO GR ..GR<-A(MODCTL)
       0580 F8BDA6              841           LDI A.0(ARTBAG);PLO DST
       0583 06F636              842           LDN DST;SHR;STR DST ..DECR ARTBAG
       0586 F819A5              843           LDI A.0(INPDAT);PLO SRC
       0589 05A7                844           LDN SRC;PLO SUM ..SUM.0<- INPDAT
F      058B FA833200            845           ANI #83;BZ SKIPBT ..NO NEW ART?
       058F                     846 ..OTHER ARTS! INHIBIT LATE ART. INHIBIT:
       058F F8E0A5              847           LDI A.0(ARTBTS);PLO SRC
       0592 06F9FF55            848           LDN SRC;ORI #FF;STR SRC
       0596                     849 ..CHECK LATE ARTIFACTS:
F      0596 05FA403A00          850 SKIPBT: LDN SR;ANI #40;BNZ CONTAR ..LTE.I.?
       059B F80FA5              851           LDI A.0(LTEBTS);PLO SRC
F      059E 05FA013200          852           LDN SRC;ANI #01;BZ CONTAR
       05A3                     853 ..LATE ARTIFACTS!
       05A3 87F902A7            854           GLO SUM;ORI #02;PLO SUM
       05A7 F801A5B7            855 CONTAR: LDI A.0(ARTFAG);PLO SRC;GLO SUM
F      05AB FA833200            856           ANI #83;BZ CKACTR ..NO NEW ARTS?
F      05AF FA823200            857 WHICHA: ANI #82;BZ SETLL ..HL OR LL?
       05B3                     858 ..RJNCTL<- OFF,HL<- ON :
       05B3 05FAEFF90258        859 SETHL: LDN GR;ANI #EF;ORI #02;STR GR
       05B9 05F9015B            860 SETLL: LDN GR;ORI #01;STR GR ..LL<- ON
F      05BD 87FA813200          861           GLO SJM;ANI #81;BZ START2 ..ART2 ONLY?
       05C2 F83F55F80756        862           LDI #3F;STR SRC;LDI #07;STR DST ..ART3
       05C8 05F90F55            863 START2: LDN SRC;ORI #0F;STR SRC ..ARTFAG<- 2
       05CC 06F90356            864           LDN DST;ORI #03;STR DST ..ARTBAG<- 2
F      05D0 053A00              865 CKACTR: LDN SRC;BNZ LDALGA ..ARTFAG=0?
F      05D3 063A00              866           LDN DST;BNZ LDALGA ..ARTBAG=0?
       05D6 F8F6A5              867           LDI A.0(OJTCTL);PLO SRC ..LSE=0?
F      05D9 05FA803A00          868           LDN SRC;ANI #80;BNZ LDALGA
       05DE 26                  869           DEC DST ..DST<- A(ALGART)
F      05DF 05C20000            870           LDN DST;LBZ CLRART ..ALGART=0?
F      05E3 F656C00000          871           SHR;STR DST;LBR WQRSRT ..COUNT DOWN
       05EB                     872 ..
       05EB                     873 ..
       05EB 26                  874 LDALGA: DEC DST ..DST<- A(ALGART)
```

```
F   05E9  87FA01320J      874            GLO SJM;ANI #01;BZ OROF
    05EF  F8FF56          875            LDI #FF;STR DST ..8 MORE BEATS
    05F1  06F90F56        876  OROF:     LDN DST;ORI #0F;STR DST .. > 4 BEATS
F   05F5  3000            877            BR WQRSRT
    05F7                  878  ..
    05F7  F822A8          879  CLRART:   LDI A.0(MODCTL);PLO GR
    05FA  08FAFC5B        880            LDN GR;ANI #FC;STR GR
    05FE                  881  ........................................
    05FE                  882  ..FIRST RESET TOLGCT IF NO COMPP:
    05FE  F82145          883  WQRSRT:   LDI A.0(CODWDS);PLO SRC
F   0601  05FA023A00      884            LDN SRC;ANI #02;BNZ DOWQRS
    0605  F881A6F80356    885            LDI A.0(TOLGCT);PLO DST;LDI 3;STR DST
    060C                  886  ..
    060C                  887  ..NO WQRS ON SINGLE QRS LEVEL DETECT!
    060C  F814A5          888  DOWQRS:   LDI A.0(PNLDCT);PLO SRC
F   060F  05F801C20000    889            LDN SRC;XRI #01;LBZ PPMRT
    0615  F801A5E5        890            LDI A.0(WQRSTK-10);PLO SRC;SEX SRC
    0619  F800B7A7        891            LDI 0;PHI SUM;PLO SUM
    061D  1585FB0C        892  NQRSLP:   INC SRC;GLO SRC;XRI A.0(WQRSTK+1)
F   0621  3200            893            BZ CALWQR
FF  0623  97F7380032D0    894            GHI SUM;SM;BM BIGQRS;BZ MEDQRS
    0629  87F7331D        895            GLO SUM;SM;BPZ NQRSLP
    062D  05A7301D        896  MEDQRS:   LDN SRC;PLO SUM;BR NQRSLP
    0631                  897  ..
    0631  97A70587        898  BIGQRS:   GHI SJM;PLO SUM;LDN SRC;PHI SUM
    0635  301D            899            BR NQRSLP
    0637                  900  ..
    0637  F80CA5          901  CALWQR:   LDI A.0(QRSWID);PLO SRC
    063A  F821A6          902            LDI A.0(CODWDS);PLO DST ..WIDE? :
F   063D  87FC0AF73300    903            GLO SUM;ADI 10;SM;BPZ UPDTWQ
    0643  06F90856        904            LDN DST;ORI #08;STR DST ..FLAG WQRS
    0647                  905  ..
F   0647  06FA91CA0000    906  UPDTWQ:   LDN DST;ANI #91;LBNZ PPMRT ..PREM,M.CHG.
    064D  F82245          907            LDI A.0(MODCTL);PLO SRC ..RUNCTL?,ART?
F   0650  05FA133A00      908            LDN SRC;ANI #13;BNZ PPMRT
F   0655  F800A4          909            LDI A.0(MOVE);PLO CALL
    0658  D403020A        910            SEP CALL,A.0(WQRSTK-8),A.0(WQRSTK-9),10
    065C                  911  ........................................
    065C                  912  ..PULSE POSITION MORPHOLOGY ROUT.:
    065C  F87FA6          913  PPMRT:    LDI A.0(SAMECT);PLO DST
    065F  F821A8          914            LDI A.0(CODWDS);PLO GR
    0662  F85B88          915            LDI A.1(CODWDS);PHI GR
    0665  F814A5          916            LDI A.0(PNLDCT);PLO SRC ..SUM<-T(N)
    0668  45A74587        917            LDA SRC;PLO SUM;LDA SRC;PHI SUM
    066C  F800A4          918            LDI A.0(COMPBR);PLO CALL
    066F  D4              919  PPMCK2:   SEP CALL
FM  0670  1000D000000000  920            ,A.0(PPMREF-3),A(PPMCK3),A(PPNRML),A(PPMCK3)
    0677  D4              921  PPMCK3:   SEP CALL
FM  0678  12000000000000  922            ,A.0(PPMREF-1),A(PPMNEW),A(PPNRML),A(PPMNEW)
    067F                  923  ..
F   067F  08FA80DCA0000   924  PPNRML:   LDN GR;ANI #80;LBNZ VFIBBK ..M.CHNG.?
F   0685  06F656C00000    925            LDN DST;SHR;STR DST;LBR VFIBBK
    068B                  926  ..
    068B  F80F56          927  PUSHNL:   LDI #0F;STR DST
    068E                  928  ..IF RJNS,ARTS,STARTUP INHIBIT PUSHING NORMALS
    068E  F822A5          929            LDI A.0(MODCTL);PLO SRC
F   0691  05FA1BCA0000    930            LDN SRC;ANI #1B;LBNZ VFIBBK
F   0697  F800A4          931            LDI A.0(MOVE);PLO CALL
    069A  D4100E06        932            SEP CALL,A.0(PPMREF-3),A.0(PPMREF-5),6
F   069E  C00000          933            LBR VFIBBK
    06A1                  934  ..
    06A1  08FA80D328B     935  PPMNEW:   LDN GR;ANI #80;BZ PUSHNL
F   06A5  05CA0000        936            LDN DST;LBNZ VFIBBK
    06AA  08F90458        937            LDN GR;ORI #04;STR GR ..PPM<- 1
    06AE                  938  ........................................
    06AE                  939  ..VFIB BACKGROUND ROUTINE:
    06AE  F823A5          940  VFIBBK:   LDI A.0(MO2CTL);PLO SRC
    06B1  F822A6          941            LDI A.0(MODCTL);PLO DST
F   06B4  05FA803200      942            LDN SRC;ANI #80;BZ CKVFBT ..VF REQ.?
F   06B9  06FA023200      943            LDN DST;ANI #02;BZ CKVFVF ..H.L.ART?
F   06BE  05FA403200      944            LDN SRC;ANI #40;BZ CKVFBT ..VF INH.?
    06C3  06F98056        945            LDN DST;ORI #80;STR DST ..VFC<-ON
F   06C7  3000            946            BR CKVFBT ..CONTINUE
    06C9                  947  ..
    06C9                  948  ..NO VFIB INHIBIT FOR VF,RUNCTL,H.L.ART MODES:
F   06C9  05FA923A00      949  CKVFVF:   LDN DST;ANI #92;BNZ CKVFBT
    06CE                  950  ..NO VFIB INHIBIT IF MOPH.CHNG.
```

```
  06CE F821A6         952       LDI A.0(CODWDS);PLO DST
F 06D1 05FA9C3A00    953       LDN DST;ANI #9C;BNZ CKVFBT
  06D6               954 ..COUNT UP VFIB INHIBIT CTR.(MAX=10)
  06D6 F8E6A6        955       LDI A.0(VFICTR);PLO DST
F 06D9 05FF0A3300    956       LDN DST;SMI 10;BPZ CKVFBT
  06DE FC0B56        957       ADI 11;STR DST
  06E1               958 ..IF BEATBK = 0,DECR VFICTR (EVERY 256 BEATS)
  06E1 F87FA6        959 CKVFBT: LDI A.0(BEATBK);PLO DST
F 06E4 053A00        960       LDN DST;BNZ VFITST
  06E7 F8E6A6        961       LDI A.0(VFICTR);PLO DST
F 06EA 053200        962       LDN DST;BZ VFITST
  06ED FF0156        963       SMI 1;STR DST
  06F0 F8E6A6        964 VFITST: LDI A.0(VFICTR);PLO DST
F 06F3 05FF353300    965       LDN DST;SMI 5;BPZ SETVFI
  06F8               966 ..CLEAR VFIB INHIBIT,VFIB REQUEST:
F 06F8 05FA3F3000    967       LDN SRC;ANI #3F;BR VFBKDN
  06FD               968 ..
  06FD               969 ..SET VFIB INHIBIT,CLEAR VF REQUEST:
  06FD 05FA7FF940    970 SETVFI: LDN SRC;ANI #7F;ORI #40
F 0702 55C00000C     971 VFBKDN: STR SRC;LBR TWAVE
  0705               972 ..............................
  0705               973 ..T WAVE DETECTED FOLLOWING NORMAL BEAT:
  0705 F8D9A6        974 NRMLTW: LDI A.0(BTTWCT);PLO DST
  0708 06FC0156      975       LDN DST;ADI 1;STR DST
  070D F8D9A6        976       LDI A.0(NLTWCT);PLO DST
  0710 06FC0156      977       LDN DST;ADI 1;STR DST
F 0714 FF083800      978       SMI 8;BNF FOXTWV
  0719               979 ..TOO MANY DETECTED T WAVES! :
  0719 F8F6A6        980       LDI A.0(OUTCTL);PLO DST ..SW LEADS
  071C E37133        981       SEX MPC;DIS,MNEMNE
  071F 05F94056      982       LDN DST;ORI #40;STR DST
  0722 7065          983       RET,DSTMNE
F 0724 3000          984       BR FOXTWV
  0726               985 ..
  0726               986 ..T WAVE FOLLOWS PVC(SET PPM T(N-2))
  0726 F81FA6        987 PVCTWV: LDI A.0(CODWDS-2);PLO DST
  0729 06F90456      988       LDN DST;ORI #04;STR DST
  072D               989 ..COUNT BEATS DOWN IF NARTSEC .NE. 0
  072D F8D3A5        990 FOXTWV: LDI A.0(NARTSC);PLO SRC
F 0730 053200        991       LDN SRC;BZ FIXTWV
  0733               992 ..COUNT BEATS DOWN
F 0733 F800A404      993       LDI A.0(PNTGR);PLO CALL;SEP CALL
  0737 08FF0158      994       LDN GR;SMI 1;STR GR
  073B               995 ..T(N-1) WAS A T WAVE. CLEAR PREM(T(N))
  073B F821A5        996 FIXTWV: LDI A.0(CODWDS);PLO SRC
  073E 05FAFE55      997       LDN SRC;ANI #FE;STR SRC
  0742               998 ..T(N) <- T(N) + T(N-1)
F 0742 F800A4        999       LDI A.0(CLRSUM);PLO CALL
  0745 044A02        1000      SEP CALL,A.0(OLDTIM-3),2
  0748 F8D4A6        1001      LDI A.0(OLDTIM);PLO DST
  074B 975526        1002      GHI SUM;STR DST;DEC DST
  074E 8756          1003      GLO SUM;STR DST
  0750               1004 ..OLDT10<-SUM<- T(N) + 10
F 0750 F800A4        1005      LDI A.0(SHFTLT);PLO CALL
  0753 044C4E01      1006      SEP CALL,A.0(OLDTIM-1),A.0(SCRSTK-9),1
F 0757 F800A4        1007      LDI A.0(MOVE);PLO CALL
  075A 044E5008      1008      SEP CALL,A.0(SCRSTK-9),A.0(SCRSTK-7),8
F 075E F800A4        1009      LDI A.0(CLRSUM);PLO CALL
  0761 044E05        1010      SEP CALL,A.0(SCRSTK-9),5
  0764               1011 ..PUT SUM INTO OLDT10 ANYWAY!
  0764 F875A6        1012      LDI A.0(OLDT10+1);PLO DST
  0767 975626        1013      GHI SUM;STR DST;DEC DST
  076A 8756          1014      GLO SUM;STR DST
  076C               1015 ..SET COMPP ? :
F 076C F800A404      1016      LDI A.0(COMPBR);PLO CALL;SEP CALL
FM 0770 6000000000000 1017      ,A.0(TCP11),A.0(CKPRET),A(SETCPT),A(SETCPT
  0777               1018 ..
  0777               1019 ..SET COMP PAUSE T(N)
  0777 F821A6        1020 SETCPT: LDI A.0(CODWDS);PLO DST
  077A 06F90256      1021      LDN DST;ORI #02;STR DST
F 077E 3000          1022      BR CLMSKT
  0780               1023 ..
  0780 0465          1024 CKPRET: SEP CALL,A.0(TCP09)
FM 0782 000000000000  1025      ,A(SETPRT),A(SETPRT),A(CLMSKT)
  0788               1026 ..
  0788               1027 ..SET PREM(T(N))
  0788 F821A6        1028 SETPRT: LDI A.0(CODWDS);PLO DST
```

```
     0783  06F9)156         1029            LDN DST;ORI #01;STR DST
     078F                   1030  ..CLEAR OUTMSK FLAGS & REPROCESS BEAT
     078F  F80EA6           1031  CLMSKT: LDI A.0(OUTMSK);PLO DST
     0792  06FABF56         1032            LDN DST;ANI #8F;STR DST
     0796                   1033  ..BACKJP CODWDS STACK
F    0796  F800A4           1034            LDI A.0(MOVE);PLO CALL
     0799  D4194F07         1035            SEP CALL,A.0(CODWDS-8),A.0(SCRSTK-8),7
     079D  D44F1A07         1036            SEP CALL,A.0(SCRSTK-8),A.0(CODWDS-7),7
     07A1                   1037  ..BACKJP FINGERPRINT STACK:
     07A1  0493BF08         1038            SEP CALL,A.0(NL1PNL),A.0(NLOPNL),8
     07A5                   1039  ..BACKJP OLDTIM STACK
     07A5  F849A5           1040            LDI A.0(OLDTIM-4);PLO SRC
     07A8  F84BA6E6         1041            LDI A.0(OLDTIM-2);PLO DST;SEX DST
     07AC  057325           1042  BACKOS: LDN SRC;STXD;DEC SRC
     07AF  85FB233AAC       1043            GLO SRC;XRI A.0(OLDTIM-42);BNZ BACKOS
F    07B4  3000             1044            BR STABRT
     07B6                   1045  ..
     07B6                   1046  ..T(N-1) POTENTIAL T WAVE DETECTION?
F    07B6  F80DB8           1047  TWAVE:  LDI A.1(TWAVET);PHI GR
F    07B9  F800A4           1048            LDI A.0(DETALG);PLO CALL
     07BC  F88FA5           1049            LDI A.0(NLOPNL);PLO SRC ..SINGLE DET. ?
F    07BF  05FA3FFB013A00   1050            LDN SRC;ANI #3F;XRI 1;BNZ NOTWAV
F    07C5  041E00           1051            SEP CALL,A.0(CODWDS-3),A.0(TWAVET)
F    07C9  041F00           1052            SEP CALL,A.0(CODWDS-2),A.0(TWAVNT)
     07CC                   1053  ..
     07CC                   1054  ..ANOTHER BEAT BETWEEN T WAVES COUNTED:
     07CC  F8D9A6           1055  NOTWAV: LDI A.0(BTTWCT);PLO DST
F    07CF  063200           1056            LDN DST;BZ BTTWZR
F    07D2  FC01563000       1057            ADI 1;STR DST;BR STABRT
     07D7                   1058  ..
     07D7                   1059  ..ZERO NORMAL TWAVE COUNT(BTTWCT>256)
     07D7  F8DAA6           1060  BTTWZR: LDI A.0(NLTWCT);PLO DST
     07DA  F80056           1061            LDI 0;STR DST
     07DD                   1062  ..
     07DD                   1063  ..R-R INTERVAL STABILITY ROUTINE:
     07DD  F82246           1064  STABRT: LDI A.0(MODCTL);PLO DST
     07E0                   1065  ..SUM.1<-STABCT
     07E0  F88E45           1066            LDI A.0(STABCT);PLO SRC
     07E3  0587             1067            LDN SRC;PHI SUM
F    07E5  F80DB8           1068            LDI A.1(UR1TB);PHI GR
F    07E8  F800A4           1069            LDI A.0(DETALG);PLO CALL
F    07EB  042000           1070            SEP CALL,A.0(CODWDS-1),A.0(UR1TB)
F    07EE  042000           1071            SEP CALL,A.0(CODWDS-1),A.0(UR2TB)
F    07F1  042000           1072            SEP CALL,A.0(CODWDS-1),A.0(URM3TB)
F    07F4  C00000           1073            LBR DACCUM
     07F7                   1074  ..
     07F7                   1075  ..UNSTABLE RYTHYM DOWN COUNT:
F    07F7  97320FFC1B7      1076  URMDCT: GHI SUM;BZ TSTURM;SMI 1;PHI SUM
F    07FD  C00000           1077            LBR TSTURM
     0800                   1078  ..
     0800                   1079  ..UNSTABLE RYTHYM UP COUNT
F    0800  97FF1EC30000     1080  URUPCT: GHI SUM;SMI STABMX;LBDF ONURMD
     0806  97FC03B7         1081            GHI SUM;ADI 3;PHI SUM
     080A                   1082  ..TEST UNSTABLE RYTHYM LEVEL:
F    080A  97FF3FCB0000     1083  TSTURM: GHI SUM;SMI MEDSTB;LBNF OFFURM
     0810                   1084  ..UNSTABLE RYTHYM MODE<-ON :
     0810  06F320FAFB56     1085  ONURMD: LDN DST;ORI #20;ANI #FB;STR DST
     0816  F8DEA6           1086            LDI A.0(OUTMSK);PLO DST
     0819  06F90456         1087            LDN DST;ORI #04;STR DST
F    081D  3000             1088            BR STSTAB
     081F                   1089  ..
     081F                   1090  ..UNSTABLE RYTHYM MODE<- OFF
     081F  06FADF90456      1091  OFFURM: LDN DST;ANI #DF;ORI #04;STR DST
     0825  F8DEA6           1092            LDI A.0(OUTMSK);PLO DST
     0828  06FAFB56         1093            LDN DST;ANI #FB;STR DST
     082C                   1094  ..STORE STABILITY COUNTER:
     082C  F88E45           1095  STSTAB: LDI A.0(STABCT);PLO SRC
     082F  9755             1096            GHI SUM;STR SRC
     0831                   1097  ..................................
     0831                   1098  ..DATA ACCUMULATION,INDICATION &
     0831                   1099  ..FINGERPRINTS UNDER ARTIFACTS:
     0831  F822A5           1100  DACCUM: LDI A.0(MODCTL);PLO SRC
F    0834  05FA0A3200       1101            LDN SRC;ANI #0A;BZ ARTNOD ..START,H.L.AR
     0839                   1102  ..ARTIFACTS. CLEAR RUNS,BIGM,PVC,LTHR,DROPPED!
     0839  F8DEA6           1103            LDI A.0(OUTMSK);PLO DST
     083C  05FA0756         1104            LDN DST;ANI #07;STR DST
     0840  F81FA6           1105            LDI A.0(CODWDS-2);PLO DST
     0843  05FABF56         1106            LDN DST;ANI #BF;STR DST
```

```
       0847                  1107 ..CHECK FINGERPRINT:
       0847 F893A8            1108       LDI A.0(NL1PNL);PLO GR
F      084A F800A4            1109       LDI A.0(CHKFPT);PLO CALL
FF     084D 04020000C00000    1110       SEP CALL,2,A(FP2YES);LBR SIGNDT
       0854                  1111 ..
       0854                  1112 ..FINGERPRINT MATCHED PVC!
       0854                  1113 ..,BUT > 1 MORPH.CHANGE REQUIRED!
       0854 F81FA6            1114 FP2YES: LDI A.0(CODWDS-2);PLO DST
F      0857 06FA1C3200        1115       LDN DST;ANI #1C;BZ SIGNDT
F      085C 05FA8C3200        1116       LDN DST;ANI #8C;BZ SIGNDT
F      0861 06FA943200        1117       LDN DST;ANI #94;BZ SIGNDT
F      0866 06FA983200        1118       LDN DST;ANI #98;BZ SIGNDT
       086B                  1119 ..MARK BEAT AS PVC:
       086B 06F94056          1120       LDN DST;ORI #40;STR DST
       086F F8DEA5            1121       LDI A.0(OUTMSK);PLO SRC
F      0872 F840553000        1122       LDI #40;STR SRC;BR SIGNDT
       0877                  1123 ..
       0877                  1124 ..
       0877                  1125 ..NO ARTIFACTS. IF PVC,STORE FINGERPRINT
       0877 F8DEA5            1126 ARTNOD: LDI A.0(OUTMSK);PLO SRC
F      087A 05FA403200        1127       LDN SRC;ANI #40;BZ SIGNDT
       087F F893A8            1128       LDI A.0(NL1PNL);PLO GR
F      0882 F800A4            1129       LDI A.0(CHKFPT);PLO CALL
F      0885 040100C0          1130       SEP CALL,1,A(SIGNDT)
       0889                  1131 ..STORE FINGERPRINT AT PVCPNL(36)
       0889 F83AA5            1132 STRFPT: LDI A.0(PV1WID+28);PLO SRC
       088C F8BEA676          1133       LDI A.0(PV1WID+32);PLO DST;SEX DST
       0890 057325            1134 PVFPLP: LDN SRC;STXD;DEC SRC
       0893 85FA9A3A90        1135       GLO SRC;XRI A.0(PV1PNL-1);BNZ PVFPLP
F      0898 F80CA4            1136       LDI A.0(MOVE);PLO CALL
       089B 04939804          1137       SEP CALL,A.0(NL1PNL),A.0(PV1PNL),4
       089F                  1138 ..SIGNAL THE DETECTION CONDITION
       089F F8DEA5            1139 SIGNDT: LDI A.0(OUTMSK);PLO SRC
       08A2 F8C3A6            1140       LDI A.0(OUTIND);PLO DST
       08A5 05FAF765          1141       LDN SRC;ANI #F7;SEX SRC ..IND<-MSK
       08A9 25F156            1142       DEC SRC;OR;STR DST ..IND<-MK2
       08AC 15                1143       INC SRC ..SRC<- A(OUTMSK)
       08AD 05FA082645        1144       LDN SRC;ANI #08;BZ **6
       08B2 05F94056          1145       LDN DST;ORI #40;STR DST ..LTHR PVC
       08B6 F822A5            1146       LDI A.0(MODCTL);PLO SRC
       08B9 E6                1147       SEX DST ..OR HL,LL,ARTS.:
       08BA 05FA03F156        1148       LDN SRC;ANI #03;OR;STR DST
F      08BF 05FA88F803A00     1149       LDN SRC;ANI #88;XRI #80;BNZ SIGNOW ..VF?
       08C5 05F91056          1150       LDN DST;ORI #10;STR DST ..YES,RUN!
       08CA 67                1151 SIGNOW: OUT IND
       08CB                  1152 ..................................
       08CB                  1153 ..ACCUMULATE TREND DATA:
       08CB F8C3A5            1154 TRENDT: LDI A.0(OUTIND);PLO SRC
       08CE F8D4A6            1155       LDI A.0(MRKPVC);PLO DST
       08D1                  1156 ..GR<- A(PVCMIN)
F      08D1 F80A4D4           1157       LDI A.0(PNTGR);PLO CALL;SEP CALL
       08D5 88FC0FA8          1158       GLO GR;ADI DSBTPV;PLO GR
       08D9                  1159 ..ACCUMULATE RJNS?
F      08D9 05FA103200        1160       LDN SRC;ANI #10;BZ BIGACC
       08DE                  1161 ..RUNS OR SVT? :
F      08DE 05FA08CA0000      1162       LDN SRC;ANI #08;LBNZ CNTSVT
       08E4                  1163 ..RUNS! WAS T(N-1) COUNTED AS PVC? :
F      08E4 06FA023200        1164       LDN DST;ANI #02;BZ REMRUN
       08E9                  1165 ..YES,UNMARK AND UNCOUNT AS PVC:
       08E9 05F4FC56          1166       LDN DST;ANI #FC;STR DST
F      08ED 093200            1167       LDN GR;BZ REMRUN
       08F0 FF0158            1168       SMI 1;STR GR ..-1 PVC!
       08F3 F8D5A5            1169 REMRUN: LDI A.0(MRKRUN);PLO SRC
       08F6 05F90155          1170       LDN SRC;ORI #01;STR SRC ..MRK!
       08FA                  1171 ..WAS RUN COUNTED YET?
F      08FA 05FA02CA000       1172       LDN SRC;ANI #02;LBNZ DETRTS
       0900                  1173 ..RUNCT<- RUNCT +1
       0900 80FC04A8          1174 CNTRUN: GLO DAT;ADI DSMNRV;PLO GR
       0904 08FC015818        1175       LDN GR;ADI 1;STR GR;INC GR
       0909 087C0058          1176       LDN GR;ADCI 0;STR GR
F      090D C00000            1177       LBR JRACC
       0910                  1178 ..
       0910 F8D6A5            1179 CNTSVT: LDI A.0(MRKSVT);PLO SRC
       0913 05F90155          1180       LDN SRC;ORI #01;STR SRC
F      0917 FA023A00          1181       ANI #02;BNZ NOCSVT
       091B 80FC43A8          1182       GLO DAT;ADI DMNSVT;PLO GR
       091F 08FC015818        1183       LDN GR;ADI 1;STR GR;INC GR
       0924 087C0058          1184       LDN GR;ADCI 0;STR GR
```

```
F  0928 C00000           1185 NOCSVT: LBR LTHACC
   0928                  1186 ..
   0928                  1187 ..ACCUMULATE BIGEMINI?
F  092B 05FA20C20000     1188 BIGACC: LDN SRC;ANI #20;LBZ PVCACC
   0931                  1189 ..YES,ENCODE BIGEMINI:
   0931 9887             1190         GHI GR;PHI SUM
   0933 88FA80FC0EA7     1191         GLO GR;ANI #80;ADI A.0(CODES2);PLO SUM
   0939 07F91057         1192         LDN SUM;ORI #10;STR SUM
   093D                  1193 ..T(N-6) COUNTED AS PVC?
F  093D 05FA403A00       1194         LDN DST;ANI #40;BNZ CKBTN4
   0942 05F94056         1195         LDN DST;ORI #40;STR DST ..MARK PVC
   0946 08FC0158         1196         LDN GR;ADI 1;STR GR ..COUNT PVC
   094A                  1197 ..T(N-4) COUNTED AS PVC?
F  094A 05FA103A00       1198 CKBTN4: LDN DST;ANI #10;BNZ CKBTN2
   094F 05F91056         1199         LDN DST;ORI #10;STR DST ..MARK PVC
   0953 08FC0158         1200         LDN GR;ADI 1;STR GR ..COUNT PVC
   0957                  1201 ..T(N-2) COUNTED AS PVC?
F  0957 05FA043A00       1202 CKBTN2: LDN DST;ANI #04;BNZ CNTPVC
   095C 05F90456         1203         LDN DST;ORI #04;STR DST ..MARK PVC
   0960 08FC0158         1204         LDN GR;ADI 1;STR GR ..COUNT PVC
   0964 05F901           1205 CNTPVC: LDN DST;ORI #01 ..MARK PVC
   0967 56               1206 INCPVC: STR DST
   0968 08FC0158         1207         LDN GR;ADI 1;STR GR ..COUNT PVC
F  096C C00000           1208         LBR JRACC
   096F                  1209 ..
   096F                  1210 ..ACCUMULATE SINGLE PVC? :
F  096F 05FA40C20000     1211 PVCACC: LDN SRC;ANI #40;LBZ LTHACC
   0975                  1212 ..PVC OR SVEB? :
   0975 05FA083264       1213         LDN SRC;ANI #08;BZ CNTPVC
   097A                  1214 ..ACCUMULATE SVEB:
   097A 88FC1EA8         1215         GLO GR;ADI DSPVSV;PLO GR
   097E 3068             1216         BR INCPVC+1
   0980                  1217 ..ACCUMULATE LTHR PVC? :
   0980 F8DEA5           1218 LTHACC: LDI A.0(OUTMSK);PLO SRC
F  0983 05FA08C20000     1219         LDN SRC;ANI #08;LBZ DBACC
   0989 05F901FE         1220         LDN DST;ORI #01;SHL ..MARK LTHR
   098D C00967           1221         LBR INCPVC ..COUNT PVC
   0990                  1222 ..
   0990                  1223 ..ACCUMULATE DROPPED BEAT? :
F  0990 05FA80C20000     1224 DBACC:  LDN SRC;ANI #80;LBZ URACC
   0996 88FC06A8         1225         GLO DAT;ADI DSMNDB;PLO GR
   099A 08FC0158         1226         LDN GR;ADI 1;STR GR
   099E                  1227 ..
   099E                  1228 ..ENCODE UNSTABLE RYTHYM? :
   099E F822A5           1229 URACC:  LDI A.0(MODCTL);PLO SRC
F  09A1 05FA20C20000     1230         LDN SRC;ANI #20;LBZ DETRTS
   09A7 88FA80FC0EA8     1231         GLO GR;ANI #80;ADI A.0(CODES2);PLO GR
   09AD 08F92058         1232         LDN GR;ORI #20;STR GR ..U.R.!
   09B1                  1233 ..................................
   09B1                  1234 ..PRIMARY DETECTION ALGORITHMS:
   09B1                  1235 ..FIRST CLEAR OUTMSK & OUTMK2
   09B1 F8DEA6           1236 DETRTS: LDI A.0(OUTMSK);PLO DST
   09B4 05FA1756         1237         LDN DST;ANI #17;STR DST
   09B8 26F80056         1238         DEC DST;LDI 0;STR DST
   09BC                  1239 ..SKIP IN STARTUP OR STARTUP BLANKING:
   09BC F822A5           1240         LDI A.0(MODCTL);PLO SRC
F  09BF 45FA08CA0000     1241         LDA SRC;ANI #08;LBNZ UPDTIM
   09C5                  1242 ..CHECK M02CTL (#02=MOPH STRETCH ARTS)
F  09C5 05FA02CA0000     1243         LDN SRC;ANI #02;LBNZ UPDTIM
   09CB F8DCA5           1244         LDI A.0(STBLNK);PLO SRC
F  09CE 053200           1245         LDN SRC;BZ DODETR ..BLANKING DONE?
F  09D1 FF0156C00000     1246         SMI 1;STR SRC;LBR UPDTIM
   09D7                  1247 ..
F  09D7 F800B8           1248 DODETR: LDI A.1(ENDRUN);PHI GR
F  09DA F800A4           1249         LDI A.0(DETALG);PLO CALL
   09DD                  1250 ..IF RJNS ON JUST LOOK FOR TERMINATION
   09DD F8DEA6           1251         LDI A.0(OUTMSK);PLO DST
F  09E0 05FA103A00       1252         LDN DST;ANI #10;BNZ CKREND
   09E5 F8C3A6           1253         LDI A.0(OJTIND);PLO DST
F  09E8 05FA08CA0000     1254         LDN DST;ANI #08;LBNZ PVCDU ..SUPRA
F  09EE 05FA10C20000     1255         LDN DST;ANI #10;LBZ PVCDU ..VT?
   09F4                  1256 ..
   09F4                  1257 ..RUNS,CHECK TO END?
   09F4 F8DAA6           1258 CKREND: LDI A.0(RNBEAT);PLO DST
   09F7 05FC0156         1259         LDN DST;ADI 1;STR DST
   09FB                  1260 ..IF RJN .GT. 50 BEATS,RUNCTL<- OFF
   09FB                  1261 ...FPT. STACK<- 0
```

```
F   09F3  FF32CB0000        1262           SMI 50;LBNF DTRNDN
    0A00  F822A6            1263           LDI A.0(MODCTL);PLO DST
    0A03  05FAEF55          1264           LDN DST;ANI #EF;STR DST ..RUNCTL<-0
    0A07                    1265  ..ZERO FPT. STACK:
    0A07  F89846            1266           LDI A.0(PV1PNL);PLO DST
    0A0A  F8005616          1267  ZERFPT:  LDI 0;STR DST;INC DST
    0A0E  85F38F3A0A        1268           GLO DST;XRI A.0(SVLNGX);BNZ ZERFPT
    0A13                    1269  ..IF VT(VFIB) .GT. 60 BEATS,SWITCH LEADS:
    0A13  F8DAA6            1270           LDI A.0(RNBEAT);PLO DST
F   0A16  05FF3CCB0000      1271           LDN DST;SMI 60;LBNF DTRNDN
    0A1C                    1272  ..SWITCH LEADS:
    0A1C  F80056            1273           LDI 0;STR DST ..RNBEAT<-0
    0A1F  F8F6A6            1274           LDI A.0(OJTCTL);PLO DST
    0A22  E37133            1275           SEX MPC;DIS,MNEMNE
    0A25  05F94056          1276           LDN DST;ORI #40;STR DST
    0A29  7063              1277           RET,DSTMNE
    0A2B                    1278  ..DETECT RUN DONE?  :
F   0A2B  042000            1279  DTRNDN:  SEP CALL,A.0(CODWDS-1),A.0(ENDRUN)
F   0A2E  C00000            1280           LBR JPDTIM
    0A31                    1281  ..
    0A31  F8DEA6            1282  OFFRUN:  LDI A.0(OUTMSK);PLO DST
    0A34  05FAEF55          1283           LDN DST;ANI #EF;STR DST
    0A38  F8DAA6            1284           LDI A.0(RNBEAT);PLO DST
    0A3B  F80056            1285           LDI 0;STR DST ..END OF RUN!
    0A3E                    1286  ..WAS RUN A COUPLET?
F   0A3E  041000            1287           SEP CALL,A.0(CODWDS-4),A.0(CPLTB)
F   0A41  C00000            1288           LBR JPDTIM
    0A44                    1289  ..
    0A44                    1290  ..STORE(COUNT) COUPLETS:
    0A44  9DB8              1291  STCPL:   GHI DAT;PHI GR
    0A46  80FC45A9          1292           GLO DAT;ADI DMNCPL;PLO GR
    0A4A  08FC015818        1293           LDN GR;ADI 1;STR GR;INC GR
    0A4F  087C005B          1294           LDN GR;ADCI 0;STR GR
F   0A53  C00000            1295           LBR JPDTIM
    0A56                    1296  ..
    0A56                    1297  ..SINGLE PVC DETECTION ALGORITHMS
F   0A56  042000            1298  PVCOU:   SEP CALL,A.0(CODWDS-1),A.0(PVCOUT)
F   0A59  041F00            1299  PVCAU:   SEP CALL,A.0(CODWDS-2),A.0(PVCAUT)
F   0A5C  041F00            1300  PVCINT:  SEP CALL,A.0(CODWDS-2),A.0(PVCI1T)
F   0A5F  041F00            1301  PVCAS:   SEP CALL,A.0(CODWDS-2),A.0(PVCATB)
F   0A62  041F00            1302  PVCBS:   SEP CALL,A.0(CODWDS-2),A.0(PVCBTB)
F   0A65  041F00            1303  PVCCS:   SEP CALL,A.0(CODWDS-2),A.0(PVCCTB)
F   0A68  041F00            1304  PVCDS:   SEP CALL,A.0(CODWDS-2),A.0(PVCDTB)
F   0A6B  042000            1305  PVCES:   SEP CALL,A.0(CODWDS-1),A.0(PVCETB)
    0A6E                    1306  ..CHECK FINGERPRINT AGAINST OLD PVC'S :
F   0A6E  F800A4            1307  CKFPT:   LDI A.0(CHKFPT);PLO CALL
    0A71  F88FA8            1308           LDI A.0(NLDPNL);PLO GR
F=  0A74  040300003000      1309           SEP CALL,3,A(MAYPVC);BR CKRUNS
    0A7A                    1310  ..
    0A7A                    1311  ..MATCHED FPT..MAYBEE PVC,BUT
    0A7A                    1312  .. >1 MOPH.CHANGE REQ'D.
    0A7A  F820A6            1313  MAYPVC:  LDI A.0(CODWDS-1);PLO DST
F   0A7D  05FA1CC20000      1314           LDN DST;ANI #1C;LBZ CKRUNS
F   0A83  05FA8CC20000      1315           LDN DST;ANI #8C;LBZ CKRUNS
F   0A89  05FA94C20000      1316           LDN DST;ANI #94;LBZ CKRUNS
F   0A8F  05FA98C20000      1317           LDN DST;ANI #98;LBZ CKRUNS
F   0A95  C00000            1318           LBR FLGPVC
    0A98                    1319  ..
    0A98                    1320  ..
    0A98                    1321  ..PVC DETECTED,ADJUST TIME STACK:
    0A98                    1322  ..T(N),(N-1)<- T(N),(N-1)/2
F   0A98  F800A4            1323  STPVC:   LDI A.0(SHFTRT);PLO CALL
    0A9B  0444AC02          1324           SEP CALL,A.0(OLDTIM-3),A.0(OLDTIM-3),2
    0A9F                    1325  ..SUM<- (T(N)+T(N-1))/2
F   0A9F  F800A4            1326  SUMPVC:  LDI A.0(CLRSUM);PLO CALL
    0AA2  0444D2            1327           SEP CALL,A.0(OLDTIM-3),2
    0AA5  F84DA6E6          1328           LDI A.0(OLDTIM);PLO DST;SEX DST
    0AA9  97738773          1329           GHI SUM;STXD;GLO SUM;STXD
    0AAD  97738773          1330           GHI SUM;STXD;GLO SUM;STXD
    0AB1                    1331  ..FLAG PVC IN CODWDS STACK:
    0AB1  F820A6            1332  FLGPVC:  LDI A.0(CODWDS-1);PLO DST
    0AB4  05F94056          1333           LDN DST;ORI #40;STR DST
    0AB8                    1334  ..TURN ON BEAT IN OUTMSK
    0AB8  F8DEA6            1335  MSKPVC:  LDI A.0(OUTMSK);PLO DST
    0ABB  05F94056          1336           LDN DST;ORI #40;STR DST
F   0ABF  F900B8            1337  CKRUNS:  LDI A.1(RUN7TB);PHI GR
F   0AC2  F800A4            1338           LDI A.0(DETALG);PLO CALL ..REINIT CALL
F   0AC5  041F00            1339  RUN7S:   SEP CALL,A.0(CODWDS-3),A.0(RUN7TB)
```

```
F   0AC8  D41F00       1340 RUN1S:   SEP CALL,A.0(CODWDS-2),A.0(RUN1TB)
F   0ACB  D41F00       1341 RUN2S:   SEP CALL,A.0(CODWDS-2),A.0(RUN2TB)
F   0ACE  D41F00       1342 RUN3S:   SEP CALL,A.0(CODWDS-2),A.0(RUN3TB)
F   0AD1  D41F00       1343 RUN4SU:  SEP CALL,A.0(CODWDS-2),A.0(RUN4TB)
F   0AD4  D41F00       1344 RUN8SU:  SEP CALL,A.0(CODWDS-2),A.0(RUN8TB)
F   0AD7  D41F00       1345 RUN5SU:  SEP CALL,A.0(CODWDS-2),A.0(RUN5TB)
F   0ADA  D41A00       1346 BIGMD1:  SEP CALL,A.0(CODWDS-7),A.0(BIGM1D)
F   0ADD  D41A00       1347 BIGMD2:  SEP CALL,A.0(CODWDS-7),A.0(BIGM2D)
F   0AE0  D41F00       1348 SVEB:    SEP CALL,A.0(CODWDS-2),A.0(SVEBTB)
F   0AE3  D41F00       1349 SVT:     SEP CALL,A.0(CODWDS-2),A.0(SVTB)
    0AE6  C00000       1350          LBR JPDTIM
    0AE9                1351 ..
    0AE9                1352 ..
    0AE9  F80DA6       1353 STRUNS:  LDI A.0(OUTMSK);PLO DST
    0AEC  F81056       1354          LDI #10;STR DST
    0AEF                1355 ..MODCTL <- RUNS
    0AEF  F822A6       1356          LDI A.0(MODCTL);PLO DST
    0AF2  05F91056     1357          LDN DST;ORI #10;STR DST
    0AF6                1358 ..RUNS COUNT STABILITY DOWN
    0AF6  F88FA6       1359          LDI A.0(STABCT);PLO DST
F   0AF9  05C20000     1360          LDN DST;LBZ UPDTIM
    0AFD  FF0156       1361          SMI 1;STR DST
F   0B00  C00000       1362          LBR JPDTIM
    0B03                1363 ..
    0B03                1364 ..
    0B03  F80DA6       1365 BIGPVC:  LDI A.0(OUTMSK);PLO DST
    0B06  05F92056     1366          LDN DST;ORI #20;STR DST
F   0B0A  C00000       1367          LBR JPDTIM
    0B0D                1368 ..
    0B0D                1369 ..SVEB MUST BE TCP PREM! :
    0B0D  F807A6       1370 STSVEB:  LDI A.0(MRKPRM);PLO DST
F   0B10  05FA02C20000 1371          LDN DST;ANI #02;LBZ UPDTIM
    0B16  F80DA6       1372          LDI A.0(OUTMK2);PLO DST
    0B19  05F94856     1373          LDN DST;ORI #48;STR DST
F   0B1D  C00000       1374          LBR UPDTIM
    0B20                1375 ..
    0B20  F807A6       1376 STSVT:   LDI A.0(MRKPRM);PLO DST
F   0B23  05FA03C20000 1377          LDN DST;ANI #03;LBZ UPDTIM
    0B29  F80DA6       1378          LDI A.0(OUTMK2);PLO DST
    0B2C  05F91856     1379          LDN DST;ORI #18;STR DST
F   0B30  C00000       1380          LBR JPDTIM
    0B33                1381 ..........................................
    0C00                1382          PAGE
    0C00                1383 ..
    0C00                1384 ..UPDATE OLDTIM STACK:
    0C00                1385 ..ETC;T(N-2)<- T(N-1);T(N-1)<- OLDTIM
    0C00  F822A6       1386 UPDTIM:  LDI A.0(MODCTL)
I   0C03  E66026       1387          SEX DST;OUT MODPRT;DEC DST ..TEST
    0C06                1388 ..               *******
F   0C06  05FA12CA0000 1389          LDN DST;ANI #12;LBNZ CJNTBT
F   0C0C  F800A4       1390          LDI A.0(MOVE);PLO CALL
    0C0F  04262428     1391          SEP CALL,A.0(OLDTIM-39),A.0(OLDTIM-41),40
    0C13                1392 ..
    0C13                1393 ..
    0C13                1394 ..TP(TPREM)*32 = T(N-4) +
    0C13  04446502     1395          SEP CALL,A.0(OLDTIM-9),A.0(SCRSTK-1),2
    0C17                1396          .. + 2*T(N-3)
F   0C17  F800A4       1397          LDI A.0(SHFTLT);PLO CALL
    0C1A  04466003     1398          SEP CALL,A.0(OLDTIM-7),A.0(SCRSTK-7),3
    0C1E                1399 .. -2*T(N-1)  ..(TWO'S COMPLEMENT:)
    0C1E  F85445       1400          LDI A.0(SCRSTK-3);PLO SRC
    0C21  45FBFFA7     1401          LDA SRC;XRI #FF;PLO SUM
    0C25  05FBFFB717   1402          LDN SRC;XRI #FF;PHI SUM;INC SUM
    0C2A                1403 .. + 4*T(N-2)
    0C2A  04525202     1404          SEP CALL,A.0(SCRSTK-5),A.0(SCRSTK-5),2
    0C2E                1405 .. + 8*T(N-1)
    0C2E  04545401     1406          SEP CALL,A.0(SCRSTK-3),A.0(SCRSTK-3),1
    0C32                1407 .. + 16*T(N-1)
    0C32  04544801     1408          SEP CALL,A.0(SCRSTK-3),A.0(SCRSTK-9),1
    0C36                1409 ..SUM STCK FOR 32*TP (TPREM) :
F   0C36  F800A4       1410          LDI A.0(STKSJM);PLO CALL
    0C39  0448F05      1411          SEP CALL,A.0(SCRSTK-9),5
    0C3C  F863A5E6     1412          LDI A.0(TP32+1);PLO SRC;SEX SRC
    0C40  97738773     1413          GHI SJM;STXD;GLO SUM;STXD
    0C44                1414 ..
    0C44                1415 ..
    0C44                1416 ..
    0C44                1417 ..STKSJM(5) *2->T5P10
```

```
F  0C44  F800A4       1418              LDI  A.0(CLRSUM);PLO CALL
   0C47  044205       1419              SEP  CALL,A.0(OLDTIM-11),5
   0C4A  F88A6E6      1420              LDI  A.0(T5P10+1);PLO DST;SEX DST
   0C4E  97738773     1421              GHI  SJM;STXD;GLO SUM;STXD
F  0C52  F800A4       1422              LDI  A.0(SHFTLT);PLO CALL
   0C55  D48A8A01     1423              SEP  CALL,A.0(T5P10),A.0(T5P10),1
   0C59                1424       ..
   0C59                1425       ..TCP10<- STSJM((10/2)+(10/2))  :
   0C59                1426       ..TCP10<- STSJM(10)
F  0C59  F800A4       1427              LDI  A.0(CLRSUM);PLO CALL
   0C5C  04240A       1428              SEP  CALL,A.0(OLDTIM-41),10
   0C5F  F85FA6E6     1429              LDI  A.0(TCP10+1);PLO DST;SEX DST
   0C63  97738773     1430              GHI  SJM;STXD;GLO SUM;STXD
   0C67                1431       ..TCP11<- STSJM(10)'
F  0C67  F800A4       1432              LDI  A.0(CLRSUM);PLO CALL
   0C6A  04380A       1433              SEP  CALL,A.0(OLDTIM-21),10
   0C6D  F861A6E6     1434              LDI  A.0(TCP11+1);PLO DST;SEX DST
   0C71  97738773     1435              GHI  SJM;STXD;GLO SUM;STXD
   0C75                1436       ..TCP10,11<- (TCP10,11)/2
F  0C75  F800A4       1437              LDI  A.0(SHFTRT);PLO CALL
   0C78  D45E5E02     1438              SEP  CALL,A.0(TCP10),A.0(TCP10),2
   0C7C                1439       ..SUM<- TOTAL STKSUM(20)
F  0C7C  F800A4       1440              LDI  A.0(CLRSUM);PLO CALL
   0C7F  045E02       1441              SEP  CALL,A.0(TCP10),2
   0C82                1442       ..TCP10<- LARGER(STSUM(5),STSUM(20))
   0C82  F88AA6E6     1443              LDI  A.0(T5P10);PLO DST;SEX DST
   0C86  87F716       1444              GLO  SUM;SM;INC DST
F  0C89  97775300     1445              GHI  SJM;SMB;BPZ TENSUM
   0C8D  06B726       1446              LDN  DST;PHI SUM;DEC DST
   0C90  06A7         1447              LDN  DST;PLO SUM
   0C92  F85EA6       1448  TENSUM: LDI  A.0(TCP10);PLO DST
   0C95  875316       1449              GLO  SJM;STR DST;INC DST
   0C98  9756         1450              GHI  SJM;STR DST
   0C9A                1451       ..
F  0C9A  F800A4       1452  DOT11:  LDI  A.0(SHFTRT);PLO CALL
   0C9D  045E5C01     1453              SEP  CALL,A.0(TCP10),A.0(TCP10H),1
   0CA1  D45C5801     1454              SEP  CALL,A.0(TCP10H),A.0(TCP10Q),1
   0CA5  D4585A01     1455              SEP  CALL,A.0(TCP10Q),A.0(TCP10E),1
   0CA9                1456       ..TCP09<- (1/4 +1/8 +1/2) * TCP10
F  0CA9  F800A4       1457              LDI  A.0(CLRSUM);PLO CALL
   0CAC  045803       1458              SEP  CALL,A.0(TCP10Q),3
   0CAF  F867A6E6     1459              LDI  A.0(TCP09+1);PLO DST;SEX DST
   0CB3  97738773     1460              GHI  SJM;STXD;GLO SUM;STXD
   0CB7                1461       ..ITPLNG<- (1/8 +1/2) * TCP10
F  0CB7  F800A4       1462              LDI  A.0(CLRSUM);PLO CALL
   0CBA  045A02       1463              SEP  CALL,A.0(TCP10E),2
   0CBD  E697738773   1464              SEX  DST;GHI SUM;STXD;GLO SUM;STXD
   0CC2                1465       ..ITPSHT<- (1/4 +1/8) * TCP10
F  0CC2  F800A4       1466              LDI  A.0(CLRSUM);PLO CALL
   0CC5  045802       1467              SEP  CALL,A.0(TCP10Q),2
   0CC8  E697738773   1468              SEX  DST;GHI SUM;STXD;GLO SUM;STXD
   0CCD                1469       ..TCP11<- (1 +1/8) * TCP10
F  0CCD  F800A4       1470              LDI  A.0(CLRSUM);PLO CALL
   0CD0  045E01       1471              SEP  CALL,A.0(TCP10),1
   0CD3  045A01       1472              SEP  CALL,A.0(TCP10E),1
   0CD6  E697738773   1473              SEX  DST;GHI SUM;STXD;GLO SUM;STXD
   0CDB                1474       ..TCP27<- TCP09 + 2*TCP09
F  0CDB  F800A4       1475              LDI  A.0(SHFTLT);PLO CALL
   0CDE  D4666801     1476              SEP  CALL,A.0(TCP09),A.0(TCP27),1
F  0CE2  F800A4       1477              LDI  A.0(CLRSUM);PLO CALL
   0CE5  046602       1478              SEP  CALL,A.0(TCP09),2
   0CE8  F869A6       1479              LDI  A.0(TCP27+1);PLO DST
   0CEB  E697738773   1480              SEX  DST;GHI SUM;STXD;GLO SUM;STXD
   0CF0                1481       ..
   0CF0                1482       ..TCP105(TCP10.5)<-((TCP10/2)+(TCP11/2))
F  0CF0  F800A4       1483              LDI  A.0(SHFTRT);PLO CALL
   0CF3  045E5402     1484              SEP  CALL,A.0(TCP10),A.0(SCRSTK-3),2
F  0CF7  F800A4       1485              LDI  A.0(CLRSUM);PLO CALL
   0CFA  045402       1486              SEP  CALL,A.0(SCRSTK-3),2
   0CFD  F86FA6E6     1487              LDI  A.0(TCP105+1);PLO DST;SEX DST
   0D01  97738773     1488              GHI  SJM;STXD;GLO SUM;STXD
   0D05                1489       ..
   0D05                1490       ..
   0D05                1491       ..
   0D05                1492       ..IF 300MS. < ITPSHT,:ITPSHT<- 300MS.
   0D05  F80B87       1493              LDI  A.1(TREHUN);PHI SUM
   0D08  F8B947       1494              LDI  A.0(TREHUN);PLO SUM
F  0D0B  F800A404     1495              LDI  A.0(COMPBR);PLO CALL;SEP CALL
```

```
FM 000F 520000000000000   1496 .,A.0(ITPSHT),A(RPLSHT),A(DOITLG),A(DOITLG)
   0015                   1497 ..
   0015                   1498 ..
   0015 F863A6E6          1499 RPLSHT: LDI A.0(ITPSHT+1);PLO DST;SEX DST
   001A 97738773          1500         GHI SJM;STXD;GLO SUM;STXD
   001E                   1501 ..
   001E                   1502 ..IF(TCP10-300MS.)>ITPLNG,::ITPLNG<-(TCP10-300MS.
   001E                   1503 ..SUM<- (TCP10 -300MS.)
   001E F85EA5            1504 DOITLG: LDI A.0(TCP10);PLO SRC
   0021 45FFA8A7          1505         LDA SRC;SMI A.0(TREHUND);PLO SUM
   0025 057F0B87          1506         LDN SRC;SMBI A.1(TREHUND);PHI SUM
F  0029 3800              1507         BNF LNGOK ..BM
F  002B F80JA4D4          1508         LDI A.0(COMPBR);PLO CALL;SEP CALL
FM 002F 640000000000000   1509 .,A.0(ITPLNG),A(LNGOK),A(LNGOK),A(RPLONG)
   0035                   1510 ..
   0035 F863A6E6          1511 RPLONG: LDI A.0(ITPLNG+1);PLO DST;SEX DST
   003A 97738773          1512         GHI SJM;STXD;GLO SUM;STXD
   003E                   1513 ..
   003E                   1514 ..TCP07(SUM)<- (1/2 + 1/4)*TCP10
F  003E F80JA4            1515 LNGOK:  LDI A.0(CLRSUM);PLO CALL
   0041 D45801            1516         SEP CALL,A.0(TCP10Q),1
   0044 D45C01            1517         SEP CALL,A.0(TCP10H),1
   0047 F88JA6E6          1518         LDI A.0(DIMTME+1);PLO DST;SEX DST
F  004B 973200            1519         GHI SJM;BZ CKDMLO
F  004E F8013A00          1520         XRI #01;BNZ DIM300
   0052                   1521 ..TCP07 > 300MS.?
F  0052 87FF2C3300        1522         GLO SUM;SMI #2C;BPZ DIM300
   0057                   1523 ..TCP07 -->DIMTME
   0057 97738773          1524 STDM07: GHI SJM;STXD;GLO SUM;STXD
F  005B 3000              1525         BR CUNTBT
   005D                   1526 ..
   005D                   1527 ..
   005D 87FFE73357        1528 CKDMLO: GLO SUM;SMI 231;BPZ STDM07
   0062 F80073F80773      1529         LDI 0;STXD;LDI 231;STXD
F  0068 3000              1530         BR CUNTBT
   006A                   1531 ..
   006A F80173F82C73      1532 DIM300: LDI 1;STXD;LDI #2C;STXD
   0070                   1533 ..
   0070                   1534 ..COUNT BEATS FOR 15 ARTIFACT FREE
   0070                   1535 ..SECONDS OF EACH MINUTE
   0070 F822A5            1536 CUNTBT: LDI A.0(MODCTL);PLO SRC
F  0073 05FA0A3A00        1537         LDN SRC;ANI #0A;BNZ UPCODW ..ARTS?
   0078 F803A5            1538         LDI A.0(NAPTSC);PLO SRC
F  007B 053200            1539         LDN SRC;BZ UPCODW ..15SECS.YET?
F  007E F80JA4D4          1540         LDI A.0(PNTGR);PLO CALL;SEP CALL
   0082 08FC0158          1541         LDN GR;ADI 1;STR GR ..COUNT BEAT
   0085                   1542 ..IF T(N)=LTHR.PVC.,COUNT EXTRA BEAT:
   0085 F8C3A5            1543         LDI A.0(OUTIND);PLO SRC
F  0089 05FA083200        1544         LDN SRC;ANI #08;BZ UPCODW
   008E 08FC0158          1545         LDN GR;ADI 1;STR GR ..LTHR PVC!
   0092                   1546 ..........................................
   0092                   1547 ..STRETCH ARTS IF S.D. OR PK.DIFF. :
   0092 F822A6E6          1548 UPCODW: LDI A.0(MODCTL);PLO DST;SEX DST
   0096 46FA02F155        1549         LDA DST;AVI #02;OR;STR DST ..ART->MO2CTL
   009B F821A5            1550         LDI A.0(CODWDS);PLO SRC
F  009E 05FA003A00        1551         LDN SRC;ANI #90;BNZ CKCODP ..MOPH CHNG?
F  00A3 F800630C00        1552         LDI 0;STR DST;BR RNMOCL ..RESET MO2CTL
F  00A8 05FA013A00        1553 CKCODP: LDN SRC;ANI #01;BNZ UPDTFP ..PREM?
F  00AD F80JB8            1554         LDI A.1(RUN2CH);PHI GR
F  00B0 F80JA4            1555         LDI A.0(DETALG);PLO CALL
F  00B3 D42100            1556         SEP CALL,A.0(CODWDS),A.0(RUN2CH)
   00B6                   1557 ..LESS THAN 2 M.CHG.? RUNMDE<-OFF
   00B6 F822A6            1558 RNMOCL: LDI A.0(MODCTL);PLO DST
   00B9 05FAEF55          1559         LDN DST;ANI #EF;STR DST
   00BD                   1560 ..UPDATE FINGERPRINT
F  00BD F80JA4            1561 UPDTFP: LDI A.0(MOVE);PLO CALL
   00C0 D4939704          1562         SEP CALL,A.0(NL1PNL),A.0(NL2PNL),4
   00C4 D48F9304          1563         SEP CALL,A.0(NLOPNL),A.0(NL1PNL),4
   00C8 D4148F03          1564         SEP CALL,A.0(PVLDCT),A.0(NLOPNL),3
   00CC D40C9201          1565         SEP CALL,A.0(QRSWID),A.0(NLOWID),1
   00D0                   1566 ..REMEMBER WDRS,PPM STATES IN PNLDCT
   00D0 F88FA6E6          1567         LDI A.0(NLOPNL);PLO DST;SEX DST
   00D4 F821A5            1568         LDI A.0(CODWDS);PLO SRC
   00D7 05FEFEFEFE        1569         LDN SRC;SHL;SHL;SHL;SHL
   00DC FACCF155          1570         ANI #CC;OR;STR DST
   00E0                   1571 ..NO ARTIFACT BITS IN FINGERPRINT
   00E0 F891A6            1572         LDI A.0(NLOINP);PLO DST
```

```
     0DE3 05FA7C55         1573            LDN DST;ANI #7C;STR DST
     0DE7                  1574   ..UPDATE CODWDS STACK:
     0DE7 D41A190A         1575            SEP CALL,A.0(CODWDS-7),A.0(CODWDS-8),8
     0DEB                  1576   ..CLEAR CODWDS(T(N)) :
     0DEB F82146F80056     1577            LDI A.0(CODWDS);PLO DST;LDI 0;STR DST
     0DF1                  1578   ..OUTPUT TO CODWDS(CODWDS-1) 4*8 S.S.R. :
     0DF1 25E534           1579            DEC DST;SEX DST;OUT TESTOT
     0DF4                  1580   ..
     0DF4                  1581   ..SHIFT MRKPVC BITS:
     0DF4 F804A6           1582            LDI A.0(MRKPVC);PLO DST
     0DF7 06FE56           1583            LDN DST;SHL;STR DST
     0DFA                  1584   ..SHIFT MRKRUN BITS:
     0DFA F805A6           1585            LDI A.0(MRKRUN);PLO DST
     0DFD 06FE56           1586            LDN DST;SHL;STR DST
     0E00                  1587   ..SHIFT MRKSVT BITS:
     0E00 F806A6           1588            LDI A.0(MRKSVT);PLO DST
     0E03 06FE56           1589            LDN DST;SHL;STR DST
     0E06                  1590   ..SHIFT MRKPRM BITS:
     0E06 F807A6           1591            LDI A.0(MRKPRM);PLO DST
     0E09 06FE56           1592            LDN DST;SHL;STR DST
     0E0C                  1593   ..
     0E0C                  1594   ..TURN ON LATE ARTIFACTS INHIBIT MODE?
     0E0C F80FA5           1595            LDI A.0(LTEBTS);PLO SRC ..T(N-2)=L.L.?
F    0E0F 45FA043200       1596            LDA SRC;ANI #04;BZ QTLLBS
F    0E14 453A00           1597            LDA SRC;BNZ QTLLBS ..ARTBITS=0?
     0E17 F81EA6           1598            LDI A.0(CODWDS-3);PLO DST ..T(N-2) PREM?
F    0E1A 45FA013200       1599            LDA DST;ANI #01;BZ QTLLBS
F    0E1F 06FA023200       1600            LDN DST;ANI #02;BZ QTLLBS ..T(N-1) CP?
     0E24                  1601   ..COUNT UP LATE ARTIFACTS INHIBIT
F    0E24 05FF3E3300       1602            LDN SRC;SMI MAXLL;BPZ QTLLBS
     0E29 05FC4055         1603            LDN SRC;ADI 64;STR SRC
     0E2D                  1604   ..DECR. LTE. ONCE PER BEAT:
     0E2D F81A5            1605  QTLLBS:  LDI A.0(LTUPDN);PLO SRC
F    0E30 053230FF0155     1606            LDN SRC;BZ CKLLBS;SMI 1;STR SRC
     0E36                  1607   ..CHECK IF LTE. CTR. OVER THRESHOLD:
     0E36 F822A6           1608  CKLLBS: LDI A.0(MODCTL);PLO DST
F    0E39 05FF3E3300       1609            LDN  SRC;SMI LTETHR;BPZ ONLLMD
     0E3E                  1610   ..UNDER THRESHOLD. LTE.MODE <- OFF
F    0E3E 05FABF563000     1611            LDN DST;ANI #BF;STR DST;BR ONLLBS
     0E44                  1612   ..
     0E44 05F94056         1613  ONLLMD: LDN DST;ORI #40;STR DST
     0E48                  1614   ..SHIFT LATE BITS & ARTBTS
     0E48 F8E0A6           1615  ONLLBS: LDI A.0(ARTBTS);PLO DST
     0E4B 05FE5626         1616            LDN DST;SHL;STR DST;DEC DST
     0E4F 05FE56           1617            LDN DST;SHL;STR DST
     0E52                  1618   ..
     0E52                  1619   ..STORE TIME OF COMPLETION(TEST)
     0E52 F84A6            1620            LDI A.0(UPDCTM);PLO DST
     0E55 E37133           1621            SEX MPC;DIS,MNEMVE
     0E58 805616           1622            GLO RFT;STR DST;INC DST
     0E5A 90567053         1623            GHI RFT;STR DST;RET,DSTMNE
     0E5F                  1624   ..REQUEST AN EKG RECORD?
     0E5F F8C3A5           1625            LDI A.0(OUTIND);PLO SRC
     0E62 05FAF8C20158     1626            LDN SRC;ANI #F8;LBZ BACKGD
     0E68                  1627   ..IF SJPRA,OR TO BF1,ELSE TO BF2:
     0E68 F80A676          1628  EKGORA: LDI A.0(EKGBF2);PLO DST;SEX DST
F    0E6C 05FA083200       1629            LDN SRC;ANI #08;BZ BF2OR
     0E71 16               1630            INC DST ..DST<- A(EKGBF1)
     0E72 05F156           1631  BF2OR:  LDN SRC;OR;STR DST
     0E75                  1632   ..REQUEST EKG RECORDING! :
     0E75 F8CCA6           1633            LDI A.0(EKGQUE);PLO DST
     0E78 06F90656         1634            LDN DST;ORI #06;STR DST
     0E7C C0015A           1635            LBR BACKGD
     0E7F                  1636   ..................................
     0E7F                  1637   ..SUBROUTINE PNTGR
     0E7F                  1638   ..POINTS GR TO BEAT15(MIN) OR BEAT15*(MIN)
     0E7F                  1639   ..CALLING SEQUENCE:
     0E7F                  1640   ..       LDI A.0(PNTGR);PLO CALL;SEP CALL
     0E7F                  1641   ..PNTGR BEGINNING:
     0E7F 8DA8BDB8         1642  PNTGRB: GLO DAT;PLO GR;GHI DAT;PHI GR
     0E83 EB               1643            SEX GR ..GR = A(MINUTE)
     0E84 8BF4FC07AB       1644            GLO GR;ADD;ADI DSMNBT;PLO GR
F    0E89 C0FEFF           1645            LBR COMPBR-1 ..RETURN
     0E8C                  1646   ..
     0E8C                  1647   ..
     0E8C                  1648   ..
     0E8C                  1649   ..SUBROUTINE CHECK CASSETTE & QUE
```

```
            OE8C                1650  ..CALLING SEQUENCE:
            OE8C                1651  ..      LDI A.0(CKCASQ);PLO CALL;SEP CALL
            OE8C                1652  ..(ENTRY ON SUBROUTINE PAGE)
            OE8C  F8CCA5        1653  DOCKCQ: LDI A.0(EKGQUE);PLO SRC
            OE8F  F8CAA6        1654          LDI A.0(RECTRL);PLO DST
            OE92                1655  ..RECORDING IN PROGRESS?
        F   OE92  06FA01CAFFFF  1656          LDN DST;ANI #01;LBNZ COMPBR-1
            OE98                1657  ..IF ARTSEC>#800,SWITCH LEADS:
            OE98  9088          1658          GHI DAT;PHI GR ..A(MINUTE)->GR
            OE9A  80FC25A8F8    1659          GLO DAT;ADI DSMNAR;PLO GR;SEX GR
            OE9F                1660  ..SWITCH LEADS ON 8MIN. +L.ARTS,
            OE9F                1661  ..OR 5MIN. DURING ZERO'TH PERIOD:
            OE9F  F800B7A7      1662          LDI 0;PHI SUM;PLO SUM
            OEA3  87F4A7        1663  SUMART: GLO SUM;ADD;PLO SUM
            OEA6  97CC00B7      1664          GHI SUM;ADCI 0;PHI SUM
            OEAA  1888FA7FFB40  1665          INC GR;GLO GR;ANI #7F;XRI A.0(ARTSEC+15)
            OEB0  3AA3          1666          BNZ SUMART
            OEB2                1667  ..SUM=TOTAL ARTSEC .GE. #0800 ? :
        F   OEB2  97FF083300    1668          GHI SUM;SMI 8;BPZ STSWAR
            OEB7                1669  ..NO, .GE. #0500 ? :
        F   OEB7  97FF053800    1670          GHI SUM;SMI 5;BM CKPRED
            OEBC                1671  ..YES,ZERO'TH PERIOD?  :
            OEBC  80A828        1672          GLO DAT;PLO GR;DEC GR ..GR<- A(PERIOD)
        F   OEBF  083A00        1673          LDN GR;BNZ CKPRED
            OEC2                1674  ..SET SWITCH LEADS DUE TO ARTIFACTS:
            OEC2  F8F6A6        1675  STSWAR: LDI A.0(OUTCTL);PLO DST
            OEC5  E47144        1676          SEX CALL;DIS,CLLCLL
            OEC8  05F94055      1677          LDN DST;ORI #40;STR DST
            OECC  7084          1678          RET,#84
            OECE                1679  ..EKG HIGHER PRIORITY THAN DATA:
        F   OECE  05CA0000      1680  CKPRED: LDN SRC;LBNZ DOEKGC
            OED2  F8C8A5        1681          LDI A.0(DATQUE);PLO SRC
            OED5                1682  ..DATA BLOCK READY?
        F   OED5  05FA01C20000  1683          LDN SRC;ANI #01;LBZ CKDTCL
            OEDB                1684  ..YES,RECORD:
            OEDB  05FA80        1685          LDN SRC;ANI #80
            OEDE  FC09A8        1686          ADI A.0(WRTRCN);PLO GR
            OEE1  F85AB8        1687          LDI A.1(WRTRCN);PHI GR
            OEE4  F8E9A6        1688          LDI A.0(RECDNO);PHI DST
            OEE7  065818        1689          LDN DST;STR GR;INC GR
            OEEA  FC0156        1690          ADI 1;STR DST ..INCR.RECORD#
            OEED                1691  ..OR(+) SWITCH LEADS TO WRTMOD:
            OEED  F8F6A6        1692          LDI A.0(OUTCTL);PLO DST
            OEF0  05FA40        1693          LDN DST;ANI #40
            OEF3  E8F158        1694          SEX GR;OR;STR GR
            OEF6                1695  ..BKPERD<-PERIOD(*)
            OEF6  F8DBA6        1696          LDI A.0(BKPERD);PLO DST
            OEF9  180856        1697          INC GR;LDN GR;STR DST
            OEFC                1698  ..LLASCT<- LLARTS
            OEFC  88FC48A8      1699          GLO GR;ADI DPOLAR;PLO GR
            OF00  F8E7A6        1700          LDI A.0(LLARTS);PLO DST
            OF03  485818        1701          LDA DST;STR GR;INC GR
            OF06  0658          1702          LDN DST;STR GR
            OF08  F800562655    1703          LDI 0;STR DST;DEC DST;STR DST
            OF0D                1704  ..CLEAR O.B.READY & SET CLEAR WHEN DONE:
            OF0D  05FAFEF90255  1705          LDN SRC;ANI #FE;ORI #02;STR SRC
            OF13                1706  ..SET RECORD IN PROGRESS:
            OF13  F8CAA6        1707          LDI A.0(RECTRL);PLO DST
            OF16  06F90156      1708          LDN DST;ORI #01;STR DST
            OF1A                1709  ..LOAD WRT & A(ENDCHR)
            OF1A  F8C7A6        1710          LDI A.0(ENDCHR);PLO DST
            OF1D  05FA80FC00    1711          LDN SRC;ANI #80;ADI A.0(DATBUF)
            OF22  AAFC5556      1712          PLO WRT;ADI A.0(ENDATA+1);STR DST
            OF26  16            1713          INC DST
            OF27  F85ABA56      1714          LDI A.1(DATBUF);PHI WRT;STR DST
            OF2B                1715  ..ARM RECORD INTERRUPT ROUTINE:
        F   OF2B  F800AC        1716          LDI A.0(RECORD);PLO CPC
        F   OF2E  C0FFFF        1717          LBR COMPBR-1 ..RETURN
            OF31                1718  ..
            OF31                1719  ..CHECK DATA BUFFER CLEAR READY:
        F   OF31  05FA02C2FFFF  1720  CKDTCL: LDN SRC;ANI #02;LBZ COMPBR-1
            OF37                1721  ..REINIT. HEADER,PERIOD & CLEAR BUFFER:
            OF37  F85AB8        1722          LDI A.1(PERIOD);PHI GR
            OF3A  05FA80FC00A8  1723          LDN SRC;ANI #80;ADI A.0(DATBUF);PLO GR
        F   OF40  F800B7        1724          LDI A.1(HDRMSK);PHI SUM
        F   OF43  F800A7        1725          LDI A.0(HDRMSK);PLO SUM
            OF46  475818        1726  DTCLMK: LDA SUM;STR GR;INC GR
            OF49  88FA7F        1727          GLO GR;ANI #7F
```

```
 0F4C  F8083A46        1728            XRI A.0(PERIOD);BNZ DTCLMK
 0F50  F8DBA6          1729            LDI A.0(BKPERD);PLO DST
 0F53  05FC0258        1730            LDN DST;ADI 2;STR GR ..PERIOD
 0F57  1BF80058        1731            INC GR;LDI 0;STR GR ..MINUTE
 0F5B  4858            1732   ZROTBF:  LDA GR;STR GR ..ZERO REST OF BUFFER
 0F5D  83FA7FFB54      1733            GLO GR;ANI #7F;XRI A.0(ENDATA)
 0F62  3A5B            1734            BNZ ZROTBF ..DONE ZEROING?
 0F64                  1735   ..CLEAR DATQUE BUFFER CLEAR READY BIT:
 0F64  05FA7D55        1736            LDN SRC;ANI #7D;STR SRC
F 0F68  C0FFFF          1737            LBR COMPBR-1
 0F6B                  1738   ..
 0F6B                  1739   ..
 0F6B                  1740   ..PROCESS EKG RECORD REQUEST:
 0F6B                  1741   ..(SRC POINTING TO EKGQUE)
 0F6B  F8CDA6          1742   DOEKGC:  LDI A.0(EKGCTR);PLO DST
 0F6E                  1743   ..ANY EKG BLOCKS(3SEC.) LEFT ON CASSETTE
F 0F6E  05C20000        1744            LDN DST;LBZ SHEKQT ..QUIT!
 0F72                  1745   ..START OR CONTINUATION RECORD?
 0F72  05FA07          1746            LDN SRC;ANI #07
F 0F75  FB063A00        1747            XRI #06;BNZ CONTEK ..CONTINUATION!
 0F79                  1748   ..
 0F79                  1749   ..EKG START BLOCK:
 0F79                  1750   ..EKGBGN(WRT)=A(LNGX)-4SECS.
 0F79  E47144          1751            SEX CALL;DIS,#44
 0F7C  8BAA            1752            GLO LNGX;PLO WRT
 0F7E  9B70643A        1753            GHI LNGX;RET,#64;PHI WRT
 0F82                  1754   ..SUBTRACT 5 SECS. FROM POINTER
 0F82  8AFFAFAA        1755            GLO WRT;SMI A.0(MS5500);PLO WRT
 0F85  9A7F02AA        1756            GHI WRT;SMBI A.1(MS5500);PHI WRT
F 0F8A  C00000          1757            LBR DCEKBL ..CONTINUE
 0F8D                  1758   ..
 0F8D                  1759   ..
 0F8D                  1760   ..SHIFT EKGQUE AND QUIT
 0F8D  05FA07F655       1761   SHEKQT:  LDN SRC;ANI #07;SHR;STR SRC
F 0F92  C0FFFF          1762            LBR COMPBR-1 ..QUIT
 0F95                  1763   ..
 0F95                  1764   ..
 0F95                  1765   ..ANOTHER CONTINUATION RECORD?
 0F95  05FA02328D       1766   CONTEK:  LDN SRC;ANI #02;BZ SHEKQT
 0F9A                  1767   ..CALCULATIONS DONE YET?
F 0F9A  05FA80CA0000    1768            LDN SRC;ANI #80;LBNZ CKEKBF ..YES!
 0FA0  05F980355       1769            LDN SRC;ORI #80;STR SRC ..DO NOW!
 0FA4                  1770   ..EKGBGN(WRT)<-ENDCHR+1-MASK LENGTH
 0FA4  F8C7A5          1771            LDI A.0(ENDCHR);PLO SRC
 0FA7  45FF0DAA        1772            LDA SRC;SMI A.0(MSKLTH);PLO WRT
 0FAB  057F00BA        1773            LDN SRC;SMBI 0;PHI WRT
 0FAF                  1774   ..DECREMENT REMAINING EKG BLOCKS:
 0FAF  05FFC156        1775   DCEKBL:  LDN DST;SMI 1;STR DST
 0FB3                  1776   ..CHECK FOR WRT UNDERFLOW
 0FB3  8AFF00          1777            GLO WRT;SMI A.0(LNGBGN)
F 0FB6  9A7F0C3300      1778            GHI WRT;SMBI A.1(LNGBGN);BPZ CAEKND
 0FBB                  1779   ..CORRECT UNDERFLOW
 0FBB  8AFC0DAA        1780            GLO WRT;ADI A.0(LNGLTH);PLO WRT
 0FBF  9A7C04BA        1781            GHI WRT;ADCI A.1(LNGLTH);PHI WRT
 0FC3                  1782   ..A(EKG BLOCK END)<-WRT + 3SEC. + HEADER
 0FC3  8AFC83A7        1783   CAEKND:  GLO WRT;ADI A.0(HD3SEC);PLO SUM
 0FC7  9A7C01B7        1784            GHI WRT;ADCI A.1(HD3SEC);PHI SUM
 0FCB                  1785   ..CHECK FOR SUM OVERFLOW
 0FCB  87FF00          1786            GLO SUM;SMI A.0(LNGEND+1)
F 0FCE  977F603800      1787            GHI SUM;SMBI A.1(LNGEND+1);BM STEKND
 0FD3                  1788   ..CORRECT OVERFLOW:
 0FD3  87FF0DA7        1789            GLO SUM;SMI A.0(LNGLTH);PLO SUM
 0FD7  977F0487        1790            GHI SUM;SMBI A.1(LNGLTH);PHI SUM
 0FDB                  1791   ..ENDCHR<-SUM
 0FDB  F8C7A6          1792   STEKND:  LDI A.0(ENDCHR);PLO DST
 0FDE  875616          1793            GLO SUM;STR DST;INC DST
 0FE1  9756            1794            GHI SUM;STR DST
 0FE3                  1795   ..
 0FE3                  1796   ..CHECK THAT LNGX NOT IN BLOCK(BUFFER)
 0FE3                  1797   .. A(LNGX) .GE. ENDCHR ?
 0FE3  E47144          1798   CKEKBF:  SEX CALL;DIS,#44
 0FE6  8BA7            1799            GLO LNGX;PLO SUM
 0FE8  9B7064          1800            GHI LNGX;RET,#64
 0FEB  B7              1801            PHI SUM
 0FEC                  1802   ..WRT>ENDCHR ? :
 0FEC  26              1803            DEC DST ..DST<-A(ENDCHR)
 0FED  8AF716          1804            GLO WRT;SM;INC DST ..WRT-ENDCHR
```

```
F  OFF0  9A773300                1805           GHI WRT;SMB;BPZ BGTEND ... .LT.
   0FF4                          1806  ..NO,A(LNGX) .GE. ENDCHR?
   0FF4  25                      1807           DEC DST ..DST<- A(ENDCHR)
   0FF5                          1808  ..LNGX-ENDCHR:
   0FF5  87F716                  1809           GLO SUM;SM;INC DST
F  0FF8  9777C30000               1810           GHI SUM;SMB;LBDF EKMVSK
   0FFD                          1811  ..NO,LVGX>WRT?   :
   0FFD  F857A6                  1812  CKLTBG: LDI A.0(SCRSTK);PLO DST
   1000  9773                    1813           GHI SJM;STXD ..SCRSTK-1<-LNGX
   1002  8755                    1814           GLO SJM;STR DST
   1004                          1815  ..WRT-LNGX:
   1004  8AF716                  1816           GLO WRT;SM;INC DST
F  1007  9A773300                1817           GHI WRT;SMB;BPZ EKMVSK
F  100A  C0FFFF                  1818           LBR COMPBR-1 ..QUIT
   100E                          1819  ..
   100E                          1820  ..A(LNGX) .GE. ENDCHR?  :
   100E  25                      1821  BGTEND: DEC DST ..DST<- A(ENDCHR)
   100F  87F716                  1822           GLO SUM;SM;INC DST
   1012  9777C30FFD              1823           GHI SUM;SMB;LBDF CKLTBG
F  1017  C0FFFF                  1824           LBR COMPBR-1 ..QUIT
   101A                          1825  ..
   101A                          1826  ..MOVE MASK TO BUFFER
   101A  8AA7                    1827  EKMVSK: GLO JRT;PLO SUM
   101C  9AB7                    1828           GHI JRT;PHI SUM
F  101E  F800A8                  1829           LDI A.0(HDRMSK);PLO GR
F  1021  F800B8                  1830           LDI A.1(HDRMSK);PHI GR
   1024  485717                  1831  EKMVLP: LDA GR;STR SUM;INC SUM
F  1027  FB593209                1832           XRI #59;BZ EKMVDN
   1029  97F3603A24              1833           GHI SUM;XRI A.1(LNGEND+1);BNZ EKMVLP
   103D  F85CB7                  1834           LDI A.1(LNGBGN);PHI SUM
   1033  F800A73024              1835           LDI A.0(LNGBGN);PLO SUM;BR EKMVLP
   1038                          1836  ..
   1038                          1837  ..MOVE DONE!;START OR CONTINUATION?
   1038  F854A6                  1838  EKMVDN: LDI A.0(SCRSTK-3);PLO DST
   103B                          1839  ..BUT FIRST MOVE RECORD #
   103B  F8E9A5                  1840           LDI A.0(RECONO);PLO SRC
   103E  055616                  1841           LDN SRC;STR DST;INC DST
   1041  FC0155                  1842           ADI 1;STR SRC ..INC RECORD #
   1044  F8CCA5                  1843           LDI A.0(EKGQUE);PLO SRC
F  1047  05FA07F8053A00           1844           LDN SRC;ANI #07;XRI #05;BNZ MVCTCD
   104D                          1845  ..EKG START BLOCK! MOVE CODE
   104D  F8845615                 1846           LDI #84;STR DST;INC DST ..CODE
   1052                          1847  ..MOVE TIME:
   1052  80A89088                1848           GLO DAT;PLO GR;GHI DAT;PHI GR
   1056  284856                  1849           DEC GR;LDA GR;STR DST ..PERIOD
   1059  150856                  1850           INC DST;LDN GR;STR DST ..MINUTE
F  105C  3000                    1851           BR EKMVDT
   105E                          1852  ..
   105E                          1853  ..CONTINUATION BLOCK! MOVE CODE:
   105E  F8925616                1854  MVCTCD: LDI #92;STR DST;INC DST ..CODE
   1062                          1855  ..MOVE EKG CODES(WHICH ALARMS)
   1062  F8CFA5                  1856           LDI A.0(EKGAL2);PLO SRC
   1065  455616                  1857           LDA SRC;STR DST;INC DST ..EKGAL2
   1068  055h                    1858           LDN SRC;STR DST ..EKGAL1
   106A                          1859  ..
   106A                          1860  ..MOVE BYTES TO DELAY BUFFER
   106A  F854A6                  1861  EKMVDT: LDI A.0(SCRSTK-3);PLO DST
   106D  F804A8                  1862           LDI 4;PLO GR
F  1070  3000                    1863           BR EKDTOF
   1072                          1864  ..
F  1072  883200                  1865  EKDTLP: GLO GR;BZ ARMEKG
   1075  46571728                1866           LDA DST;STR SUM;INC SUM;DEC GR
   1079  97F3603A72              1867  EKDTOF: GHI SUM;XRI A.1(LNGEND+1);BNZ EKDTLP
   107E  F85CB7                  1868           LDI A.1(LNGBGN);PHI SUM
   1081  F800A73072              1869           LDI A.0(LNGBGN);PLO SUM;BR EKDTLP
   1085                          1870  ..
   1085  F8CCA5                  1871  ARMEKG: LDI A.0(EKGQUE);PLO SRC
   1089  05FA07F655              1872           LDN SRC;ANI #07;SHR;STR SRC
   108E                          1873  ..UPDATE EKG ALARM CODES:
   108E  F8CFA6                  1874           LDI A.0(EKGAL2);PLO DST
   1091  F8D045                  1875           LDI A.0(EKGBF2);PLO SRC
   1094  455616                  1876           LDA SRC;STR DST;INC DST ..AL2<-BF2
   1097  055616                  1877           LDN SRC;STR DST;INC DST ..AL1<-BF1
   109A  F8005616                1878           LDI 0;STR DST;INC DST ..BF2<-0
   109E  56                      1879           STR DST ..BF1<-0
   109F  F8CA46                  1880           LDI A.0(RECTRL);PLO DST
   10A2  F80156                  1881           LDI 1;STR DST
F  10A5  F400AC                  1882           LDI A.0(RECORD);PLO CPC
```

```
F  10A9 C0FFFF        1883         LBR COMPBR-1
   10A3              1884 ..
   10A3              1885 ..
   10A3              1886 ..
   10A3              1887 ..
   10A3              1888 ..
   10A3 88A5          1889 LOOPFP: GLO SR;PLO SRC
   10AD 45F3FA5F      1890         LDA SRC;XOR;ANI #3F ..(WIDE,PPM)
F  1031 3A0050        1891         BNZ NOMTCH;IRX ..PNLDCD
F  1084 45F33A0060    1892         LDA SRC;XOR;BNZ NOMTCH;IRX ..PLOMRK
F  1089 45F33A0060    1893         LDA SRC;XOR;BNZ NOMTCH;IRX ..INPWRD
   108E              1894 ..WIDTH EQ +OR- RANGE?
   108E 05E3F4        1895         LDN SRC;SEX MPC;ADD
F  10C1 E6F73800      1896         SEX DST;SM;BM NOMTCH
   10C5 05E3F7        1897         LDN SRC;SEX MPC;SM
F  10C8 E6F73300      1898         SEX DST;SM;BPZ NOMTCH
   10CC              1899 ..IF NO SO OR PKD,REQUIRE WORS OR PPM!
   10CC 2D            1900         DEC SRC ..XXXINP
   10CD 05F874FA7C    1901         LDN SRC;XRI #74;ANI #7C
F  10D2 15CAFFFF      1902         INC SRC;L3NZ COPOUT-1 ..S OR PK O
   10D6 252525        1903         DEC SRC;DEC SRC;DEC SRC ..XXXPNL
   10D9 05FAC0        1904         LDN SRC;ANI #C0
   10DC 151515        1905         INC SRC;INC SRC;INC SRC
F  10DF 3200          1906         BZ NOMTCH
F  10E1 C0FFFF        1907         LBR COPOUT-1 ..MATCH RETURN
   10E4              1908 ..
   10E4 87FC04A7      1909 NOMTCH: GLO SJM;ADI 4;PLO SUM
   10E8 FC9BA6        1910         ADI A.0(PV1PNL);PLO DST
   10EB FBBF3AAB      1911         XRI A.0(PV1PNL+36);BNZ LOOPFP
F  10EF 13C0FFFD      1912         INC MPC;LBR BACKUP-3
   10F3              1913 ..  . . . . . . . . . . . . . . .
   1100              1914         PAGE
   1100              1915 ..SUBROUTINE CHECK FINGERPRINT:
   1100              1916 ..CALLING SEQUENCE:
   1100              1917 ..      LDI A.0(CHKFPT);PLO CALL
   1100              1918 ..      SEP CALL,RANGE,A(MATCH)
   1100              1919 ..GR.0=A.0(NLVPNL) ON ENTRY
   1100 F89BA6F5      1920 CHKFPT: LDI A.0(PV1PNL);PLO DST;SEX DST
   1104 F800A7C010A8  1921         LDI 0;PLO SUM;LBR LOOPFP
   110A              1922 ..
   110A              1923 ..
   110A              1924 ..      ******ENTRY FOR PNTGR******
   110A C00E7F        1925 PNTGR: LBR PNTGRB ..PNTGR BEGINNING
   110D              1926 ..
   110D              1927 ..
   110D              1928 ..
   110D              1929 ..      ******ENTRY FOR CKCASQ******
   110D C00E8C        1930 CKCASQ: LBR DOCKCQ ..DO CKCASQ SUBR.
   1110              1931 ..
   1110              1932 ..
   1110              1933 ..
   1110              1934 ..
   1110              1935 ..SUBR COMPBR: BR ON SUM<,=,>LOCN.0,1 CALL.SEQ.:
   1110              1936 ..      LDI A.0(COMPBR);PLO CALL;SEP CALL
   1110              1937 ..      A.0(LOCN.0),A(<),A(=),A(>)
   1110 1313          1938 COPGTE: INC MPC;INC MPC
   1112 43A543A5      1939 COPOUT: LDA MPC;PLO SRC;LDA MPC;PLO MPC
   1116 85B3D3        1940         GLO SRC;PHI MPC;SEP MPC
   1119              1941 ..**********COMPBR ENTRY***********
   1119 43A5E5        1942 COMPBR: LDA MPC;PLO SRC;SEX SRC
   111C 87F7159777    1943         GLO SJM;SM;INC SRC;GHI SUM;SMB
F  1121 CB1123200F    1944         LBNF COPOUT;BZ COEQLO    ..>?NO,=?
   1126 1313          1945 COPGTR: INC MPC;INC MPC
   1128 C01110        1946         LBR COPGTE
   112B              1947 ..
   112B 2587F3        1948 COEQLO: DEC SRC;GLO SUM;XOR
   112E 3228          1949         BZ COPGTR+2 ..LBZ COPGTE
   1130 3026          1950         BR COPGTR
   1132              1951 ..
   1132              1952 ..
   1132              1953 ..SUBR BACKUP  CALLING SEQ.:
   1132              1954 ..      LDI A.0(BACKUP);PLO CALL
   1132              1955 ..      SEP CALL,A(BEATNU)
   1132              1956 ..BACKS LDST<X UP ONE BLOCK
   1132              1957 ..(LOCDE TO LOCDE)
   1132              1958 ..IF BEATBK NOT = BLOCK'S BEATNU,
   1132              1959 ..DOES ERROR RETURN A(BEATNU)
   1132              1960 ..SUM HOLDS NEW BLOCK'S TIME
```

```
  1132 1313       1961         INC MPC;INC MPC  ..NORMAL RETURN
  1134 D3         1962         SEP MPC
  1135            1963 ..******ENTRY FOR BACKUP******
  1135            1964 ..WRAP AROUND?
F 1135 89F8FF3230 1965 BACKUP: GLO LDSTKX;XRI A.0(LDSTKT);BZ BKLDWP
  113A            1966 ..NO,BACKUP ONE BLOCK(TO TIME.0)
  113A 19         1967         INC LDSTKX
  113B 49A7       1968 BKUPTM: LDA LDSTKX;PLO SUM  ..SUM<-TIME.0
  113D 49B7       1969         LDA LDSTKX;PHI SUM  ..SUM<-TIME.1
  113F            1970 ..BEATNO(BLOCK)=BEATBK/
  113F F87F45E5   1971         LDI A.0(BEATBK);PLO SRC;SEX SRC
  1143 49F33232   1972         LDA LDSTKX;XOR;BZ BACKUP-3
  1147 C01112     1973         LBR COPOUT  ..ERROR!!!
  114A            1974 ..
  114A            1975 ..WRAP AROUND TO NEW BLOCK'S TIME.0
  114A F80049     1976 BKLDWP: LDI A.0(LDSTKB);PLO LDSTKX
  114D 303B       1977         BR BKUPTM  ..POINTS TO TIME.0
  114F            1978 ..
  114F            1979 ..
  114F            1980 ..
  114F            1981 ..
  114F            1982 ..
  114F            1983 ..SUBR FORWRD   SAME AS BACKUP,ONLY FORWARD
  114F            1984 ..WRAP AROUND?
F 114F 83F0033200 1985 FORWRD: GLO LDSTKX;XRI A.0(LDSTKB+3);BZ FWLDWP
  1154 89FF07A9303B 1986        GLO LDSTKX;SMI 7;PLO LDSTKX;BR BKUPTM
  115A F8FCA9303B 1987 FWLDWP: LDI A.0(LDSTKT-3);PLO LDSTKX;BR BKUPTM
  115F            1988 ..
  115F            1989 ..
  115F            1990 ..
  115F            1991 ..
  115F            1992 ..SUMBYTE ROUT. : SUM<- 2 BYTE SUM(SINGLE BYTES)
  115F            1993 ..CALL.SEQ.:LDI A.0(SMBYT);PLO CALL
  115F            1994 ..       SEP CALL,A.0(BYTES),#
  115F F80A717B   1995  SMCLBT: LDI 0;PLO SUM;PHI SUM;SKP
  1164 D3         1996         SEP MPC  ..RETURN
  1165 43A5E5     1997 SUMBYT: LDA MPC;PLO SRC;SEX SRC
  1168 43A8       1998         LDA MPC;PLO GR
  116A 88326A     1999 SUMMER: GLO GR;BZ SUMBYT-1 ..DONE?
  116D 87F4A7     2000         GLO SUM;ADD;PLO SUM
  1170 977C0087   2001         GHI SUM;ADCI 0;PHI SUM
  1174 1529306A   2002         INC SRC;DEC GR;BR SUMMER
  1178            2003 ..
  1178            2004 ..
  1178            2005 ..SUBR.MOVE CALL.SEQ.:
  1178            2006 ..      LDI A.0(MOVE);PLO CALL
  1178            2007 ..SEP CALL,A(SOURCE),A(DEST),#LNGTH
  1178            2008 ..SRC,DST,GRK - PARAMETERS
  1178 D3         2009         SEP MPC  ..RETURN
  1179 43A54346   2010 MOVE:   LDA MPC;PLO SRC;LDA MPC;PLO DST
  117D 43A8       2011         LDA MPC;PLO GR
  117F            2012 ..MOVE LOOP:
  117F 88327B     2013 MOVELP: GLO GR;BZ MOVE-1    ..DONE?
  1182            2014 ..NO,DESTIN<- SOURCE
  1182 455616     2015         LDA SRC;STR DST;INC DST
  1185 28307F     2016         DEC GR;BR MOVELP
  1188            2017 ..
  1188            2018 ..
  1188            2019 ..
  1188            2020 ..SUBR.SHFTRT(SHIFT STACK RIGHT) CALL.SEQ.:
  1188            2021 ..      LDI A.0(SHFTRT);PLO CALL
  1188            2022 ..SEP CALL,A.0(SOURCE),A.0(DESTIN),#LNGTH
  1188            2023 ..DESTIN STCK.<- SOURCE S.(SHIFTED RIGHT)
  1188            2024 ..STCKS. LNGTH # ELEM(16BITS/ELEM) LONG
  1188            2025 ..STCK.FORMAT: (STANDARD)
  1188            2026 ..LOC1.0;LOC1.1;HOC2.0;LOC2.1;ETC.
  1188            2027 ..CAUTION:#LNGTH ONLY ONE BYTE!
  1188            2028 ..SRC,DST,GR<- SOURCE,DESTIN,LNGTH
  1188 D3         2029         SEP MPC  ..RETURN
  1189 43A543A6   2030 SHFTRT: LDA MPC;PLO SRC;LDA MPC;PLO DST
  118D 43A8       2031         LDA MPC;PLO GR
  118F 88328B     2032 SHRTST: GLO GR;BZ SHFTRT-1  ..DONE?
  1192            2033 ..1ST CHR LOCN.1,THEN RSHR LOCN.0
  1192 E61616     2034         SEX DST;INC SRC;INC DST
  1195 05F67325   2035         LDN SRC;SHR;STXD;DEC SRC
  1199 457656     2036         LDA SRC;RSHR;STR DST
  119C 1616       2037         INC DST;INC DST
  119E 1528308F   2038         INC SRC;DEC GR;BR SHRTST
```

```
        1142                         2039 ..
        1142                         2040 ..
        1142                         2041 ..SUBR.SHFTLT(SHFTLT=SHFTRT(LEFT))
        1142   D5                    2042        SEP MPC       ..RETURN
        1143                         2043 ..SRC,DST,GR<- SOURCE,DESTIN,LNGTH
        1143   43A54346              2044 SHFTLT: LDA MPC;PLO SRC;LDA MPC;PLO DST
        1147   43A8                  2045        LDA MPC;PLO GR
        1149   883242                2046 SHLTST: GLO GR;BZ SHFTLT-1    ..DONE?
        114C   45FE5616              2047        LDA SRC;SHL;STR DST;INC DST
        1150   457E5616              2048        LDA SRC;SHLC;STR DST;INC DST
        1154   283049                2049        DEC GR;BR SHLTST
        1157                         2050 ..
        1157                         2051 ..
        1157                         2052 ..
        1157                         2053 ..SUBR. STKSUM : CALL.SEQ.:
        1157                         2054 ..       LDI A.0(STKSUM);PLO CALL
        1157                         2055 ..       OR
        1157                         2056 ..       LDI A.0(CLRSUM);PLO CALL
        1157                         2057 ..SEP CALL,A.0(STACK),#LNGTH
        1157                         2058 ..(STANDARD STACK FORMAT)
        1157                         2059 ..SUM<- 0
        1157   F800478738            2060 CLRSUM: LDI 0;PLO SUM;PHI SUM;SKP
        115C   D5                    2061        SEP MPC       ..RETURN
        115D                         2062 ..SRC,GR<- A(STACK,#LNGTH
        115D   43A5E5                2063 STKSUM: LDA MPC;PLO SRC;SEX SRC
        11C0   43A8                  2064        LDA MPC;PLO GR
        11C2                         2065 ..SUM<- STACK CUM + SUM
        11C2   88323C                2066 ADDX:  GLO GR;BZ STKSUM-1   ..DONE?
        11C5                         2067 ..FIRST ADD LOCN.0,THEN ADC LOCN.1 TO SUM :
        11C5   87F4A7                2068        GLO SUM;ADD;PLO SUM
        11C8   15977487              2069        INC SRC;GHI SUM;ADC;PHI SUM
        11CC   152830C2              2070        INC SRC;DEC GR;BR ADDX
        11D0                         2071 ..
        11D0                         2072 ..
        11D0                         2073 ..
        11D0                         2074 ..DETECTION ALGORITHM SUBROUTINE
        11D0                         2075 ..CALLING SEQ.: LDI A.0(DETALG);PLO CALL
        11D0                         2076 ..        SEP CALL,A.0(CODWDS-N),A,0(TABLE)
        11D0                         2077 ..GR.1 MUST CONTAIN A.1(TABLE)
        11D0                         2078 ..ROUTINE FALLS THROUGH ON NO ALARM
        11D0                         2079 ..TABLE FORMAT:
        11D0                         2080 ..,(MASK,DATA),(MASK,DATA)
        11D0                         2081 ..,MODE,A(ALARM)
        11D0                         2082 ..
        11D0   D5                    2083        SEP MPC    ..RETURN
        11D1                         2084 ..*************ENTRY FOR DETALG*************
        11D1   43A5                  2085 DETALG: LDA MPC;PLO SRC
        11D5   43A8E8                2086        LDA MPC;PLO GR;SEX GR
F       11D8   C00008                2087        LBR DETALP
        11DB                         2088 ..
        11DB                         2089 ..
        11DB                         2090 ..IS MODE DISABLEING?
        11DB   45F2CA11D0            2091 ALARM:  LDA SRC;AND;LBNZ DETALG-1
        11E0                         2092 ..A(ALARM) ->MPC:
        11E0   607237372A3           2093        IRX;LDXA;PHI MPC;LDXA;PLO MPC
        11E3   C011D0                2094        LBR DETALG-1
        11E6                         2095 ..
        11E6                         2096 ..DONE?
        11E6   85FB2232C9            2097 DETALP: GLO SRC;XRI A.0(MODCTL);BZ ALARM
F       11EB   F0FA9CF81CC2000D 2098        LDX;ANI #9C;XRI #1C;LBZ TRECHG
F       11F3   F0FA9CF814C20000 2099        LDX;ANI #9C;XRI #14;LBZ TWOCHG
F       11FB   F0FA9CF043200     2100        LDX;ANI #9C;XRI #04;BZ ONECHG
F       1202   45F260F33A00      2101 ZERCHG: LDA SRC;AND;IRX;XOR;BNZ DETRET
        1208   60C011E6              2102        IRX;LBR DETALP
        120C                         2103 ..
F       120C   05FA9C3200            2104 ONECHG: LDN SRC;ANI #9C;BZ DETRET
        1211   45FA633003            2105        LDA SRC;ANI #63;BR ZERCHG+1
        1215                         2106 ..
F       1215   05FA1C3200            2107 TWOCHG: LDN SRC;ANI #1C;BZ DETRET
F       121B   05FA8C3200            2108        LDN SRC;ANI #8C;BZ DETRET
F       1220   05FA943200            2109        LDN SRC;ANI #94;BZ DETRET
        1225   05FA98SA0C            2110        LDN SRC;ANI #98;BNZ ONECHG
        122A   C011D0                2111 DETRET: LBR DETALG-1
        122D                         2112 ..
        122D   05FA98FB98320C        2113 TRECHG: LDN SRC;ANI #98;XRI #98;BZ ONECHG
        1234   05FA9CFB1C320C        2114        LDN SRC;ANI #9C;XRI #1C;BZ ONECHG
        123B   05FA9CFB8C            2115        LDN SRC;ANI #9C;XRI #8C
        1240   320C                  2116        BZ ONECHG
```

```
         1242 05FA9CF894          2117           LDN SRC;ANI #9C;XRI #94
         1247 320C                2118           BZ ONECHG
         1249 C01130              2119           LBR DETALG-1
         124C                     2120  ...........................................
         124C                     2121  ..MEDICAL CONCEPTS INC.
         124C                     2122  ..INTERRUPT ROUTINE   COPYRIGHT:30OCT78
         124C F8E9A6              2123  VFIB:    LDI A.0(CTRVFB);PLO ADR
         124F 05CEFC0156           2124          LDN ADR;LSZ;ADI 1;STR ADR
         1254 1605FC0155          2125           INC ADR;LDN ADR;ADI 1;STR ADR
F        1259 02FA03CA0000        2126           LDN STK;ANI #03;LBNZ MONITR
F        125F 06FF143300          2127           LDN ADR;SMI 20;BPZ CKVFIB
F        1264 F80056C00000        2128           LDI 0;STR ADR;LBR MONITR ..CTRVRF<-0
         126A                     2129  ..
F        126A 26465A00            2130  CKVFIB:  DEC ADR;LDA ADR;BNZ ONVFIB
         126E 062656              2131           LDN ADR;DEC ADR;STR ADR
F        1271 15F8055C00000       2132           INC ADR;LDI 0;STR ADR;LBR MONITR
         1278                     2133  ..
         1278 F823A6              2134  ONVFIB:  LDI A.0(MO2CTL);PLO ADR
F        127B 05F9805C000000      2135           LDN ADR;ORI #80;STR ADR;LBR MONITR
         1282                     2136  ...........................................
         1282 DF                  2137  DOFUNC:  SEP PPC
         1283                     2138  ..RESTORE LOST<X,0,ADR,0,DF,0;RETURN
         1283 E26072A9            2139  QUIT:    SEX STK;IRX;LDXA;PLO LOSTKX
         1287 72A5                2140           LDXA;PLO SRC
         1289 72A6727E            2141           LDXA;PLO ADR;LDXA;SHLC
         128D 7270                2142           LDXA;RET
         128F                     2143  ..       ********INTRPT.ROJT.ENTRY POINT********
         128F 227922              2144  INTRPT:  DEC STK;SAV;DEC STK ..SAVE T
         1292 737573              2145           STXD;SHRC;STXD ..SAVE D,DF
         1295 8673                2146           GLO ADR;STXD ..SAVE ADR
         1297 8573                2147           GLO SRC;STXD ..SAVE SRC
         1299 8973                2148           GLO LOSTKX;STXD ..SAVE LOSTKX
         129B                     2149  ..STK POINTS TO LOCDE
         129B 102E                2150           INC RET;DEC CLK ..+1MS
         129D                     2151  ..WHICH ROUT.?  :
F        129D 8EFA073200          2152           GLO CLK;ANI #07;BZ ADELAY ..8MS.
         12A2 FA03F802324C        2153           ANI #03;XRI #02;BZ VFIB ..4MS.
F        12A8 8EFBF4C20000        2154           GLO CLK;XRI #F4;LBZ DATACC ..256MS.
F        12AE FB10C20000          2155           XRI #10;LBZ ARTINT ..256MS.
         12B3 DC                  2156           SEP CPC ..MORE THAN EVERY 2MS.
FF       12B4 3400C00000          2157           BI LLDART;LBR MONITR ..REFRAC?
         12B9                     2158  ...........................................
         12B9                     2159  ..LOW LEVEL DETECT ARTIFACTS ROUTINE:
         12B9 F83A6E6             2160  LLDART:  LDI A.0(OLLD);PLO ADR;SEX ADR
         12BD                     2161  ..LOW LEVEL DETECT SAME AS BEFORE?
F        12BD 02FA0CF3C20000      2162           LDN STK;ANI #0C;XOR;LBZ MONITR
         12C4 F373                2163           XOR;STXD ..SAVE NEW L.L.DET.
         12C6 F0FC0156            2164           LDX;ADI 1;STR ADR ..INCR. LLDCTR
F        12CA F30CCA0000          2165           XRI 12;LBNZ MONITR ..12 CHANGES?
         12CF F817A6              2166           LDI A.0(IN8FWD);PLO ADR ..LLART<-ON
         12D2 05F90156            2167           LDN ADR;ORI #01;STR ADR
F        12D6 C00000              2168           LBR MONITR ..CONTINUE
         12D9                     2169  ...........................................
         12D9                     2170  ..LOAD LONG DELAY INDEX:
         12D9 F85CBB              2171  LDLNGX:  LDI A.1(LNGBGN);PHI LNGX
F        12DC F80AB3000           2172           LDI A.0(LNGBGN);PLO LNGX;BR GETADC
         12E1                     2173  ..
         12E1                     2174  ..WRAP AROUND SHORT DELAY INDEX
F        12E1 F8EA55C00000        2175  SHTLDE:  LDI A.0(SHTBGN);STR SRC;LBR PUTSHT
         12E7                     2176  ..
         12E7                     2177  ..ANALOG DELAY ROUTINE:
         12E7 9BFB503209          2178  ADELAY:  GHI LNGX;XRI A.1(LNGEND+1);BZ LDLNGX
         12EC                     2179  ...........................................
         12EC                     2180  ..PATCH OVER FOR RECORD VERSION/
         12EC                     2181  ...........................................
I        12EC EB60                2182  GETADC:  SEX LNGX;OUT LGALGD ..TEMPORARY
         12EE 2B68                2183           DEC LNGX;INP ADCONV
         12F0 F8F4A5              2184           LDI A.0(SHTSVR);PLO SRC
         12F3 05A5E6              2185           LDN SRC;PLO DST;SEX DST
         12F6 61                  2186           OUT SHALGD ..X(DST)=SHORT DELAY
         12F7 86FBF4C212E1        2187           GLO DST;XRI A.0(SHTEND+1);LBZ SHTLDE
         12FD 8655                2188           GLO DST;STR SRC
         12FF                     2189  ..NEW INPUT-->SHORT DELAY BUFFER
         12FF 264356              2190  PUTSHT:  DEC DST;LDA LNGX;STR DST
         1302                     2191  ..WAS INPUT OUT OF RANGE?
FF       1302 3208FBFF3A00        2192           BZ TOOBIG;XRI #FF;BNZ MONITR
         1308 F822A6              2193  TOOBIG:  LDI A.0(MODCTL);PLO DST
```

```
F  1303  06FA083A00     2194          LDN DST;ANI #08;BNZ MONITR ..STARTUP?
   1310  F8F6A6F6        2195          LDI A.0(OUTCTL);PLO DST;SEX DST
   1314  06F90256        2196          LDN DST;ORI #02;STR DST
   1318  63              2197          OUT OUTSIG
   1319                  2198   ........................................
   1319                  2199   ..MONITOR ROUT. :
   1319  F88346          2200   MONITR: LDI A.0(SVSTKX);PLO ADR
   131C  06A9            2201          LDN ADR;PLO LDSTKX  ..RESTORE LDSTKX
   131E                  2202   ..LD=LD(T(N-1))?
   131E  E96DFA0F59      2203          SEX LDSTKX;INP LD;ANI #0F;STR LDSTKX
F  1323  02F33200        2204          LDN STK;XOR;BZ LDREP
   1327                  2205   ..NOT REPEAT,SAVE LDCDE,STORE BEATNU & TIME:
   1327  0952            2206          LDN LDSTKX;STR STK  ..SAVE NEW LDCDE
   1329  2922            2207          DEC LDSTKX;DEC STK
   132B                  2208   ..STORE BEATNU & STK<- A(LDCDE)
   132B  4273            2209          LDA STK;STXD
   132D  90738073        2210          GHI RFT;STXD;GLO RFT;STXD
   1331                  2211   ..FORCE NO WRAP AROUND(SAME PAGE)
   1331  F85939          2212          LDI A.1(LDSTKT);PHI LDSTKX
   1334  895BC01292      2213   SVLDPT: GLO LDSTKX;STR ADR;LBR DOFUNC
   1339                  2214   ..
   1339                  2215   ..
   1339                  2216   ..LD REPEAT!
   1339  3C3B            2217   LDREP: BN1 *-3      ..BREF?
   133B                  2218   ..PLD,VLD=0?
   133B  02FA03C212B2    2219          LDN STK;ANI #03;LBZ DOFUNC
   1341                  2220   ..PLD,VLD=1,START REFRAC:
   1341  E2              2221          SEX STK    ..INCR BEATNU:
   1342  22FCFC0173      2222          DEC STK;LDX;ADI 1;STXD
   1347                  2223   ..SAVE REFRAC ADDR.:
   1347  22895212        2224          DEC STK;GLO LDSTKX;STR STK;INC STK
   134B                  2225   ..REFRACK<- 1,CLEAR OUTSIGS
   134B  F0FAC0F911      2226          LDX;ANI #C0;ORI #11
   1350  5265F0          2227          STR STK;OUT OUTSIG;IRX
   1353                  2228   ..RFT<- 0,RESET FPC
   1353  F8F2A6          2229          LDI A.0(LLDCTR);PLO ADR
   1356  F800A0B0AF      2230          LDI 0;PLO RFT;PHI RFT;PLO FPC
   135B  56C01283        2231          STR ADR;LBR QUIT
   135F                  2232   ........................................
F  135F  9FFA073200      2233   ARTINT: GHI CLK;ANI #07;BZ UPDOWN ..2SECS.
F  1364  FA013200        2234          ANI #01;BZ CKLLUP
   1368  F801A6          2235   DECFAG: LDI A.0(ARTFAG);PLO ADR
   136B  06F656          2236          LDN ADR;SHR;STR ADR ..512MS.
   136E  3019            2237          BR MONITR
   1370                  2238   ..
   1370                  2239   ..COUNT L.L.ARTS. UP?  :
   1370  F822A6          2240   CKLLUP: LDI A.0(MODCTL);PLO ADR
   1373  06FA03FB013A19  2241          LDN ADR;ANI #03;XRI #01;BNZ MONITR
   137A  F8E7A6          2242          LDI A.0(LLARTS);PLO ADR
   137D  06FC0156        2243          LDN ADR;ADI 1;STR ADR
   1381  16              2244          INC ADR ..ADR<- LLARTS.1
   1382  067C0056        2245          LDN ADR;ADCI 0;STR ADR
   1386  3019            2246          BR MONITR
   1388                  2247   ..
   1388  F801A6          2248   UPDOWN: LDI A.0(ARTFAG);PLO ADR
F  138B  063200          2249          LDN ADR;BZ DOWNCT ..ARTFAG=0?
   138E                  2250   ..NO! COUNT UP :
   138E  26              2251          DEC ADR ..A.0(UPDNCT)->ADR
   138F  06FF543319      2252          LDN ADR;SMI FULLCT;BDF MONITR
   1394  F822A6          2253          LDI A.0(MODCTL);PLO ADR
   1397  06FA023219      2254          LDN ADR;ANI #02;BZ MONITR
   139C                  2255   ..COUNT UP UPDNCT
   139C  F800A6          2256          LDI A.0(UPDNCT);PLO ADR
   139F  06FC03563019    2257          LDN ADR;ADI #03;STR ADR;BR MONITR
   13A5                  2258   ..
   13A5                  2259   ..
   13A5  2606            2260   DOWNCT: DEC ADR;LDN ADR ..A.0(UPDNCT)->ADR
   13A7                  2261   ..ABOVE OR BELOW HALFCT THRESHOLD?
F  13A7  FF2A3300        2262          SMI HALFCT;BPZ OVERTH
   13AB                  2263   ..BELOW THRESHOLD :
   13AB  063219FF0156    2264          LDN ADR;BZ MONITR;SMI #01;STR ADR
   13B1  3019            2265          BR MONITR
   13B3                  2266   ..
   13B3  06FF03563019    2267   OVERTH: LDN ADR;SMI #03;STR ADR;BR MONITR
   13B9                  2268   ........................................
   13B9                  2269   ..DATA ACCUMULATION,TIME OF DAY ROUTS.
   13B9                  2270   ..ON ENTRY DAT POINTS TO MINUTE(MINUTE*)
```

```
F  1389  9E3200              2271  DATACC: GHI CLK;BZ CK15MN
   138C  F822A6              2272          LDI A.0(MODCTL);PLO ADR
F  138F  06FA0A3A00          2273          LDN ADR;ANI #0A;BNZ UPARTS
   13C4                      2274  ..NO H.L.ARTS. OR START, DECR NARTSEC:
   13C4  F803A6              2275          LDI A.0(NARTSC);PLO ADR
   13C7  063219              2276          LDN ADR;BZ MONITR
   13CA  FF01563019          2277          SMI 1;STR ADR;BR MONITR
   13CF                      2278  ..
   13CF  ED                  2279  UPARTS: SEX DAT ..DAT=A(MINUTE)
   1300                      2280  ..DAT<- A(ARTSEC)=A(MINUTE)+MINUTE+37
   1300  80F4FC25A0          2281          GLO DAT;ADD;ADI DSMNAR;PLO DAT
   1305  0DFC0159            2282          LDN DAT;ADI 1;STR DAT ..INCR ARTSEC
   1309                      2283  ..POINT DAT BACK TO MINUTE(MINUTE')
   1309                      2284  ..NOTE: A(MINJTE')=A(MINUTE'+#80)
   1309  80FA80FC80A0        2285          GLO DAT;ANI #80;ADI A.0(MINUTE);PLO DAT
   130F  3019                2286          BR MONITR
   13E1                      2287  ..
   13E1                      2288  ..
   13E1                      2289  ..CHECK 15 MINUTES(PERIOD DONE?)
F  13E1  0DFB0E5200          2290  CK15MN: LDN DAT;XRI 14;BZ YES15M ..15MIN?
   13E5                      2291  ..NO,COUNT A MINUTE:
   13E6  0DFC0159            2292          LDN DAT;ADI 1;STR DAT
   13EA                      2293  ..REINIT SECOND TIMER :
   13EA  F8EABE              2294          LDI SECS60;PHI CLK
   13ED                      2295  ..REINIT NARTSC:
   13ED  F803A6              2296          LDI A.0(NARTSC);PLO ADR
   13F0  F83856              2297          LDI SECS15;STR ADR
   13F3  3019                2298          BR MONITR
   13F5                      2299  ..
   13F5                      2300  ..15MINUTES: SET WRITE DATA FLAG:
   13F5  F8C9A6              2301  YES15M: LDI A.0(DATQUE);PLO ADR
   13F8  80FA80              2302          GLO DAT;ANI #80 ..DATBUF OR DATBUF'
   13FB  F90156              2303          ORI #01;STR ADR ..QUE DATA
   13FE                      2304  ..SWITCH BUFFERS:
   13FE  80FB80A0            2305          GLO DAT;XRI #80;PLO DAT
   1402                      2306  ..REINIT. SECOND TIMER
   1402  F8EABE              2307          LDI SECS60;PHI CLK
   1405  F803A6              2308          LDI A.0(NARTSC);PLO ADR
   1408  F83856              2309          LDI SECS15;STR ADR
P  140B  3019                2310          BR MONITR
   140D                      2311  ..***************************************
   140D                      2312  ..WRITE CASSETTE INTERRUPT ROUTINE:
   140D                      2313  ..ROUTINE ENTERED EVERY 1MS
   140D  D1300D              2314  NORECD: SEP IPC;BR NORECD ..NO RECORD
   1410                      2315  ..
   1410                      2316  ..CASSETTE <-START FORWARD
   1410  F8C9A6              2317  RECORD: LDI A.0(CASCTL);PLO DST
   1413  F80E56              2318          LDI WRITE;STR DST
   1416  E666                2319          SEX DST;OUT CASOUT
   1418  D1                  2320          SEP IPC
   1419                      2321  ..
   1419                      2322  ..WAIT 200MS (STARTUP TIME)
   1419  F802A6              2323          LDI A.0(TIMER);PLO DST
   141C  F8C856              2324          LDI 200;STR DST
   141F  D1                  2325  CA200L: SEP IPC
   1420  F802A6              2326          LDI A.0(TIMER);PLO DST
   1423  06FF0156            2327          LDN DST;SMI 1;STR DST
   1427  3A1F                2328          BNZ CA200L
   1429                      2329  ..
   1429                      2330  ..WRITE DATA TO CASSETTE UNTIL DONE:
   1429  D17B                2331          SEP IPC;SEQ
   142B  D1372B              2332  CANIB1: SEP IPC;B4 CANIB1 ..LEAST SIG.NIBBLE
   142E                      2333  ..HANDLE DELAY BUFFER WRAP AROUND:
F  142E  9AFB603A00          2334          GHI WRT;XRI A.1(LNGEND+1);BNZ NIB1OK
   1433  F8CBBA              2335          LDI A.1(LNGBGN);PHI WRT
   1436  EA622A              2336  NIB1OK: SEX WRT;OUT FIFO;DEC WRT
   1439  D13739              2337  CANIB2: SEP IPC;B4 CANIB2 ..MOST SIG.NIBBLE
   143C  EAF0                2338          SEX WRT;LDX
   143E  F6F6F6F6            2339          SHR;SHR;SHR;SHR
   1442  5A62                2340          STR WRT;OUT FIFO
   1444  F8C7A5E5            2341          LDI A.0(ENDCHR);PLO SRC;SEX SRC
   1448  8AF33A2C            2342          GLO WRT;XOR;BNZ CANIB1+1
   144C  609AF33A2C          2343          IRX;GHI WRT;XOR;BNZ CANIB1+1
   1451                      2344  ..
   1451  F814AA              2345  FLFIFO: LDI 20;PLO WRT ..FLUSH FIFO
   1454  D13754              2346  FIFLOP: SEP IPC;B4 FIFLOP
F  1457  8A3200              2347          GLO WRT;BZ CASTOP
```

```
145A 2AEC62FF        2346            DEC WRT;SEX CPC;OUT FIFO,#FF
145E 3059            2349            BR FIFLOP
1460                 2350    ..
1460                 2351    ..DONE! STOP CASSETTE,SIGNAL BACKGROUND:
1460 017A01          2352    CASTOP: SEP IPC;REQ;SEP IPC
1463 F8C9A6          2353            LDI A.0(CASCTL);PLO DST
1465 F81F56          2354            LDI STOPW;STR DST
1469 E566            2355            SEX DST;OUT CASOUT
146A D1              2356            SEP IPC
146C                 2357    ..WAIT 150MS (BREAKING TIME)
146C F8D2A6          2358            LDI A.0(TIMER);PLO DST
146F F89656          2359            LDI 150;STR DST
1472 D1              2360    CA150E: SEP IPC
1473 F8D2A6          2361            LDI A.0(TIMER);PLO DST
1476 06FF0156        2362            LDN DST;SMI 1;STR DST
147A 3A72            2363            BNZ CA150E
147C                 2364    ..TURN OFF CASSETTE:
147C D1              2365            SEP IPC
147D F8C9A6          2366            LDI A.0(CASCTL);PLO DST
1480 F81456          2367            LDI OFF;STR DST
1483 E666            2368            SEX DST;OUT CASOUT
1485                 2369    ..SIGNAL BACKGROUND CASSETTE READY:
1485 D1              2370            SEP IPC
1486 F8CAA6          2371            LDI A.0(RECTRL);PLO DST
1489 06F4FE56        2372            LDN DST;ANI #FE;STR DST
148D C0140D          2373            LBR NORECO
1490                 2374    ..........................
1490                 2375    ..
1490 AAAAAAAA        2376    HORMSK: .X'AAAAAAAA'
1494 FEFC0203590001  2377            .X'FEFC0203590001'
149B 0000            2378            .X'0000'
149D                 2379    ..........................
149D 9A009A009A009A00 2380  NRMLSU: .X'9A009A009A009A0000',A(CLRVFB)
14A8 980000009800000  2381  BIGMSU: .X'98000000980000000'
14B0 98000000980000001 2382          .X'9800000098000000',A(CLRVFB)
14B9 98009A0000009800 2383  TRIGSU: .X'98009A0000009800'
14C1 9A000001BE      2384            .X'9A0000',A(CLRVFB)
14C6                 2385    ..
1500                 2386            PAGE
1500 010017010302950A 2387  PVCAUT: .X'010017010302950',A(STPVC)
1509 9C0035219E008B0A 2388  PVCI1T: .X'9C0035219E008B0',A(SJMPVC)
1512 01000701030203A0A 2389 PVCATB: .X'010007010302BA',A(STPVC)
151B 0100170101008B0A 2390  PVCBTB: .X'010017010100BB',A(STPVC)
1524 0100140003028A0A 2391  PVCCTB: .X'010014000302BA',A(STPVC)
152D 01001C0001008B0A 2392  PVCDTB: .X'01001C000100BB',A(FLGPVC)
1536 1C0003009F0A98   2393  PVCDUT: .X'1C0000009F',A(STPVC)
153D 888800009B0A81   2394  PVCETB: .X'888800009B',A(FLGPVC)
1544 9C000000820A31   2395  ENDRUN: .X'9C00000082',A(OFFRUN)
154B 140000090D       2396  RUN2CH: .X'140000',A(UPDTFP)
1550 07011400900088DA 2397  RUN1TB: .X'070114009D008B',A(STRUNS)
1559 0701060002028B0A 2398  RUN2TB: .X'070106000202BB',A(STRUNS)
1562 140007010202B80A 2399  RUN3TB: .X'1400070102020B',A(STRUNS)
156B 1400140014008B0A 2400  RUN4TB: .X'140014001400BB',A(STRUNS)
1574 4040404000000980A 2401 RUN5TB: .X'404040400000098',A(STRUNS)
157D 05010501050105  2402  RUN7TB: .X'05010501050105018B',A(STRUNS)
1588 1C001C0000009B0A 2403 RUN8TB: .X'1C001C0000009B',A(STRUNS)
1591 04009C0004003C00 2404  BIGMTD: .X'04009C0004003C0004009C00'
1599 0400000098A9B03  2405          .X'040000009A',A(BIGPVC)
15A4 40404000404040009 2406 BIGM2D: .X'40404000404040040'
15AF 40004040000098000 2407          .X'40004040000098',A(BIGPVC)
15B7 9D009D019D009A0B 2408  SVEBTB: .X'9D009D019D009A',A(STSVEB)
15C0 9C009D019D019A0B 2409  SVTB:   .X'9C009D019D019A',A(STSVT)
15C9 9C00040005019C00 2410  TWAVET: .X'9C0004005019C0000',A(PVCTWV)
15D4 8C002420020049A07 2411 TWAVNT: .X'8C002420020049A',A(NRMLTW)
15DD 9C005010501900000 2412 CPLTB:  .X'9C0050105019C00000000',A(STCPL)
15EA 900100001208000  2413  UR1TB:  .X'9001000012',A(URUPCT)
15F1 9C00020212080000 2414  UR2TB:  .X'9C0002021',A(URUPCT)
15F8 9000200120707    2415  URM3TB: .X'9000200120',A(URMDCT)
15FF                 2416   ..........................
15FF                 2417   ..DOFUNC ROUTINES (FUNCTIONS PERFORMED AT
15FF                 2418   ..SPECIFIC TIMES AFTER DETECTION OF A
15FF                 2419   ..QRS COMPLEX)
15FF                 2420   ..
15FF                 2421   ..
1600                 2422           PAGE
1600 D1903A00         2423  MSBGN:  SEP IPC;GHI RFT;BNZ MSBGN
1604                 2424    ..
1604 D1              2425    MS1:   SEP IPC
```

```
1605 F8BFA6        2426            LDI A.0(SVLNGX);PLO ADR
1608 835616        2427            GLO LNGX;STR ADR;INC ADR
160B 9B56          2428            GHI LNGX;STR ADR
160D                2429 ..
160D                2430 ..READ LOW LEVEL ARTS BEFORE QRS! :
160D 01            2431 MS2:     SEP IPC
160E F81646E6      2432            LDI A.0(INPWRD);PLO ADR;SEX ADR
1612 6C60          2433            INP 4;ASIG;IRX
1614 FA01F173      2434            ANI #01;OR;STXD
1618                2435 ..
1618                2436 ..
1618 01            2437 MS119:   SEP IPC
1619 80F3773A18    2438            GLO RFT;XRI 119;BNZ MS119
161E                2439 ..
161E 01            2440 MS120:   SEP IPC
161F                2441 ..BTRSP<-OFF
161F F8F6A6        2442            LDI A.0(OUTCTL);PLO ADR
1622 06FAEF56      2443            LDN ADR;ANI #EF;STR ADR
1626 E565          2444            SEX ADR;OUT OUTSIG
1628                2445 ..
1628                2446 ..
1628 01            2447 MS159:   SEP IPC       ..RETURN
1629 80FB9F3A28    2448            GLO RFT;XRI 159;BNZ MS159
162E                2449 ..
162E 01            2450 DIM160:  SEP IPC
162F                2451 ..160MS. TURN ON DIMINISHED SENSITIVITY
162F F8F6A6E6      2452            LDI A.0(OUTCTL);PLO ADR;SEX ADR
1633 06F9085665    2453            LDN ADR;ORI #08;STR ADR;OUT OUTSIG
1638                2454 ..
1638                2455 ..
1638 01            2456 MS198:   SEP IPC
1639 80F4C63A38    2457            GLO RFT;XRI 198;BNZ MS198
163E                2458 ..
163E                2459 ..IF TOOBIG=1,INHIBIT AGCA:
163E 01            2460 MS199:   SEP IPC
163F F8F6A6        2461            LDI A.0(OUTCTL);PLO ADR
F 1642 06FA023A00  2462            LDN ADR;ANI #02;BNZ MS201
1647                2463 ..
1647                2464 ..MS200  AGCA<- ON
1647 01            2465            SEP IPC
1648 F8F6A6        2466            LDI A.0(OUTCTL);PLO ADR
164B 06F92056      2467            LDN ADR;ORI #20;STR ADR
164F E565          2468            SEX ADR;OUT OUTSIG
1651                2469 ..
1651 01010101      2470 MS201:   SEP IPC;SEP IPC;SEP IPC;SEP IPC
1655                2471 ..
1655                2472 ..MS204  AGCA<-OFF
1655 F8F6A6        2473            LDI A.0(OUTCTL);PLO ADR
1658 06FADF56      2474            LDN ADR;ANI #DF;STR ADR
165C E665          2475            SEX ADR;OUT OUTSIG
165E                2476 ..
165E                2477 ..
165E 01            2478 MS213:   SEP IPC   ..RETURN
165F 80F3053A5E    2479            GLO RFT;XRI 213;BNZ MS213
1664                2480 ..
1664                2481 ..
1664 01            2482 MS214:   SEP IPC
1665                2483 ..IF RJNS ON DISABLE PRE4:
1665 F82246        2484            LDI A.0(MODCTL);PLO ADR
F 1668 06FA103A00  2485            LDN ADR;ANI #10;BNZ MS217
166D                2486 ..
166D                2487 ..
166D 01            2488 MS215:   SEP IPC        ..(RETURN)
166E                2489 ..IF PREM,DISABLE PRE4:
166E F82146        2490            LDI A.0(CODWDS);PLO ADR
F 1671 06FA013A00  2491            LDN ADR;ANI #01;BNZ MS217
1676                2492 ..
1676 01            2493 PRE4:    SEP IPC        ..(RETURN)
1677                2494 ..216MS. TURN ON PRE4 SIGNAL
1677 F8F6A6E6      2495            LDI A.0(OUTCTL);PLO ADR;SEX ADR
167B 06F9045665    2496            LDN ADR;ORI #04;STR ADR;OUT OUTSIG
1680                2497 ..
1680                2498 ..A.1(BKLNGX)<-A.1(SVLNGX)
1680 01            2499 MS217:   SEP IPC
1681 F8C0A6        2500            LDI A.0(SVLNGX+1);PLO ADR
1684 461356        2501            LDA ADR;INC ADR;STR ADR
1687                2502 ..A.0(BKLNGX)<-A.0(SVLNGX)
1687 01            2503 MS218:   SEP IPC
```

```
1689 F8BFA6        2504            LDI A.3(SVLNGX);PLO ADR
1683 461556        2505            LDA ADR;INC ADR;STR ADR
1685               2506  ..
1685 01            2507            SEP IPC         ..(RETURN)
169F               2508  ..21943.: READ & CLEAR CHARLIE'S SIGNALS
168F F815A656      2509            LDI A.3(INPWRD);PLO ADR;SEX ADR
1693 6363          2510            INP CHASIG;OUT CLCHAS
1695 FAFE          2511            ANI #FE   ..NO L.L.ARTS.DURING QRS!
1697 F16073        2512            OR;IRX;STXD ..(NO L.L.ART.)
169A F80073        2513            LDI 0;STXD
169D               2514  ..
169D 01            2515  OFFREF: SEP IPC         ..(RETURN)
169E               2516  ..220MS.: REFRAC,PRE*<- OFF
169E E6            2517            SEX ADR
169F F8F6A606      2518            LDI A.3(OUTCTL);PLO ADR;LDN ADR
16A3 FAFA5655      2519            ANI #FA;STR ADR;OUT OUTSIG
16A7               2520  ..
16A7 01            2521  MS229:  SEP IPC
16A8 80F3E53AA7    2522            GLO RFT;XRI 229;BNZ MS229
16AD 01            2523  MS230:  SEP IPC
16AE E56326        2524            SEX ADR;OUT CLCHAS;DEC ADR ..CLEAR CHASI
1631               2525  ..
1631               2526  ..
1631               2527  ..TIME TO TURN OFF DIMSEN?
1631 01            2528  DIMSEN: SEP IPC
1632 F888A6E6      2529            LDI A.3(DIMTME);PLO ADR;SEX ADR
1635 83F33AB1      2530            GLO RFT;XOR;BNZ DIMSEN
16BA 6090F33AB1    2531            IRX;GHI RFT;XOR;BNZ DIMSEN
168F               2532  ..
168F               2533  ..
168F 01            2534  DIMOFF: SEP IPC
16C0 F8F6A656      2535            LDI A.0(OUTCTL);PLO ADR;SEX ADR
16C4 06FAF756      2536            LDN ADR;ANI #F7;STR ADR
16C8 65            2537            OUT OUTSIG
16C9               2538  ..
16C9               2539  ..
16C9 01            2540  MS400:  SEP IPC
16CA 80F3903AC9    2541            GLO RFT;XRI #90;BNZ MS400
16CF 90F3313AC9    2542            GHI RFT;XRI 1;BNZ MS400
16D4               2543  ..
16D4               2544  ..
16D4               2545  ..TURN OFF TOOBIG!
16D4 01            2546  MS401:  SEP IPC
16D5 F8F6A6E6      2547            LDI A.0(OUTCTL);PLO ADR;SEX ADR
16D9 06FAFD56      2548            LDN ADR;ANI #FD;STR ADR
16DD 653000        2549            OUT OUTSIG;BR MS36N
16E0               2550            END
```

In order to provide a full and complete description of system 10, the program for second micro-computer 44 of scanner system 24 is herein provided in Assembly Language on the following pages:

```
REPLST   CSDP     P ID=MEDICAL    13.34.56  THURSDAY 1 NOVEMBER 1979
         NATIONAL CSS, INC. (STAMFORD DATA CENTER)           EAST

FL LOC  COSMAC CODE    LNNO SOURCE LINE
       0000                  1 ..REPORT GENERATOR SYMBOLS & SUBROUTINES
       0000                  2 ..................................
       0000                  3 ..REGISTER ASSIGNMENTS:
       0000                  4 HOLD=0   ..(.1)=NEW RECORD#,(.0)=OLD
       0000                  5 IPC=1    ..INTERRUPT PROGRAM COUNTER
       0000                  6 STK=2    ..  "  STACK POINTER
       0000                  7 MPC=3    ..MAIN(BACKGROUND) P.C.
       0000                  8 CALL=4   ..SUBROUTINE(BACKGROUND) P.C.
       0000                  9 SRC=5    ..SOURCE ADDRESS POINTER
       0000                 10 DST=6    ..DESTINATION ADDRESS PNTR.
       0000                 11 SUM=7    ..GENERAL REGISTER
       0000                 12 TI=8     ..THERMAL INPUT INDEX
       0000                 13 TO=9     ..THERMAL OUTPUT INDEX
       0000                 14 STO=#0A  ..STORE INDEX
       0000                 15 RTR=#0B  ..RETRIEVE "
       0000                 16 CCT=#0C  ..CHARACTER COUNTER
       0000                 17 ADR=#0D  ..ADDRESS POINTER
       0000                 18 TPC=#0E  ..THERMAL PROGRAM COUNTER
       0000                 19 SPC=#0F  ..SYNCHRONIZE ROUTINE P.C.
       0000                 20 ..................................
       0000                 21 ..INPUT DEVICES:
       0000                 22 THMBSW=1 ..SHIFT THUMB SW BITS  0 EF4
       0000                 23 INPORT=4 ..INPUT PORT
```

```
0000        24 ..OUTPUT DEVICES:
0000        25 EKG1=1   ..EKG1 D/A CONVERTER
0000        26 EKG2=2   ..EKG2 D/A CONVERTER
0000        27 PRINTR=3 ..LOAD PRINTER BUFFER
0000        28 STRPCH=4 ..STRIP CHART(AND THERMAL PRINTER)
0000        29 CASOUT=5 ..CASSETTE CONTROL SIGNALS
0000        30 ..................................
0000        31 K1000=1000 ..ARITHMETIC CONSTANT
0000        32 HALT=#FF   ..PRINT BUFFER TERMINATOR
0000        33 ..ASCII CODES(PRINTER CONTROL) :
0000        34 US=#1F   ..20 COLUMNS
0000        35 RS=#1E   ..40  "
0000        36 GS=#1D   ..80  "
0000        37 SO=#0E   ..NO REVERSE FIELD
0000        38 BEL=#07  ..RING BELL
0000        39 LF=#0A   ..LINE FEED
0000        40 SP=#20   ..SPACE(BLANK)
0000        41 DOT=#2E  ..DOT(.)
0000        42 TD=#2E2E ..TWO DOTS  (..)
0000        43 ..TIMING CODES:
0000        44 THIRTS=120 ..THIRTY SECS.=4*30*(1/4)S.
0000        45 MS200=50
0000        46 HLFSEC=125
0000        47 ONESEC=250
0000        48 DATACT=74 ..74 BYTES DATA MODE
0000        49 EKGCT=#2F ..A.0(EKG DATA - DATACT)
0000        50 ..................................
0000        51 ..ADDRESSES:
0000        52 TAPBUF=#5800 ..TAPE BUFFER BEGINNING
0000        53 PERIOD=TAPBUF ..COUNTS 15MIN PERIODS
0000        54 MINUTE=PERIOD+1 ..COUNTS MINUTES(0-14)
0000        55 CODES1=MINUTE+1  ..1=CODE TRUE
0000        56 CODES2=CODES1+1
0000        57 CODES3=CODES2+1
0000        58 RUNCT=CODES3+1 ..BINARY VTACH COUNT
0000        59 DROPCT=RUNCT+2 ..DROPPED BEATS (BINARY)
0000        60 BEAT15=DROPCT+1  ..#BEATS IN 15 SECONDS(STACK)
0000        61 PVCMIN=BEAT15+15 ..1 MIN. PVC COUNTS(STACK)
0000        62 ARTSEC=PVCMIN+15 ..# ART 1/4 SECONDS IN MIN.
0000        63 SVEMIN=ARTSEC+15 ..1.MIN.SVEB COUNTS(STACK)
0000        64 SVTCT=SVEMIN+15 ..#SVT IN 15 MINUTES
0000        65 CPLCT=SVTCT+2 ..#COUPLETS/15MIN(16BITS)
0000        66 LLASCT=CPLCT+2 ..LOW LEV.ART.SEC.CTR.
0000        67 ENDATA=LLASCT+1 ..END OF DATA BUFFER
0000        68 ..
0000        69 EKGAL2=PERIOD ..EKG THERM.PRNTHD.ALRM.CDE.
0000        70 EKGAL1=EKGAL2+1 ..STUPID??????
0000        71 ..
0000        72 EKGDAT=TAPBUF+2 ..EKG DATA BEGINNING
0000        73 CASON=TAPBUF+257 ..CASSETTE ON
0000        74 EKGEND=TAPBUF+376 ..END EKG BUFFER
0000        75 ..
0000        76 STKTOP=#5BFF ..INTERRUPT STACK TOP
0000        77 CHR=STKTOP-4 ..HOLDS RECIEVED CHARACTER
0000        78 MODE=CHR-1 ..MODE READ FROM SYNC HEADER(TAPE)
0000        79 BKMODE=MODE-1 ..BACKGROUND'S MODE
0000        80 SCRBYT=BKMODE-1 ..SCRATCH BYTE
0000        81 ..
0000        82 CASCTL=#5B10  ..CASSETTE CONTROL BYTE
0000        83 INPWRD=CASCTL+1 ..INPUT PORT DUMPS HERE
0000        84 TIME=INPWRD+1 ..2 BYTES*4MS=TIME
0000        85 DIVISR=TIME+2
0000        86 QUOTNT=DIVISR+1
0000        87 REPCTL=QUOTNT+1 ..REPORT CONTROL(HEADING?)
0000        88 SCTL=REPCTL+1 ..STRIP CHART CONTROL
0000        89 PERDSP=SCTL+1  ..PERIOD DISPLACEMENT
0000        90 ..
0000        91 ..PRINT BUFFER IMAGE:
0000        92 PNTBUF=#5B20  ..PRINT BUFFER(LINE)
0000        93 HOURS=PNTBUF+1   ..TIME,HOURS(99)
0000        94 MINS=HOURS+3     ..TIME,MINUTES(99)
0000        95 SVECNT=PNTBUF+9  ..SVEB COUNT(9999)
0000        96 SVTCNT=PNTBUF+15 ..SVT COUNT(999)
0000        97 PVCNT=PNTBUF+22  ..VEB COUNT(9999)
0000        98 BGMCDE=PNTBUF+27 ..BIGEMINI CODE(B)
0000        99 VTCNT=PNTBUF+31  ..VT COUNT(999)
0000       100 CPLCNT=PNTBUF+36 ..COUPLETS COUNT(999)
```

```
        0000                    101  DBCNT=PNTBUF+42   ..DROPPED BEAT COUNT(999)
        0000                    102  STBCDE=PNTBUF+47  ..STABILITY CODE(U)
        0000                    103  ARTCDE=PNTBUF+49  ..ARTIFACTS CODE(X)
        0000                    104  SVERTE=PNTBUF+57  ..SVEB RATE(999)
        0000                    105  PVCRTE=PNTBUF+62  ..VEB RATE(999)
        0000                    106  HRTE=PNTBUF+58    ..HIGH RATE(999)
        0000                    107  LRTE=PNTBUF+73    ..LOW RATE(999)
        0000                    108  AVGRTE=PNTBUF+78  ..AVERAGE RATE(999)
        0000                    109  LFBUF=PNTBUF+81   ..HOLDS LINE FEED
        0000                    110  HLTBUF=LFBUF+1    ..HOLDS HALT
        0000                    111  ....................................
        0000                    112  ..CASSETTE CONTROL CODES:
        0000                    113  STOP=#01
        0000                    114  READ=#02
        0000                    115  FSTFWD=#00
        0000                    116  REW=#04
        0000                    117  WRITE=#0A
        0000                    118  ....................................
        0000                    119  ..TREND REPORTER BACKGROUND ROUTINE:
        0000  7100               120          DIS,0
F       0002  F800B3             121          LDI A.1(BGNRPT);PHI MPC
F       0005  F800A3D3           122          LDI A.0(BGNRPT);PLO MPC;SEP MPC
        0009  F85BB2B5           123  BGNRPT: LDI A.1(CHR);PHI STK;PHI SRC
        000D  B5BD               124          PHI DST;PHI ADR
        000F                     125  ..TEST.........DISABLE INTERRUPTS:...
        000F  E37133             126          SEX MPC;DIS,#33
        0012  F8FFA2A6E6         127          LDI A.0(STKTOP);PLO STK;PLO DST;SEX DST
        0017  F800737373737373   128          LDI 0;STXD;STXD;STXD;STXD;STXD
        001F  F813A6             129          LDI A.0(TIME+1);PLO DST
        0022  F8007373           130          LDI 0;STXD;STXD ..ZERO TIME
F       0026  F800BF             131          LDI A.1(SYNCTP);PHI SPC
F       0029  F800AF             132          LDI A.0(SYNCTP);PLO SPC
F       002C  F800B4             133          LDI A.1(DELAY);PHI CALL
F       002F  F800A4             134          LDI A.0(DELAY);PLO CALL
F       0032  F800B1             135          LDI A.1(INTRPT);PHI IPC
F       0035  F800A1             136          LDI A.0(INTRPT);PLO IPC
        0038  F8FFB0A0           137          LDI #FF;PHI HOLD;PLO HOLD
        003C  F816A6             138          LDI A.0(REPCTL);PLO DST
        003F  F80056             139          LDI 0;STR DST ..REPCTL<- 0
        0042                     140  ..CASSETTE<- STOP
        0042  F810A6             141          LDI A.0(CASCTL);PLO DST
        0045  F8015665           142          LDI STOP;STR DST;OUT CASOUT
        0049                     143  ..WAIT 1SEC. AFTER CASSETTE PRESENCE
        0049  F811A6             144  PRESWT: LDI A.0(INPWRD);PLO DST
        004C  6CFA013A49         145          INP INPORT;ANI #01;BNZ PRESWT
        0051  D400FA             146          SEP CALL,A(ONESEC)
        0054                     147  ..REWIND CASSETTE
        0054  F810A6             148          LDI A.0(CASCTL);PLO DST
        0057  F8045665           149          LDI REW;STR DST;OUT CASOUT
        005A                     150  ..ONE SECOND TO GET OFF CLEAR LEADER:
        005A  D400FA             151          SEP CALL,A(ONESEC)
        005E                     152  ..NO CASSETTE?
        005E  6CFA013A09         153  CLRLWT: INP INPORT;ANI #01;BNZ BGNRPT
        0063                     154  ..WAIT FOR CLEAR LEADER
        0063  6CFA02325E         155          INP INPORT;ANI #02;BZ CLRLWT
        0068                     156  ..CLEAR LEADER MUST REMAIN FOR 1/2 SEC.
        0068  D40070             157          SEP CALL,A(HLFSEC)
        006B  6CFA02326E         158          INP INPORT;ANI #02;BZ CLRLWT
        0070                     159  ..STOP CASSETTE:
        0070  F810A6E6           160          LDI A.0(CASCTL);PLO DST;SEX DST
        0074  F8015665           161          LDI STOP;STR DST;OUT CASOUT
F       0078  F800A4             162          LDI A.0(DELAY);PLO CALL
        007B  D40082             163          SEP CALL,A(MS200) ..WAIT .2 SEC.
        007E                     164  ..CLEAR MODE,BKMODE:
        007E  F8FAA5             165          LDI A.0(MODE);PLO SRC
        0081  F800552555         166          LDI 0;STR SRC;DEC SRC;STR SRC
        0086                     167  ....................................
        0086                     168  ..NEW BLOCK OF DATA  CASSETTE<-READ:
F       0086  F800A4D4           169  NEWBLK: LDI A.0(TCASON);PLO CALL;SEP CALL
        008A                     170  ..
        008A                     171  ..LOOP TO WAIT FOR DATA(EKG):
F       008A  F800A4D4           172  DATAWT: LDI A.0(LTCMOD);PLO CALL;SEP CALL
        008E                     173  ..CASCTL=STOP? (DATA RECIEVED YET?)
        008E  F810A6             174  CKSTOP: LDI A.0(CASCTL);PLO DST
F       0091  06F801CA0000       175          LDN DST;XRI STOP;LBNZ CKWAIT
        0097                     176  ..STOPPED! PRINT HEADER IF NOT YET PRINTED
        0097  F816A6             177  PRNTHD: LDI A.0(REPCTL);PLO DST
```

```
F  009A  06FA01CA0000      178           LDN DST;ANI #01;LBNZ CKRECN
F  00A0  F800A6            179           LDI A.0(MEDMSG);PLO DST
F  00A3  F800B6E6          180           LDI A.1(MEDMSG);PHI DST;SEX DST
F  00A7  F800A4            181  DOHEAD:  LDI A.0(PRNTQT);PLO CALL
F  00AA  D4C00000          182           SEP CALL;LBR DELYLF
   00AE  F816A6            183           LDI A.0(REPCTL);PLO DST
   00B1  FA5BB6            184           LDI A.1(REPCTL);PHI DST
   00B4  F80156            185           LDI 1;STR DST
F  00B7  3000              186           BR TTMBSW
   00B9                    187  ..DELAY IF LINE FEED:
   00B9  2646              188  DELYLF:  DEC DST;LDA DST
   00BB  FB0ACA00A7        189           XRI LF;LBNZ DOHEAD
   00C0  F830A7B7          190           LDI #30;PLO SUM;PHI SUM
   00C4  27973AC4          191           DEC SJM;GHI SUM;BNZ *-2
   00C8  C000A7            192           LBR DOHEAD
   00CB                    193  ..
   00CB                    194  ..TRANSFER THUMBWHEEL SWITCH SETTING
   00CB                    195  ..TO SJM:
   00CB  E56307            196  TTMBSW:  SEX M;OUT PRINTR,BEL ..LOAD LATCHES
   00CE  F818A6E6          197           LDI A.0(PERDSP);PLO DST;SEX DST
   00D2  F800B7A7          198           LDI 0;PHI SUM;PLO SUM
   00D6                    199  ..SUM.0 <-MINUTES
   00D6  F807A538          200           LDI 7;PLO SRC;SKP
   00DA  69                201  GETMSW:  INP THMBSW ..NEXT BIT
   00DB  87F637E1F940      202           GLO SJM;SHR;B4 *+4;ORI #40
   00E1  A725853A0A        203           PLO SUM;DEC SRC;GLO SRC;BNZ GETMSW
   00E5                    204  ..SUM.1 <- HOURS
   00E6  F806A5            205           LDI 6;PLO SRC
   00E9  69                206  GETHSW:  INP THMBSW ..NEXT BIT
   00EA  97F637F0F920      207           GHI SUM;SHR;B4 *+4;ORI #20
   00F0  B725853AF9        208           PHI SJM;DEC SRC;GLO SRC;BNZ GETHSW
   00F5                    209  ..
   00F5                    210  ..CONVERT THUMBWHEEL SETTING TO PERIOD
   00F5                    211  ..DISPLACEMENT
   00F5  F80056            212           LDI 0;STR DST
F  00F8  87C20000          213           GLO SUM;LBZ THMHRS ..MIN=0?
   00FC  F80456            214           LDI 4;STR DST
F  00FF  87FF46C30000      215           GLO SUM;SMI #46;LBDF THMHRS ..>45?
   0105  F80356            216           LDI 3;STR DST
F  0108  87FF313300        217           GLO SUM;SMI #31;BPZ THMHRS ..>30?
   010D  F80256            218           LDI 2;STR DST
F  0110  87FF163300        219           GLO SUM;SMI #16;BPZ THMHRS ..>15?
   0115  F80156            220           LDI 1;STR DST ..0 > X >15 !
   0118                    221  ..ADD HOURS DISPLACEMENT:
   0118                    222  ..FORCE HOURS .LE.23
F  0118  97FF233B00        223  THMHRS:  GHI SUM;SMI #23;BM CVHRPD
   011D  F823B7            224           LDI #23;PHI SUM ..HRS<-23
   0120  97FA0FFEFE        225  CVHRPD:  GHI SUM;ANI #0F;SHL;SHL
   0125  E6F456            226           SEX DST;ADD;STR DST ..LEAST SIG DIGITS
F  0129  97FA303200        227           GHI SUM;ANI #30;BZ CKRECN
   012D  06FC2856          228           LDN DST;ADI 40;STR DST
F  0131  97FA203200        229           GHI SJM;ANI #20;BZ CKRECN
   0135  06FC2856          230           LDN DST;ADI 40;STR DST
   013A                    231  ..
   013A                    232  ..
   013A                    233  ..STOPPED!! OLD RECORD# = NEW-1?
   013A  F8FBA6            234  CKRECN:  LDI A.0(SCRBYT);PLO DST
   013D  90FF0156E6        235           GHI HOLD;SMI 1;STR DST;SEX DST
F  0142  80F73200          236           GLO HOLD;SM;BZ WHMODE
   0146                    237  ..PRINT RECORD OUT OF SEQUENC MSG.:
F  0146  F800A6            238           LDI A.0(EOSMSG);PLO DST
F  0149  F800B6            239           LDI A.1(EOSMSG);PHI DST
F  014C  E6F800A4          240  EOSLOP:  SEX DST;LDI A.0(PRNTQT);PLO CALL
   0150  D4C0014C          241           SEP CALL;LBR EOSLOP
   0154  90A0              242           GHI HOLD;PLO HOLD ..NEW->OLD
   0156  F85BB6            243           LDI A.1(BKMODE);PHI DST
   0159                    244  ..WHICH MODE? :
   0159  F8F9A6            245  WHMODE:  LDI A.0(BKMODE);PLO DST
F  015C  06FB01C20000      246           LDN DST;XRI #01;LBZ DATAMD
F  0162  06FB41C20000      247           LDN DST;XRI #41;LBZ SWLDAT
F  0168  06FB84C20000      248           LDN DST;XRI #84;LBZ EKGMDE
F  016E  06FB92C20000      249           LDN DST;XRI #92;LBZ EKGMDE
   0174  C00086            250           LBR NEWBLK ..ILLEGAL,SKIP RECORD!
   0177                    251  ..
   0177                    252  ..WAITED TOO LONG?
F  0177  F800A4D4          253  CKWAIT:  LDI A.0(TIMER);PLO CALL;SEP CALL
   017B  F813A6            254           LDI A.0(TIME+1);PLO DST
```

```
017E  05F320CA008A      255            LDN DST;XRI #20;LBNZ DATAWT
0184                    256   ..YES,ERROR OR END OF REPORT? :
0184  E37163            257            SEX MPC;DIS ,#53
0187  F816A5            258            LDI A.0(REPCTL);PLO SRC
F 018A  05CA0000        259            LDN SRC;LBNZ ENDRPT
018E                    260   ..PRINT ERROR,NO DATA THIS SIDE OF...
F 018E  F800B6          261            LDI A.1(ERRMSG);PHI DST
F 0191  F800A6          262            LDI A.0(ERRMSG);PLO DST
F 0194  E6F800A4        263   PRINTL: SEX DST;LDI A.0(PRNTQT);PLO CALL
  0198  D4C00194        264            SEP CALL;LBR PRINTL
  019C                  265   ..STOP CASSETTE:
  019C  F810A6E6        266            LDI A.0(CASCTL);PLO DST;SEX DST
  01A0  F85BB6          267            LDI A.1(CASCTL);PHI DST
  01A3  F8015665        268            LDI STOP;STR DST;OUT CASOUT
  01A7                  269   ..WAIT FOR NO CASSETTE:
  01A7  F811A6E6        270   NOCAWT: LDI A.0(INPWRD);PLO DST;SEX DST
  01AB  6CFA01CA0009    271            INP INPORT;ANI #01;LBNZ BGNRPT
  01B1  30A7            272            BR  NOCAWT
  01B3                  273   ..............................
  01B3                  274   ..PRINT:  ******END OF REPORT******
F 01B3  F800B6          275   ENDRPT: LDI A.1(EOTMSG);PHI DST
F 01B6  F800A6          276            LDI A.0(EOTMSG);PLO DST
  01B9  3094            277            BR PRINTL
  01BB                  278   ..
  01BB                  279   ..PRINT:  PLEASE CHECK CASSETTE.
F 01BB  F800A6          280   NOCASS: LDI A.0(NCMSG);PLO DST
F 01BE  F800B6          281            LDI A.1(NCMSG);PHI DST
  01C1  3094            282            BR PRINTL
  01C3                  283   ..............................
  01C3                  284   ..EKG MODE:
  01C3                  285   ..CONVERT TIME TO ASCII STRING FOR
  01C3                  286   ..THERMAL PRINTHEAD OUTPUT:
F 01C3  F800BB          287   EKGMDE: LDI A.1(THRMSK);PHI RTR
F 01C6  F800AB          288            LDI A.0(THRMSK);PLO RTR
  01C9  F85BB6          289            LDI A.1(PNTBUF+1);PHI DST
  01CC  F821A6          290            LDI A.0(PNTBUF+1);PLO DST
  01CF  4B56            291            LDA RTR;STR DST
  01D1  FBFF163ACF      292            XRI HALT;INC DST;BNZ *-5
  01D5                  293   ..TRANSLATE HOURS TO PRINT MASK
  01D5  F85BBB          294            LDI A.1(PERIOD);PHI RTR
  01D9  F800AB          295            LDI A.0(PERIOD);PLO RTR
  01DC  F818A5E5        296            LDI A.0(PERDSP);PLO SRC;SEX SRC
  01E0  0BF45B          297            LDN RTR;ADD;STR RTR ..ADD DISPLACEMENT
  01E3                  298   ..PERIOD WRAPS AROUND AT 24:00 HOURS :
F 01E3  FF603B00        299   MXEK24: SMI 96;BM EKPD24
  01E7  5B30E3          300            STR RTR;BR MXEK24
  01EA  F800B7          301   EKPD24: LDI 0;PHI SUM
  01ED  4BF6F6A7        302            LDA RTR;SHR;SHR;PLO SUM
  01F1  F821A6          303            LDI A.0(HOURS);PLO DST
  01F4  F800B4          304            LDI A.1(TENSL);PHI CALL
F 01F7  F800A4D4        305            LDI A.0(TENSL);PLO CALL;SEP CALL
  01FB                  306   ..ADD PERIOD DISPLACEMENT TO MINUTES:
  01FB  0BA72B          307            LDN RTR;PLO SUM;DEC RTR
  01FE  F800B7          308            LDI 0;PHI SUM
  0201  0BFA01320A      309            LDN RTR;ANI #01;BZ *+6 ..ADD 5MIN?
  0206  87FC0FA7        310            GLO SUM;ADI 15;PLO SUM
  020A                  311   ..ADD 10 MIN.?
  020A  0BFA023213      312            LDN RTR;ANI #02;BZ *+6
  020F  87FC1EA7        313            GLO SUM;ADI 30;PLO SUM
  0213                  314   ..TRANSLATE MINUTES TO PRINT MASK:
  0213  F824A6          315            LDI A.0(MINS);PLO DST
F 0216  F800A4D4        316            LDI A.0(TENSL);PLO CALL;SEP CALL
  021A  F821A8          317            LDI A.0(PNTBUF+1);PLO TI
  021D  F85BB8          318            LDI A.1(PNTBUF+1);PHI TI
F 0220  F800AE          319            LDI A.0(STHOUT);PLO TPC
F 0223  F800BE          320            LDI A.1(STHOUT);PHI TPC
  0226                  321   ..
  0226                  322   ..S.C. <-ON;WAIT 200MS.
  0226  E361FF          323   SCONOW: SEX MPC;OUT EKG1,#FF ..SWING PEN
  0229  6401            324            OUT STRPCH,#01 ..MOTOR<- ON
  022B  F813A6E6        325            LDI A.0(TIME+1);PLO DST;SEX DST
  022F  F8007373        326            LDI 0;STXD;STXD
F 0233  F800A4D4        327   SCONWT: LDI A.0(TIMER);PLO CALL;SEP CALL
  0237  F813A6          328            LDI A.0(TIME+1);PLO DST
  023A  063233          329            LDN DST;BZ SCONWT
  023D  F8F9A5          330            LDI A.0(BKMODE);PLO SRC ..CONTINUE?
F 0240  05FB923200      331            LDN SRC;XRI #92;BZ DOCONT
```

```
        0245                    332 ..OUTPUT DATA:
        0245  F802AB            333 EKGOUT: LDI A.0(EKGDAT);PLO RTR
        0248  F858BB            334         LDI A.1(EKGDAT);PHI RTR
        024B  80FC01A0          335         GLO HOLD;ADI 1;PLO HOLD ..OLD+1->RECD#
        024F                    336 ..EVERY 8MS. :       (25MM/SEC)
        024F  354F              337 EKGWT1: B2 EKGWT1
        0251  DE                338         SEP TPC ..THERMAL PRNTHD P.C.
        0252  3D52              339 EKGWT2: BN2 EKGWT2
        0254  3554              340 EKGWT3: B2 EKGWT3
        0256  DE                341         SEP TPC ..THERMAL PRNTHD P.C.
        0257  3D57              342 EKGWT4: BN2 EKGWT4
        0259  EB61              343         SEX RTR;OUT EKG1
        025B                    344 ..AT RTR=A(CASON),TURN CASSETTE ON:
F       025B  9BFB593A00        345         GHI RTR;XRI A.1(CASON);BNZ CKEKMD
F       0260  8BFB013A00        346         GLO RTR;XRI A.0(CASON);BNZ CKEKMD
F.      0265  F800A4D4          347         LDI A.0(TCASON);PLO CALL;SEP CALL
        0269                    348 ..DATA RECIEVED YET? (LATCH MODE)
F       0269  F800A4D4          349 CKEKMD: LDI A.0(LTCMOD);PLO CALL;SEP CALL
        026D                    350 ..DONE OUTPUTTING YET?
        026D  8BFB793A4F        351 CKEKDN: GLO RTR;XRI A.0(EKGEND+1);BNZ EKGWT1
        0272  9BFB593A4F        352         GHI RTR;XRI A.1(EKGEND+1);BNZ EKGWT1
        0277                    353 ..YES,IS NEXT RECORD A CONTINUATION? :
        0277  F8F9A5            354         LDI A.0(BKMODE);PLO SRC
F       027A  05FB923A00        355         LDN SRC;XRI #92;BNZ STOPSC
F       027F  F800AE            356 DOCONT: LDI A.0(STHALM);PLO TPC
F       0282  F800BE3045        357         LDI A.1(STHALM);PHI TPC;BR EKGOUT
        0287                    358 ..NO,STOP S.C.,DAC<- 00
        0287  E36100            359 STOPSC: SEX MPC;OUT EKG1,#00 ..SWING PEN
        028A  6400              360         OUT STRPCH,#00 ..MOTOR<-OFF
        028C  C0008A            361         LBR DATAWT
        028F                    362 ............................
        028F                    363 ..SWITCH LEAD MESSAGE:
F       028F  F800B6            364 SWLDAT: LDI A.1(SWLMSG);PHI DST
F       0292  F800A6            365         LDI A.0(SWLMSG);PLO DST
F       0295  E6F800A4          366 SWLOOP: SEX DST;LDI A.0(PRNTQT);PLO CALL
        0299  D4C00295          367         SEP CALL;LBR SWLOOP
        029D  F85BB6            368         LDI A.1(PNTBUF);PHI DST
        02A0                    369 ..DRAW A LINE BEFORE EVERY EIGTH LINE
        02A0  F800AB            370 DATAMD: LDI A.0(PERIOD);PLO RTR
        02A3  F858BB            371         LDI A.1(PERIOD);PHI RTR
        02A6  F818A5E5          372         LDI A.0(PERDSP);PLO SRC;SEX SRC
        02AA  0BF45B            373         LDN RTR;ADD;STR RTR
        02AD                    374 ..PERIOD WRAPS AROUND AT 24:00 HOURS
F       02AD  FF603B00          375 MXDT24: SMI 96;BM DTPD24
        02B1  5B30AD            376         STR RTR;BR MXDT24
F       02B4  FA07CA0000        377 DTPD24: ANI #07;LBNZ DODATA
        02B9  F820A6            378         LDI A.0(PNTBUF);PLO DST
        02BC  F81D5616          379         LDI GS;STR DST;INC DST
        02C0  F82D56            380         LDI '-';STR DST
        02C3  4656              381         LDA DST;STR DST
        02C5  86F3713AC3        382         GLO DST;XRI A.0(LFBUF);BNZ *-5
        02CA  F80A5616          383         LDI LF;STR DST;INC DST
        02CE  F8FF56            384         LDI HALT;STR DST
        02D1                    385 ..PRINT LINE FROM PRINT BUFFER
        02D1  F820A6E6          386         LDI A.0(PNTBUF);PLO DST;SEX DST
F       02D5  F800B4            387         LDI A.1(PRNTQT);PHI CALL
F       02D8  F800A4            388 PRINTB: LDI A.0(PRNTQT);PLO CALL
        02DB  04C002D8          389         SEP CALL;LBR PRINTB
        02DF                    390 ..DELAY WHILE CARRIAGE RETURNS:
        02DF  F8304787          391         LDI #30;PLO SUM;PHI SUM
        02E3  27973AE3          392         DEC SUM;GHI SUM;BNZ *-2
F       02E7  C00000            393         LBR DODATA
        02EA                    394 ............................
        02EA                    395 ..MOVE PRINT MASK TO PRINT BUFFER:
        02EA  80FC01A0          396 DODATA: GLO HOLD;ADI 1;PLO HOLD ..OLD+1->RECD#
F       02EE  F800BB            397         LDI A.1(PNTMSK);PHI RTR
F       02F1  F800AB            398         LDI A.0(PNTMSK);PLO RTR
        02F4  F85BB6            399         LDI A.1(PNTBUF);PHI DST
        02F7  F820A6            400         LDI A.0(PNTBUF);PLO DST
        02FA  4B56              401         LDA RTR;STR DST
D       02FC  FBFF163AFA        402         XRI HALT;INC DST;BNZ *-5
        0301                    403 ..TRANSLATE TIME TO PRINT BUFFER:
        0301  F858BB            404         LDI A.1(PERIOD);PHI RTR
        0304  F800AB            405         LDI A.0(PERIOD);PLO RTR
        0307  F85BB6            406         LDI A.1(MINS+1);PHI DST
        030A  F825A6            407         LDI A.0(MINS+1);PLO DST
F       030D  0BFA013200        408         LDN RTR;ANI #01;BZ TENMIN
        0312  06FC0556          409         LDN DST;ADI 5;STR DST
```

```
F   0315  260BFA033200       410 TENMIN: DEC DST;LDN RTR;ANI #03;BZ DOHOUR
F   031C  F8013A00           411         XRI #01;BNZ ADTWMN ..ADD 20MIN
    0320  F83156             412         LDI T"1";STR DST ..TEN MIN<- 1
    0323                     413 ..HOURS(BIN-->ASCII) FIRST SHR 2
    0323  F800B7             414 DOHOUR: LDI 0;PHI SUM
    0326  0BF6F6A7           415         LDN RTR;SHR;SHR;PLO SUM
    032A  F821A6             416         LDI A.0(HOURS);PLO DST
F   032D  F800B4             417         LDI A.1(TENSL);PHI CALL
F   0330  F800A404           418         LDI A.0(TENSL);PLO CALL;SEP CALL
F   0334  C00000             419         LBR DOCODE
    0337                     420 ..
    0337  E60BFA03           421 ADTWMN: SEX DST;LDN RTR;ANI #03
    033B  FC3156C00323       422         ADI T"1";STR DST;LBR DOHOUR
    0341                     423 ..
    0341                     424 ..TRANSLATE CODES TO PRINT BUFFER
    0341  F803AB             425 DOCODE: LDI A.0(CODES2);PLO RTR
    0344  F83BA6             426         LDI A.0(BGMCDE);PLO DST
    0347  0BFA10324F         427         LDN RTR;ANI #10;BZ *+5
    034C  F84256             428         LDI T"B";STR DST ..BGMCDE<- B
    034F  F84FA6             429         LDI A.0(STBCDE);PLO DST
    0352  0BFA20325A         430         LDN RTR;ANI #20;BZ *+5
    0357  F85556             431         LDI T"U";STR DST ..STBCDE<- U
    035A                     432 ..CONVERT BINARY SVT COUNT TO PRINT BUFFER
    035A  F844AB             433         LDI A.0(SVTCT);PLO RTR
    035D  4BA70BB7           434         LDA RTR;PLO SUM;LDN RTR;PHI SUM
    0361  F82FA6             435         LDI A.0(SVTCNT);PLO DST
F   0364  F800A404           436         LDI A.0(HUNDRL);PLO CALL;SEP CALL
    0368                     437 ..CONVERT BINARY RUNS COUNT TO PRINT BUFFER
    0368  F805AB             438         LDI A.0(RUNCT);PLO RTR
    036B  4BA70BB7           439         LDA RTR;PLO SUM;LDN RTR;PHI SUM
    036F  F83FA6             440         LDI A.0(VTCNT);PLO DST
F   0372  F800A404           441         LDI A.0(HUNDRL);PLO CALL;SEP CALL
    0376                     442 ..CONVERT BINARY CPL COUNT TO PRINT BUFFER
    0376  F846AB             443         LDI A.0(CPLCT);PLO RTR
    0379  4BA70BB7           444         LDA RTR;PLO SUM;LDN RTR;PHI SUM
    037D  F844A6             445         LDI A.0(CPLCNT);PLO DST
F   0380  F800A404           446         LDI A.0(HUNDRL);PLO CALL;SEP CALL
    0384                     447 ..CONVERT BINARY DROPPED BEAT COUNT
    0384                     448 ..TO PRINT BUFFER
    0384  F807AB             449         LDI A.0(DROPCT);PLO RTR
    0387  0BA7F800B7         450         LDN RTR;PLO SUM;LDI 0;PHI SUM
    038C  F84AA6             451         LDI A.0(DBCNT);PLO DST
F   038F  F800A404           452         LDI A.0(TENSL);PLO CALL;SEP CALL
    0393                     453 ..........................................
    0393                     454 .. .375*L.L.ART.SEC.->SUM
    0393                     455 .. .75/2 = .375:
    0393  F849AB             456         LDI A.0(LLASCT);PLO RTR
    0396  4BF6A7             457         LDA RTR;SHR;PLO SUM
    0399  0B76B7             458         LDN RTR;SHRC;PHI SUM
    039C                     459 ..TOTAL ARTSEC-->SUM
    039C  F825ABEB           460         LDI A.0(ARTSEC);PLO RTR;SEX RTR
    03A0  87F4A7             461 ARTSLP: GLO SUM;ADD;PLO SUM
    03A3  977C00B7           462         GHI SUM;ADCI 0;PHI SUM
    03A7  1BBBF835           463         INC RTR;GLO RTR;XRI A.0(ARTSEC+15)
    03AB  3AA0               464         BNZ ARTSLP ..CONTINUE
    03AD                     465 ..CLASSIFY ARTIFACTS AS NONE,LOW,MEDIUM
    03AD                     466 ..OR HIGH
    03AD  F85146             467         LDI A.0(ARTCDE);PLO DST
F   03B0  973A00             468         GHI SUM;BNZ CKHLAS
F   03B3  873A00             469         GLO SUM;BNZ CKHLAS
F   03B6  F82056C00000       470         LDI SP;STR DST;LBR DONEAS
    03BC                     471 ..
    03BC  97FF08CB03C7       472 CKHLAS: GHI SUM;SMI 8;LBNF *+8
F   03C2  F848563000         473         LDI T"H";STR DST;BR DONEAS
    03C7  97FF03CB03D2       474         GHI SUM;SMI 3;LBNF *+8
F   03CD  F84D563000         475         LDI T"M";STR DST;BR DONEAS
    03D2  F84C56             476         LDI T"L";STR DST
    03D5  C4                 477 DONEAS: NOP
    03D6                     478 ..........................................
    03D6                     479 ..TOTAL SVE COUNT -->SUM
    03D6  F835ABEB           480         LDI A.0(SVEMIN);PLO RTR;SEX RTR
    03DA  F800A7B7           481         LDI 0;PLO SUM;PHI SUM
    03DE  87F4A71B           482 SUMSVE: GLO SUM;ADD;PLO SUM;INC RTR
    03E2  977C00B7           483         GHI SUM;ADCI 0;PHI SUM
    03E6  8BFB443ADE         484         GLO RTR;XRI A.0(SVEMIN+15);BNZ SUMSVE
    03EB                     485 ..CONVERT BINARY SVE COUNT TO PRINT BUFFER
    03EB  D429               486         SEP CALL,A.0(SVECNT)
```

```
03ED              487  ..............................
03ED              488  ..FIND LARGEST #SVE/MIN
03ED F8004787     489         LDI 0;PLO SUM;PHI SUM
03F1 F835ABEB     490         LDI A.0(SVEMIN);PLO RTR;SEX RTR
03F5 87F7CF       491  SVELP: GLO SUM;SM;LSDF
03F8 0BA7         492         LDN RTR;PLO SUM
03FA 1B8BFB44     493         INC RTR;GLO RTR;XRI A.0(SVEMIN+15)
03FE 3AF5         494         BNZ SVELP ..CONTINUE?
0400              495  ..CONVERT BINARY SVE RATE TO PRINT BUFFER
0400 F859A6       496         LDI A.0(SVERTE);PLO DST
F  0403 F800A4D4  497         LDI A.0(HUNDRL);PLO CALL;SEP CALL
0407              498  ..............................
0407              499  ..TOTAL PVC COUNT -->SUM
0407 F817ABEB     500         LDI A.0(PVCMIN);PLO RTR;SEX RTR
040B F8004787     501         LDI 0;PLO SUM;PHI SUM
040F 87F4A71B     502  SUMPVC: GLO SUM;ADD;PLO SUM;INC RTR
0413 977C0087     503         GHI SUM;ADCI 0;PHI SUM
0417 83F3263A0F   504         GLO RTR;XRI A.0(PVCMIN+15);BNZ SUMPVC
041C              505  ..CONVERT BINARY PVC COUNT TO PRINT BUFFER
041C D436         506         SEP CALL,A.0(PVCNT)
041E              507  ..............................
041E              508  ..FIND LARGEST #PVC/MIN
041E F8004787     509         LDI 0;PLO SUM;PHI SUM
0422 F817ABEB     510         LDI A.0(PVCMIN);PLO RTR;SEX RTR
0426 87F7CF       511  PVCLP: GLO SUM;SM;LSDF
0429 0BA7         512         LDN RTR;PLO SUM
042B 1B8BFB26     513         INC RTR;GLO RTR;XRI A.0(PVCMIN+15)
042F 3A26         514         BNZ PVCLP ..CONTINUE?
0431              515  ..CONVERT BINARY PVC RATE TO PRINT BUFFER
0431 F85EA6       516         LDI A.0(PVCRTE);PLO DST
F  0434 F800A4D4  517         LDI A.0(HUNDRL);PLO CALL;SEP CALL
0438              518  ..............................
0438              519  ..PROCESS 15 SECOND BEAT COUNTS:
0438              520  ..INVALIDATE COUNTS IF .GT. 40 S. ARTIFACTS
0438 F826AB       521         LDI A.0(ARTSEC);PLO RTR
F  043B 4BFF783300 522  VALIDB: LDA RTR;SMI THIRTS;BPZ INVLBT
0440 88F3353A3B   523  VALIDC: GLO RTR;XRI A.0(ARTSEC+15);BNZ VALIDB
F  0445 3000      524         BR DOHR
0447              525  ..
0447              526  ..ARTSEC TO BEAT15 STACK DISPLACEMENT=30
0447 8BFF1EAB     527  INVLBT: GLO RTR;SMI 30;PLO RTR
044B F8005B       528         LDI 0;STR RTR ..INVALIDATE!
044E 8BFC1EAB     529         GLO RTR;ADI 30;PLO RTR
0452 3040         530         BR VALIDC ..CONTINUE VALIDATION
0454              531  ..
0454              532  ..SUM<- HIGHEST RATE
0454 F8004787     533  DOHR: LDI 0;PLO SUM;PHI SUM
0458 F808ABEB     534         LDI A.0(BEAT15);PLO RTR;SEX RTR
045C 87F7CF       535  HRLOOP: GLO SUM;SM;LSDF ..REPLACE H.R.?
045F 0BA7         536         LDN RTR;PLO SUM ..REPLACE H.R.!
0461 1B8BFB17     537         INC RTR;GLO RTR;XRI A.0(BEAT15+15)
0465 3A5C         538         BNZ HRLOOP ..CONTINUE?
0467              539  ..15 SEC. RATE *4 = 60 SEC. RATE
0467 87FEA7       540         GLO SUM;SHL;PLO SUM
046A 977EB7       541         GHI SUM;SHLC;PHI SUM
046D 87FEA7       542         GLO SUM;SHL;PLO SUM
0470 977EB7       543         GHI SUM;SHLC;PHI SUM
0473              544  ..CONVERT BINARY HIGH RATE TO PRINT BUFFER
0473 F864A6       545         LDI A.0(HRTE);PLO DST
F  0476 F800A4D4  546         LDI A.0(HUNDRL);PLO CALL;SEP CALL
047A              547  ..SUM<- LOWEST NONZERO RATE
047A F800B7A7     548         LDI 0;PHI SUM;PLO SUM
047E F808ABEB     549         LDI A.0(BEAT15);PLO RTR;SEX RTR
F  0482 0B3200    550  LRLOOP: LDN RTR;BZ SKLRPL ..SKIP LR REPLACE
0485 87CEF7C7     551         GLO SUM;LSZ;SM;LSNF ..REPLACE LR?
0489 0BA7         552         LDN RTR;PLO SUM ..REPLACE LR!
048B 1B8BFB17     553  SKLRPL: INC RTR;GLO RTR;XRI A.0(BEAT15+15)
048F 3A82         554         BNZ LRLOOP ..CONTINUE?
0491              555  ..15 SEC. LOW RATE *4 = 60 SEC. LR
0491 87FEA7       556         GLO SUM;SHL;PLO SUM
0494 977EB7       557         GHI SUM;SHLC;PHI SUM
0497 87FEA7       558         GLO SUM;SHL;PLO SUM
049A 977EB7       559         GHI SUM;SHLC;PHI SUM
049D              560  ..CONVERT BINARY LR TO PRINT BUFFER
049D F869A6       561         LDI A.0(LRTE);PLO DST
F  04A0 F800A4D4  562         LDI A.0(HUNDRL);PLO CALL;SEP CALL
04A4              563  ..............................
```

```
           04A4                    564   ..COMPUTE AVERAGE RATE:
           04A4                    565   ..# VALID BEATS/15SEC. -->DIVISR
           04A4                    566   ..SUM<-- TOTAL # BEATS
           04A4  F808ABEB          567         LDI A.0(BEAT15);PLO RTR;SEX RTR
           04A8  F814A5            568         LDI A.0(DIVISR);PLO SRC
           04AB  F85BB5            569         LDI A.1(DIVISR);PHI SRC
           04AE  F800B7A755        570         LDI 0;PHI SUM;PLO SUM;STR SRC
        F  04B3  083200            571 AVGLP: LDN RTR;BZ ADDAVG
           04B6  05FC0155          572         LDN SRC;ADI 1;STR SRC ..INC VAL.
           04BA  87F4A7            573 ADDAVG: GLO SUM;ADD;PLO SUM
           04BD  977C00B7          574         GHI SUM;ADCI 0;PHI SUM
           04C1  1BB8FB17          575         INC RTR;GLO RTR;XRI A.0(BEAT15+15)
           04C5  3AB3              576         BNZ AVGLP ..CONTINUE?
        F  04C7  05C20000          577         LDN SRC;LBZ ARTEMV ..DIVISR=0 ?
           04CB                    578   ..DIVIDE TOTAL BY # VALID ENTRIES
        F  04CB  F800A4            579         LDI A.0(DIVIDE);PLO CALL
           04CE  D41415            580         SEP CALL,A.0(DIVISR),A.0(QUOTNT)
           04D1                    581   ..(BEATS/15SEC)*4 = BEATS/MIN
           04D1                    582   ..ON RETURN DST=A(QUOTNT)
           04D1  05FEA7            583         LDN DST;SHL;PLO SUM
           04D4  F8007EB7          584         LDI 0;SHLC;PHI SUM
           04D8  87FEA7            585         GLO SUM;SHL;PLO SUM
           04DB  977EB7            586         GHI SUM;SHLC;PHI SUM
           04DE  87FC02A7          587         GLO SUM;ADI 2;PLO SUM ..0-4->-+2
           04E2  977C00B7          588         GHI SUM;ADCI 0;PHI SUM
           04E6                    589   ..TRANSLATE BINARY AVERAGE RATE ->PRINT BUFFER
           04E6  F86EA6            590         LDI A.0(AVGRTE);PLO DST
        F  04E9  F800A4D4          591         LDI A.0(HUNDRL);PLO CALL;SEP CALL
           04ED                    592   ...............................
           04ED                    593   ..BLANK LEADING ZEROES IN PRINT BUFFER
           04ED  F828A6            594 BLKZER: LDI A.0(SVECNT-1);PLO DST
           04F0                    595   ..LOOP HERE UNTIL NON NUMERIC
        F  04F0  05F8FFC20000      596 CKDIG: LDN DST;XRI HALT;LBZ DONEBO
        F  04F6  46FF30CB0000      597         LDA DST;SMI T'0';LBNF CK0
           04FC  2646FF3ACB04F0    598         DEC DST;LDA DST;SMI #3A;LBNF CKDIG
           0503  C4C4C4            599         NOP;NOP;NOP
           0506                    600   ..LAST CHR WAS NON NUMERIC,CHEK FOR 0
        F  0506  05F8FF3200        601 CK0:    LDN DST;XRI HALT;BZ DONEBO
           050B  05F830CA04F0      602         LDN DST;XRI T'0';LBNZ CKDIG
           0511                    603   ..IS THE 0 FOLLOWED BY A NUMERIC?
           0511  1505FF30CB04F0    604 CKODG: INC DST;LDN DST;SMI T'0';LBNF CKDIG
           0518  06FF3AC304F0      605         LDN DST;SMI #3A;LBDF CKDIG
           051E  26F82056          606 BLANKO: DEC DST;LDI SP;STR DST
           0522  153006            607         INC DST;BR CK0
           0525                    608   ..
           0525                    609 DONEBO=*
           0525                    610   ..PRINT LINE FROM PRINT BUFFER
           0525  F820A6E6          611         LDI A.0(PNTBUF);PLO DST;SEX DST
        F  0529  F800B4            612         LDI A.1(PRNTQT);PHI CALL
        F  052C  F800A4            613 PRINTC: LDI A.0(PRNTQT);PLO CALL
           052F  D4C0052C          614         SEP CALL;LBR PRINTC
           0533                    615   ..DONE,GET NEXT BLOCK:
           0533  C00086            616         LBR NEWBLK
           0536                    617   ..MOVE T'---' TO RATE COLUMNS(DIVISR=0)
           0536  F86EA6            618 ARTEMV: LDI A.0(AVGRTE);PLO DST
           0539  F82D5616          619         LDI T'-';STR DST;INC DST
           053D  561656            620         STR DST;INC DST;STR DST
           0540  F869A6            621         LDI A.0(LRTE);PLO DST
           0543  F82D5616          622         LDI T'-';STR DST;INC DST
           0547  561656            623         STR DST;INC DST;STR DST
           054A  F864A6            624         LDI A.0(HRTE);PLO DST
           054D  F82D5616          625         LDI T'-';STR DST;INC DST
           0551  561656            626         STR DST;INC DST;STR DST
           0554  C004ED            627         LBR BLKZER
           0557                    628   ..------------------------..
           0557                    629   ..STRIP CHART THERMAL PRINTHEAD ALARM IND.
        F  0557  F800B8            630 STHALM: LDI A.1(BGMTHM);PHI TI
           055A  F800A9            631         LDI A.0(EKGAL2);PLO TO
           055D  F85BB9            632         LDI A.1(EKGAL2);PHI TO
        F  0560  09FA183200        633         LDN TO;ANI #18;BZ CKBALM
        F  0565  F8103A00          634         XRI #10;BNZ CKBALM ..VT?
        FF 0569  F800A8C00000      635         LDI A.0(VTTHM);PLO TI;LBR STHOUT
           056F                    636   ..
           056F  D3                637 CKBALM: SEP MPC
        F  0570  09FA203200        638         LDN TO;ANI #20;BZ CKPVAL
        FF 0575  F800A8C00000      639         LDI A.0(BGMTHM);PLO TI;LBR STHOUT
           057B                    640   ..
           057B  D3                641 CKPVAL: SEP MPC
```

```
0630                        720 ..*********ENTRY FOR PRNTQT**********
0630  3E2F                  721 PRNTQT: BN3 PRNTQT-1      ..BUSY?
0632  F0FBFF322C            722         LDX;XRI #FF;BZ PRNTRT ..DONE?
0637  63302F                723         OUT PRINTR;BR PRNTQT-1
063A                        724 ..................................
063A                        725 ..SUBROUTINE BINARY TO ASCII(OR BCD)
063A                        726 ..ENTER WITH BINARY# IN SUM
063A                        727 ..OUTPUT: 4 BYTE PUSH DOWN STACK:
063A                        728 ..   THOUS;HUNDR;TENS;UNITS
063A                        729 ..CALLING SEQUENCE:
063A                        730 ..       LDI A.0(BINSCI);PLO CALL
063A                        731 ..       SEP CALL,A.0(THOUS)
063A  D3                    732         SEP MPC ..RETURN
063B                        733 ..*******ENTRY FOR BINSCII*********
063B  43A6                  734 BINSCI: LDA MPC;PLO DST
063D  87FFE8A7              735 THOUSL: GLO SUM;SMI A.0(K1000);PLO SUM
0641  977F03B7              736         GHI SUM;SMBI A.1(K1000);PHI SUM
F 0645  3800                737         BM DOHUND  ..OVERFLOW
0647  05FC0156              738         LDN DST;ADI 1;STR DST ..ANOTHER THOUS.
064B  FB3A3A3D              739         XRI #3A;BNZ THOUSL ..OVERFLOW?
064F  F82A56                740         LDI T'*';STR DST ..MARK OVERFLOW
F 0652  163000               741         INC DST;BR HUNDOF ..MARK!!!
0655                        742 ..
0655  A7FCE8A7              743 DOHUND: GLO SUM;ADI A.0((1000);PLO SUM
0659  977C03B7              744         GHI SUM;ADCI A.1(K1000);PHI SUM
065D  16                    745         INC DST ..DST=A.0(HUNDR)
065E  87FF64A7              746 HUNDRL: GLO SUM;SMI 100;PLO SUM
0662  977F00B7              747         GHI SUM;SMBI 0;PHI SUM
F 0666  3800                748         BM DOTENS
0668  05FC0156              749         LDN DST;ADI 1;STR DST
066C  FB3A3A5E              750         XRI #3A;BNZ HUNDRL ..OVERFLOW?
0670  F82A56                751 HUNDOF: LDI T'*';STR DST
F 0673  163000               752         INC DST;BR TENSOF ..MARK!!
0676                        753 ..
0676  87FC64A7              754 DOTENS: GLO SUM;ADI 100;PLO SUM
067A  16                    755         INC DST ..DST=A.0(TENS)
067B  87FF0AA7              756 TENSL:  GLO SUM;SMI 10;PLO SUM
F 067F  3800                757         BM DOUNIT
0681  06FC0156              758         LDN DST;ADI 1;STR DST
0685  FB3A3A7B              759         XRI #3A;BNZ TENSL
0689  F82A56                760 TENSOF: LDI T'*';STR DST
068C  1656303A              761         INC DST;STR DST;BR BINSCI-1
0690  16E5                  762 DOUNIT: INC DST;SEX DST
0692  87FC0AF456            763         GLO SUM;ADI 10;ADD;STR DST
0697  303A                  764         BR BINSCI-1 ..DONE!
0699                        765 ..................................
0699                        766 ..SUBROUTINE DIVIDE
0699                        767 ..NO DIVIDE BY 0;NO REMAINDER
0699                        768 ..DIVISOR & QUOTIENT = 8BITS
0699                        769 ..ENTER WITH 16BIT DIVIDEND IN SUM
0699                        770 ..CALL.SEQ. : LDI A.0(DIVIDE);PLO CALL
0699                        771 ..       SEP CALL,A.0(DIVISR),A.0(QUOTNT)
0699  D3                    772         SEP MPC ..RETURN
069A                        773 ..*********ENTRY FOR DIVIDE*********
069A  43A543A6              774 DIVIDE: LDA MPC;PLO SRC;LDA MPC;PLO DST
069E  F80056E5              775         LDI 0;STR DST;SEX SRC
06A2  053299                776         LDN SRC;BZ DIVIDE-1
06A5  87F7A7                777 DIVLP:  GLO SUM;SM;PLO SUM
06A8  977F00B7              778         GHI SUM;SMBI 0;PHI SUM
06AC  3B99                  779         BM DIVIDE-1 ..DONE!
06AE  05FC0156              780         LDN DST;ADI 1;STR DST
06B2  30A5                  781         BR DIVLP ..CONTINUE
06B4                        782 ..................................
06B4                        783 ..SUBROUTINE TURN CASSETTE ON
06B4                        784 ..CALLING SEQ.:
06B4                        785 ..       LDI A.0(TCASON);PLO CALL;SEP CALL
06B4  D3                    786         SEP MPC ..RETURN
06B5                        787 ..   *****ENTRY FOR TCASON*****
06B5  F813A6E6              788 TCASON: LDI A.0(TIME+1);PLO DST;SEX DST
06B9  F8007373              789         LDI 0;STXD;STXD
06BD  F8F9A6                790         LDI A.0(BKMODE);PLO DST
06C0  F80056                791         LDI 0;STR DST ..BKMODE<-0
06C3                        792 ..INIT CCT,STO:
06C3  F900AA                793         LDI A.0(TAPBUF);PLO STO
06C6  F95BBA                794         LDI A.1(TAPBUF);PHI STO
06C9  F94AAC                795         LDI A.0(DATACT);PLO CCT
06CC  F800BC                796         LDI A.1(DATACT);PHI CCT
```

```
F   057C  09FA403200       642            LDN TO;ANI #40;BZ CKOBAL
FF  0581  F800A8C00000     643            LDI A.0(VEBTHM);PLO TI;LBR STHOUT
    0587                   644   ..
    0587  D3               645   CKOBAL:  SEP MPC
F   0588  49FA803200       646            LDA TO;ANI #80;BZ CKSVTA
FF  058D  F800A8C00000     647            LDI A.0(DBTHM);PLO TI;LBR STHOUT
    0593                   648   ..
    0593  D3               649   CKSVTA:  SEP MPC  ..TO = A(EKGAL1)
F   0594  09FA10C20000     650            LDN TO;ANI #10;LBZ CKSVBA
FF  059A  F800A8C00000     651            LDI A.0(SVTTHM);PLO TI;LBR STHOUT
    05A0                   652   ..
    05A0  D3               653   CKSVBA:  SEP MPC
    05A1  09FA4032A0       654            LDN TO;ANI #40;BZ CKSVBA
F   05A6  F800A8           655            LDI A.0(SVBTHM);PLO TI
    05A9                   656   ..$$$$$$$$$$$$$$$$$$$$$$$$$$$$$$$$$$$$$$..
    05A9                   657   ..STRIP CHART THERMAL PRINTHEAD OUTPUT
    05A9                   658   ..ROUTINE: ACCEPTS ASCII INPUT #20 TO #5A
    05A9                   659   ..POINTED TO BY TI,WITH TRAILING HALT CHR.
    05A9  D3               660   STHOUT:  SEP MPC
    05AA  08FBFF32A9       661            LDN TI;XRI HALT;BZ STHOUT ..DONE?
    05AF  08FEFEA9         662            LDN TI;SHL;SHL;PLO TO
    05B3  F8007EB9         663            LDI 0;SHLC;PHI TO ..*4
    05B7  89E8F4A9         664            GLO TO;SEX TI;ADD;PLO TO
    05BB  997C00B9         665            GHI TO;ADCI 0;PHI TO ..*5
    05BF                   666   ..SUBTRACT #20*5 :
    05BF  D3               667            SEP MPC
    05C0  89FFA0A9         668            GLO TO;SMI #A0;PLO TO
    05C4  997F00B9         669            GHI TO;SMBI 0;PHI TO
    05C8                   670   ..ADD BASE ADDRESS TO INDEX:
F   05C9  89FC00A9         671            GLO TO;ADI A.0(THRTAB);PLO TO
F   05CC  997C00B9         672            GHI TO;ADCI A.1(THRTAB);PHI TO
    05D0                   673   ..OUTPUT 5 X 7 DOT MATRIX:
    05D0  D3               674            SEP MPC
    05D1  E964D3D3         675   THOT1:   SEX TO;OUT STRPCH;SEP MPC;SEP MPC
    05D5  EE6401D3         676   TCOOL1:  SEX TPC;OUT STRPCH,#01;SEP MPC
    05D9  E964D3D3         677   THOT2:   SEX TO;OUT STRPCH;SEP MPC;SEP MPC
    05DD  EE6401D3         678   TCOOL2:  SEX TPC;OUT STRPCH,#01;SEP MPC
    05E1  E964D3D3         679   THOT3:   SEX TO;OUT STRPCH;SEP MPC;SEP MPC
    05E5  EE6401D3         680   TCOOL3:  SEX TPC;OUT STRPCH,#01;SEP MPC
    05E9  E964D3D3         681   THOT4:   SEX TO;OUT STRPCH;SEP MPC;SEP MPC
    05ED  EE6401D3         682   TCOOL4:  SEX TPC;OUT STRPCH,#01;SEP MPC
    05F1  E964D3D3         683   THOT5:   SEX TO;OUT STRPCH;SEP MPC;SEP MPC
    05F5  EE6401D3         684   TCOOL5:  SEX TPC;OUT STRPCH,#01;SEP MPC
    05F9  1830A9           685            INC TI;BR STHOUT
    05FC                   686   ..++++++++++++++++++++++++++++++++..
    0600                   687            PAGE
    0600                   688   ..SUBROUTINES:
    0600                   689   ..SUBROUTINE TIMER  CALLING SEQUENCE:
    0600                   690   ..       LDI A.0(TIMER);PLO CALL;SEP CALL
    0600  D3               691            SEP MPC  ..RETURN
    0601  F812A6           692   TIMER:   LDI A.0(TIME);PLO DST
F   0604  06FA0132003D00   693            LDN DST;ANI #01;BZ TMOCK;BN2 TIMER-1
    060B  06FC0156         694   TMADD1:  LDN DST;ADI 1;STR DST
    060F  16067C0056       695            INC DST;LDN DST;ADCI 0;STR DST ..TIME.1
    0614  3000             696            BR TIMER-1
    0616  3500300B         697   TMOCK:   B2 TIMER-1;BR TMADD1
    061A                   698   ..........................
    061A                   699   ..SUBROUTINE DELAY  CALLING SEQUENCE:
    061A                   700   ..       LDI A.0(DELAY);PLO CALL
    061A                   701   ..       SEP CALL,#MS.*4
    061A  D3               702            SEP MPC  ..RETURN
    061B  43B7             703   DELAY:   LDA MPC;PHI SUM
    061D  43A7             704            LDA MPC;PLO SUM
    061F                   705   ..DIVIDE DOWN BY 4MS.:
    061F  3D1F             706   WTFR1:   BN2 WTFR1
    0621  3521             707   WTFR0:   B2 WTFR0
    0623  2787 3A1F        708            DEC SUM;GLO SUM;BNZ WTFR1
    0627  973A1F           709            GHI SUM;BNZ WTFR1
    062A  301A             710            BR DELAY-1
    062C                   711   ..........................
    062C                   712   ..SUBROUTINE PRINT OR QUIT
    062C                   713   ..CALLING SEQ. :
    062C                   714   ..       LDI A.0(PRNTQT);PLO CALL
    062C                   715   ..       SEP CALL;LBR NOTDNE
    062C                   716   ..ON ENTRY X MUST POINT TO CHAR. STRING
    062C                   717   ..ROUTINE FALLS THROUGH ON TERMINATOR #FF
    062C  131313           718   PRNTRT:  INC MPC;INC MPC;INC MPC
    062F  D3               719            SEP MPC
```

```
          06CF                  797 ..ENABLE INTERRUPTS:
          06CF  E47064           798        SEX CALL;RET, #54
          0602                  799 ..READ CASSETTE:
          0602  F81046           800        LDI A.0(CASCTL);PLO DST
          0605  F8025665         801        LDI READ;STR DST;OUT CASOUT
          0609  3084             802        BR TCASON-1
          060B                  803 •••••••••••••••••••••••••••••••
          060B                  804 ..SUBROUTINE LATCH MODE(ETC)
          060B                  805 ..CALLING SEQ.:
          060B                  806 ..       LDI A.0(LTCMOD);PLO CALL;SEP CALL
          060B  03               807        SEP MPC ..RETURN
          060C                  808 ..       *****ENTRY FOR LTCMOD*****
          060C  F81146E6         809 LTCMOD: LDI A.0(INPWRD);PLO DST;SEX DST
F         06E0  6CFA01CA0000     810         INP INPORT;ANI #01;LBNZ EXITCS
          06E5                  811 ..RECIEVED MODE?
          06E5  F8FAA5           812        LDI A.0(MODE);PLO SRC
          06E9  05C2060B         813        LDN SRC;LBZ LTCMOD-1
          06ED                  814 ..YES;LATCH MODE:
          06ED  2555             815        DEC SRC;STR SRC ..BKMODE<- MODE
          06EF  15F80055         816        INC SRC;LDI 0;STR SRC ..MODE<- 0
          06F3  2505             817        DEC SRC;LDN SRC
          06F5                  818 ..IF MODE =#84 OR #92 ;INCREASE CCT:
F         06F5  FB843200         819        XRI #84;BZ INCCT
          06F9  05F8923A0B       820        LDN SRC;XRI #92;BNZ LTCMOD-1
          06FD                  821 ..
          06FE  E47144           822 INCCT:  SEX CALL;DIS,#44
          0701  8CFC2FAC         823        GLO CCT;ADI EKGCT;PLO CCT
          0705  7064             824        RET,#64
          0707  F801BCC0060B     825        LDI 1;PHI CCT;LBR LTCMOD-1
          070D                  826 ..
          070D  F8BBA3           827 EXITCS: LDI A.0(NOCASS);PLO MPC
          0710  F801B3           828        LDI A.1(NOCASS);PHI MPC
          0713  C0060B           829        LBR LTCMOD-1
          0716                  830 •••••••••••••••••••••••••••••••
          0716                  831 ..
          0716                  832 ..SYNCHRONIZE ROUTINE:
          0716  D1               833 SYNCTP: SEP IPC
          0717  F0FBFE3A16       834 SYNCRT: LDX;XRI #FE;BNZ *-4
          071C  01010101         835        SEP IPC;SEP IPC;SEP IPC;SEP IPC
          0720  01010101         836        SEP IPC;SEP IPC;SEP IPC;SEP IPC
          0724  F0FBFC3A16       837        LDX;XRI #FC;BNZ SYNCTP
          0729  01010101         838        SEP IPC;SEP IPC;SEP IPC;SEP IPC
          072D  01010101         839        SEP IPC;SEP IPC;SEP IPC;SEP IPC
          0731  F0FB023A16       840        LDX;XRI #02;BNZ SYNCTP
          0736  01010101         841        SEP IPC;SEP IPC;SEP IPC;SEP IPC
          073A  01010101         842        SEP IPC;SEP IPC;SEP IPC;SEP IPC
          073E  F0FB033A16       843        LDX;XRI #03;BNZ SYNCTP
          0743  01010101         844        SEP IPC;SEP IPC;SEP IPC;SEP IPC
          0747  01010101         845        SEP IPC;SEP IPC;SEP IPC;SEP IPC
          074B  F0FB593A16       846        LDX;XRI #59;BNZ SYNCTP
          0750  01010101         847        SEP IPC;SEP IPC;SEP IPC;SEP IPC
          0754  01010101         848        SEP IPC;SEP IPC;SEP IPC;SEP IPC
          0758  80F73216         849        GLO HOLD;SM;BZ SYNCTP ..REPEAT RECORD?
          075C  F0B0             850        LDX;PHI HOLD ..HOLD NEW RECORD #
          075E  01010101         851        SEP IPC;SEP IPC;SEP IPC;SEP IPC
          0762  01010101         852        SEP IPC;SEP IPC;SEP IPC;SEP IPC
          0766  F0225260         853        LDX;DEC STK;STR STK;IRX ..LOAD MODE
          076A                  854 ..WAIT FOR NEW CHARACTER:
          076A  01010101         855 NEWCHR: SEP IPC;SEP IPC;SEP IPC;SEP IPC
          076E  010101           856        SEP IPC;SEP IPC;SEP IPC
F         0771  8C3A00           857        GLO CCT;BNZ STRSTO
F         0774  9C3A00           858        GHI CCT;BNZ STRSTO
          0777                  859 ..CCT=0! STOP CASSETTE,DISABLE INT.
          0777  F810AD           860        LDI A.0(CASCTL);PLO ADR
          077A  F8150D           861        LDI STOP;STR ADR
          077D  ED65             862        SEX ADR;OUT CASOUT
          077F                  863 ..READY RETURN DISABLEING INTERRUPTS:
          077F  E2               864        SEX STK
F         0780  F80B1            865        LDI A.1(DIE);PHI IPC
F         0783  F80A13016        866        LDI A.0(DIE);PLO IPC;BR SYNCTP
          0788                  867 ..
          0788                  868 ..CHR==>BUFFER(STO)
          0788  D1               869 STRSTO: SEP IPC
          0789  F05A             870        LDX;STR STO
          078B  D1               871        SEP IPC
          078C  1A2C306B         872        INC STO;DEC CCT;BR NEWCHR+1
          0790                  873 ..
          0790                  874 ..
```

```
                            875 ..EKG TREND REPORTER INTERRUPT ROUTINE:
0790                        876 ..
0790                        877 ..DISABLE INTERRUPT EXIT:
0790                        878 DIE:    IRX;LDXA;SHLC ..DF
0790   60727E
F 0793 72713000              879         LDXA;DIS;BR INTRPT
0797                        880 ..
0797   60727E                881 QUIT:   IRX;LDXA;SHLC ..DF
079A   7270                  882         LDXA;RET ..0
079C                        883 ..******INTERRUPT ENTRY********
079C   2278                  884 INTRPT: DEC STK;SAV
079E   22737673              885         DEC STK;STXD;S+RC;STXD ..0,DF
07A2                        886 ..
07A2                        887 ..
07A2                        888 ..BIT SHIFTER ROUT.: (STK=A(C+R))
07A2   F0F634A8              889 SHFTBT: LDX;SHR;B1 ..+ ..DATA=1?
07A6   F98052                890         ORI #80;STR STK
07A9   DF                    891         SEP SPC ..NO(CALL SYNC ROUT.)
07AA   3097                  892         BR QUIT
07AC                        893 ..............................
07AC                        894 ..THERMAL PRINTER CONERSION TABLE:
07AC                        895 THRTAB=*
07AC   0101010101            896 SPACE:  ,X'0101010101'
07B1   01019F0101            897 EXCL:   ,X'01019F0101' ..!
07DE                        898         ORG THRTAB+#32
07DE   2911701129            899 STAR:   ,X'2911701129' ..*
07F2                        900         ORG STAR+20
07F2   01C1C10101            901 THRMDT: ,X'01C1C10101' ..(.)
07FC                        902         ORG THRTAB+#50
07FC   7DA3938B7D            903 ZERO:   ,X'7DA3938B7D'
0801   0185FF8101            904 ONE:    ,X'0185FF8101'
0806   85C3A3938D            905 TWO:    ,X'85C3A3938D'
080B   43838B97C3            906 THREE:  ,X'43838B97C3'
0810   312925FF21            907 FOUR:   ,X'312925FF21'
0815   4F8B8B8B73            908 FIVE:   ,X'4F8B8B8B73'
081A   7995939361            909 SIX:    ,X'7995939361'
081F   03E3130807            910 SEVEN:  ,X'03E3130807'
0824   6D9393936D            911 EIGHT:  ,X'6D9393936D'
0829   0D9393533D            912 NINE:   ,X'0D9393533D'
082E   01C7C70101            913 COLON:  ,X'01C7C70101'
0833   0181670101            914 SEMCOL: ,X'0181670101'
0838   1129858301            915 LESTHN: ,X'1129858301'
083D   2929292929            916 EQUALS: ,X'2929292929'
0842   0183852911            917 GTRTHN: ,X'0183852911'
0847   0503A3130D            918 QMRK:   ,X'0503A3130D'
0855                        919         ORG THRTAB+#AA
0855   FF9393936D            920 B:      ,X'FF9393936D'  ..B
085B   7D83838345            921 C:      ,X'7D83838345'  ..C
0860   FF83834539            922 D:      ,X'FF83834539'  ..D
0865   FF93939383            923 E:      ,X'FF93939383'  ..E
086A   0101010101            924 F:      ,X'0101010101'
086F   7D8383393F3           925 G:      ,X'7D8383393F3' ..G
0874   0101010101            926 H:      ,X'0101010101'
0879   0183FF8301            927 I:      ,X'0183FF8301'  ..I
088D                        928         ORG THRTAB+#E1
088D   FF051905FF            929 M:      ,X'FF051905FF'  ..M
0892   FF091121FF            930 N:      ,X'FF091121FF'  ..N
08A3                        931         ORG THRTAB+#FF
08A3   8393939363            932 S:      ,X'8393939363'  ..S
08B0   0303FF0303            933 T:      ,X'0303FF0303'  ..T
08B5   FFFFFFFFFF            934 U:      ,X'FFFFFFFFFF'
08BA   3F4181413F            935 V:      ,X'3F4181413F'  ..V
08C9                        936         ORG V+15
08C9   0F11E1110F            937 Y:      ,X'0F11E1110F'  ..Y
08CE                        938 ..............................
08CE   5554FF                939 VTTHM:  ,T'VT',HALT
08D1   42494749454D494E59    940 BGMTHM: ,T'BIGEMINY',HALT
08DA   564542FF              941 VEBTHM: ,T'VE3',HALT
08DE   442E422EFF            942 DBTHM:  ,T'D',DOT,T'B',DOT,HALT
08E3   535554FF              943 SVTTHM: ,T'SVT',HALT
08E7   53564542FF            944 SVBTHM: ,T'SVEB',HALT
08EC   3FFF                  945 QMRKTH: ,T'?',HALT
08EE                        946 ..............................
08EE   30303A3030            947 THRMSK: ,T'00:00'
08F3   FF                    948         ,HALT
08F4                        949 ..............................
08F4                        950 PNTMSK=*
08F4   10                    951 ,GS             ..80 COLUMNS:
```

```
08F5 30303A3030        952 ,T'00:30'    ..TIME
08FA 202020            953 ,SP,SP,SP
08FD 30303030          954 ,T'0000'     ..SVEB COUNT
0901 2020              955 ,SP,SP
0903 303030            956 ,T'000'      ..SVT COUNT
0906 20202020          957 ,SP,SP,SP,SP
090A 30303030          958 ,T'0000'     ..VEB(PVC) COUNT
090E 20                959 ,SP
090F 20                960 ,SP          ..BIGEMINI CODE(B)
0910 202020            961 ,SP,SP,SP
0913 303030            962 ,T'000'      ..VT COUNT
0916 2020              963 ,SP,SP
0918 303030            964 ,T'000'      ..COUPLET COUNT
091B 202020            965 ,SP,SP,SP
091E 3030              966 ,T'00'       ..D.B.COUNT
0920 202020            967 ,SP,SP,SP
0923 20                968 ,SP          ..STABILITY CODE
0924 20                969 ,SP
0925 20                970 ,SP          ..ARTIFACTS CODE
0926 20202020202020    971 ,SP,SP,SP,SP,SP,SP,SP
092D 303030            972 ,T'000'      ..SVEB/MIN
0930 2020              973 ,SP,SP
0932 303030            974 ,T'000'      ..VEB/MIN
0935 202020            975 ,SP,SP,SP
0938 303030            976 ,T'000'      ..H.R.
093B 2020              977 ,SP,SP
093D 303030            978 ,T'000'      ..L.R.
0940 2020              979 ,SP,SP
0942 303030            980 ,T'000'      ..AVG RATE
0945 0AFF              981 ,LF,HALT
0947                   982 ..
0947                   983 ..TREND REPORT HEADING:
0947 1F0E0A0A          984 MEDMSG: ,US,SO,LF,LF
094B 4D4544494341L1E   985 ,T'MEDICAL',RS,SP,US
0955 434F4E4345505453  986 ,T'CONCEPTS',RS,SP,US
0960 494E432E0A1E      987 ,T'INC.',LF,RS
0966 4D4F44454C23203  1 988 ,T'MODEL#',SP,T'1800'
0971 2053455249414C23  989 ,SP,T'SERIAL#',SP,T'NP1'
097D 0A0A0A            990 ,LF,LF,LF
0980 5041544945454520  991 ,T'PATIENT',SP,T'NAME:',SP
098E 1D                992 ,GS      ..80 COLUMNS
098F 2E2E2E2E2E2E2E2E  993 ,TD,TD,TD,TD,TD
0999 2E2E2E2E2E2E2E2E  994 ,TD,TD,TD,TD,TD
09A3 2E2E2E2E2E2E2E2E  995 ,TD,TD,TD,TD,TD
09AD 2E2E2E2E2E2E2E2E  996 ,TD,TD,TD,TD,TD
09B7 0A0A              997 ,LF,LF
09B9 1E                998 ,RS      ..40 COLUMNS:
09BA 5041544945454520  999 ,T'PATIENT',SP,T'NUMBER:',SP
09CA 1D               1000 ,GS      ..80 COLUMNS:
09CB 2E2E2E2E2E2E2E2E 1001 ,TD,TD,TD,TD,TD
09D5 2E2E2E2E2E2E2E2E 1002 ,TD,TD,TD,TD,TD
09DF 2E2E2E2E2E2E2E2E 1003 ,TD,TD,TD,TD,TD
09E9 2E2E2E2E2E2E2E2E 1004 ,TD,TD,TD,TD,TD
09F3 0A0A             1005 ,LF,LF
09F5 1E               1006 ,RS      ..40 COLUMNS:
09F6 454B472044415445 1007 ,T'EKG',SP,T'DATE:',SP
0A00 1D               1008 ,GS      ..80 COLUMNS:
0A01 2E2E2E2E2E2E2E2E 1009 ,TD,TD,TD,TD,TD
0A0B 2E2E2E2E2E2E2E2E 1010 ,TD,TD,TD,TD,TD
0A15 2E2E2E2E2E2E2E2E 1011 ,TD,TD,TD,TD,TD
0A1F 2E2E2E2E2E2E2E2E 1012 ,TD,TD,TD,TD,TD
0A29 0A0A0A           1013 ,LF,LF,LF
0A2C 1E               1014 ,RS      ..40 COLUMNS:
0A2D 454B472054524E   1015 ,T'EKG',SP,T'TREND',SP,T'REPORT:'
0A3E 0A0A0A           1016 ,LF,LF,LF
0A41                  1017 ..
0A41                  1018 .. COUNTS(BEATS/15 MIN)  RATES(B.P.M.)
0A41 1E202020         1019 ,RS,SP,SP,SP
0A45 434F554E5453     1020 ,T'COUNTS'
0A4B 20201D           1021 ,SP,SP,GS
0A4E 28424541545332F31 1022 ,T'(BEATS/15'
0A57 20               1023 ,SP
0A58 4D494E29         1024 ,T'MIN)'
0A5C 1E20202020       1025 ,RS,SP,SP,SP,SP
0A61 5241544553       1026 ,T'RATES'
0A66 201D             1027 ,SP,GS
0A68 28424541545332F4D 1028 ,T'(BEATS/MIN)'
0A73 0A1D             1029 ,LF,GS
```

```
0A75                        1030  ..COLUMN IDENTIFICATION:
0A75 54494D45               1031  ,T'TIME'
0A79 20202020               1032  ,SP,SP,SP,SP
0A7D 53564542               1033  ,T'SVB'
0A81 2020                   1034  ,SP,SP
0A83 535654                 1035  ,T'SVT'
0A86 2020202020             1036  ,SP,SP,SP,SP,SP
0A8B 564542                 1037  ,T'VEB'
0A8E 20                     1038  ,SP
0A8F 42                     1039  ,T'B'
0A90 20202020               1040  ,SP,SP,SP,SP
0A94 5654                   1041  ,T'VT'
0A96 20                     1042  ,SP
0A97 2843504C29             1043  ,T'(CPL)'
0A9C 2020                   1044  ,SP,SP
0A9E 4442                   1045  ,T'DB'
0AA0 202020                 1046  ,SP,SP,SP
0AA3 532041                 1047  ,T'S',SP,T'A'
0AA6 202020202020           1048  ,SP,SP,SP,SP,SP,SP
0AAC 53564542               1049  ,T'SVB'
0AB0 2020                   1050  ,SP,SP
0AB2 564542                 1051  ,T'VEB'
0AB5 20202020               1052  ,SP,SP,SP,SP
0AB9 4852                   1053  ,T'HR'
0ABB 202020                 1054  ,SP,SP,SP
0ABE 4C52                   1055  ,T'LR'
0AC0 2020                   1056  ,SP,SP
0AC2 415647                 1057  ,T'AVG'
0AC5 0AFF                   1058  ,LF,HALT
0AC7                        1059  ..
0AC7                        1060  ..OUT OF SEQUENCE:
0AC7 1F0E                   1061  EOSMSG: ,US,SO ..20 CHAR
0AC9 202020                 1062  ,SP,SP,SP
0ACC 1E                     1063  ,RS       ..40 COLUMNS
0ACD 2A2A2A                 1064  ,T'***'
0AD0 5245434F5244           1065  ,T'RECORD'
0AD6 20                     1066  ,SP
0AD7 4F5554                 1067  ,T'OUT'
0ADA 20                     1068  ,SP
0ADB 4F46                   1069  ,T'OF'
0ADD 20                     1070  ,SP
0ADE 534551554E4345         1071  ,T'SEQUNCE'
0AE5 2A2A2A                 1072  ,T'***'
0AE8 0AFF                   1073  ,LF,HALT
0AEA                        1074  ..
0AEA                        1075  ..SWITCH LEADS MESSAGE:
0AEA 1F0E                   1076  SWLMSG: ,US,SO
0AEC 20202020               1077  ,SP,SP,SP,SP
0AF0 1E                     1078  ,RS ..40 COLUMNS:
0AF1 2A2A2A                 1079  ,T'***'
0AF4 50524F4345535353       1080  ,T'PROCESS'
0AFB 20                     1081  ,SP
0AFC 4F54484552             1082  ,T'OTHER'
0B01 20                     1083  ,SP
0B02 4C454144               1084  ,T'LEAD'
0B06 2A2A2A                 1085  ,T'***'
0B09 0AFF                   1086  ,LF,HALT
0B0B                        1087  ..
0B0B                        1088  ..END OF REPORT MESSAGE:
0B0B 1E0E070A               1089  EOTMSG: ,RS,SO,BEL,LF
0B0F 20202020202020         1090  ,SP,SP,SP,SP,SP,SP,SP
0B16 2A2A2A2A2A2A454E       1091  ,T'******END'
0B1F 204F4620               1092  ,SP,T'OF',SP
0B23 5245504F52542A2A       1093  ,T'REPORT******'
0B2F 0A0A0A                 1094  ,LF,LF,LF
0B32                        1095  ..LEGEND(COLUMN HEADINGS LEFT TO RIGHT)
0B32 1E                     1096  ,RS       ..40 COLUMN
0B33 4C4547454E443A         1097  ,T'LEGEND:'
0B3A 20                     1098  ,SP
0B3B 1D                     1099  ,GS   ..80 COLUMNS:
```

```
0B3C 28434F4C554D4E   1100  ,T'(COLUMN'
0B43 20               1101  ,SP
0B44 48454144494E4753 1102  ,T'HEADINGS'
0B4C 20               1103  ,SP
0B4D 4C454654         1104  ,T'LEFT'
0B51 20               1105  ,SP
0B52 544F             1106  ,T'TO'
0B54 20               1107  ,SP
0B55 52494748542429   1108  ,T'RIGHT)'
0B5B 0A0A             1109  ,LF,LF
0B5D                  1110  ..TIME=START TIME OF 15 MINUTE INTERVAL
0B5D 1E               1111  ,RS    ..40 COLUMNS:
0B5E 54494D45         1112  ,T'TIME'
0B62 203D20           1113  ,SP,T'=',SP
0B65 1D               1114  ,GS    ..80 COLUMNS:
0B66 5354415254       1115  ,T'START'
0B6B 20               1116  ,SP
0B6C 54494D45         1117  ,T'TIME'
0B70 20               1118  ,SP
0B71 4F46             1119  ,T'OF'
0B73 20               1120  ,SP
0B74 3135             1121  ,T'15'
0B76 20               1122  ,SP
0B77 4D494E555445     1123  ,T'MINUTE'
0B7D 20               1124  ,SP
0B7E 494E544552564143 1125  ,T'INTERVAL'
0B85 0A               1126  ,LF
0B87                  1127  ..SVEB=SUPRA VENTRICULAR ECTOPIC BEATS/15 MINUTE
0B87 1E               1128  ,RS    ..40 COLUMNS:
0B88 53564542         1129  ,T'SVEB'
0B8C 203D20           1130  ,SP,T'=',SP
0B8F 1D               1131  ,GS    ..80 COLUMNS:
0B90 5355D05241       1132  ,T'SUPRA'
0B95 56454E5452494355 1133  ,T'VENTRICULAR'
0BA0 20               1134  ,SP
0BA1 4543544F504943   1135  ,T'ECTOPIC'
0BA3 20               1136  ,SP
0BA9 42454154532F3135 1137  ,T'BEATS/15'
0BB1 20               1138  ,SP
0BB2 4D494E555445320  1139  ,T'MINUTES
0BBA 0A               1140  ,LF
0BB3                  1141  ..SVT=SUPRAVENTRICULAR TACHYCARDIA
0BB3                  1142  ..EPISODES/15 MINUTES
0BB3 1E               1143  ,RS    ..40 COLUMNS:
0BBC 535654           1144  ,T'SVT'
0BBF 203D20           1145  ,SP,T'=',SP
0BC2 1D               1146  ,GS    ..80 COLUMNS:
0BC3 5355D05241       1147  ,T'SUPRA'
0BC8 56454E5452494355 1148  ,T'VENTRICULAR'
0BD3 20               1149  ,SP
0BD4 54414348594341452 1150  ,T'TACHYCARDIA'
0BDF 20               1151  ,SP
0BE0 455049534F444553 1152  ,T'EPISODES/15'
0BEB 20               1153  ,SP
0BEC 4D494E555445553  1154  ,T'MINUTES'
0BF3 0A               1155  ,LF
0BF4                  1156  ..VEB=VENTRICULAR ECTOPIC BEATS/15 MINUTES
0BF4 1E               1157  ,RS    ..40 COLUMNS:
0BF5 564542           1158  ,T'VEB'
0BF8 203D20           1159  ,SP,T'=',SP
0BFB 1D               1160  ,GS    ..80 COLUMNS
0BFC 56454E5452494355 1161  ,T'VENTRICULAR'
0C07 20               1162  ,SP
0C08 4543544F504943   1163  ,T'ECTOPIC'
0C0F 20               1164  ,SP
0C10 42454154532F3135 1165  ,T'BEATS/15'
0C18 20               1166  ,SP
0C19 4D494E55544553   1167  ,T'MINUTES'
0C20 0A               1168  ,LF
0C21                  1169  ..B=(B) INDICATES OCCURRENCE OF BIGEMINY
0C21 1E               1170  ,RS    ..40 COLUMNS:
0C22 42               1171  ,T'B'
0C23 203D20           1172  ,SP,T'=',SP
0C26 1D               1173  ,GS ..80 COLUMNS:
0C27 284229           1174  ,T'(B)'
0C2A 20               1175  ,SP
0C2B 494E444943415445 1176  ,T'INDICATES'
0C34 20               1177  ,SP
```

```
0C35 4F4343555252414E   1178 ,T'OCCURRANCE'
0C3F 20                 1179 ,SP
0C40 4F46               1180 ,T'OF'
0C42 20                 1181 ,SP
0C43 424947454D494E59   1182 ,T'BIGEMINY'
0C4B 0A                 1183 ,LF
0C4C                    1184 ..VT=VENTRICULAR TACHYCARDIA EPISODES/15
0C4C                    1185 ..MINUTES
0C4C                    1186 ..        (COUNT INCLUDES COUPLETS)
0C4C 1E                 1187 ,RS
0C4D 5554               1188 ,T'VT'
0C4F 203D20             1189 ,SP,T'=',SP
0C52 1D                 1190 ,GS      ..80 COLUMNS:
0C53 55454E5452494355   1191 ,T'VENTRICULAR'
0C5E 20                 1192 ,SP
0C5F 54414348594341521A 1193 ,T'TACHYCARDIA'
0C6A 20                 1194 ,SP
0C6B 455049534F444553   1195 ,T'EPISODES/15'
0C76 20                 1196 ,SP
0C77 4D494E5554455320   1197 ,T'MINUTES'
0C7E 20                 1198 ,SP
0C7F 28434F554E54       1199 ,T'(COUNT'
0C85 20                 1200 ,SP
0C86 494E434C55444553   1201 ,T'INCLUDES'
0C8E 20                 1202 ,SP
0C8F 434F55504C455453   1203 ,T'COUPLETS)'
0C98 0A                 1204 ,LF
0C99                    1205 ..(CPL)=COUPLETS...PAIRED VEBS(SUBSET OF VT)
0C99 1E                 1206 ,RS     ..40 COLUMNS:
0C9A 2843504C29         1207 ,T'(CPL)'
0C9F 203D20             1208 ,SP,T'=',SP
0CA2 1D                 1209 ,GS
0CA3 434F55504C455453   1210 ,T'COUPLETS...'
0CAE 5041495245441A     1211 ,T'PAIRED'
0CB4 20                 1212 ,SP
0CB5 56454253           1213 ,T'VEBS'
0CB9 20                 1214 ,SP
0CBA 285355425345541A   1215 ,T'(SUBSET'
0CC1 20                 1216 ,SP
0CC2 4F46               1217 ,T'OF'
0CC4 20                 1218 ,SP
0CC5 565429             1219 ,T'VT)'
0CC8 0A                 1220 ,LF
0CC9                    1221 ..DB=DROPPED BEATS/15 MINUTES
0CC9 1E                 1222 ,RS     ..40 COLUMNS:
0CCA 4442               1223 ,T'DB'
0CCC 203D20             1224 ,SP,T'=',SP
0CCF 1D                 1225 ,GS     ..80 COLUMNS:
0CD0 44524F5050454421   1226 ,T'DROPPED'
0CD7 20                 1227 ,SP
0CD8 42454154532F3135   1228 ,T'BEATS/15'
0CE0 20                 1229 ,SP
0CE1 4D494E5554455320   1230 ,T'MINUTES'
0CE8 0A                 1231 ,LF
0CE9                    1232 ..S=STABILITY CODE(U) INDICATES SEVERAL
0CE9                    1233 ..R-R INTERVALS UNSTABLE BY > 10%
0CE9 1E                 1234 ,RS     ..40 COLUMNS:
0CEA 53                 1235 ,T'S'
0CEB 203D20             1236 ,SP,T'=',SP
0CEE 1D                 1237 ,GS     ..80 COLUMNS:
0CEF 53544142494C495954 1238 ,T'STABILITY'
0CF8 20                 1239 ,SP
0CF9 434F44453A         1240 ,T'CODE:'
0CFE 20                 1241 ,SP
0CFF 285529             1242 ,T'(U)'
0D02 20                 1243 ,SP
0D03 494E4449434154455  1244 ,T'INDICATES'
0D0C 20                 1245 ,SP
0D0D 5345564552414C     1246 ,T'SEVERAL'
0D14 20                 1247 ,SP
0D15 522D52             1248 ,T'R-R'
0D18 20                 1249 ,SP
0D19 494E544552564154C  1250 ,T'INTERVALS'
0D22 20                 1251 ,SP
0D23 554E535441424C45   1252 ,T'UNSTABLE'
0D2B 20                 1253 ,SP
0D2C 4259               1254 ,T'BY'
```

```
0D2E 20                    1255 ,SP
0D2F 3E20313025             1256 ,T'>',SP,T'10%'
0D34 0A                    1257 ,LF
0D35                        1258 ..A=ARTIFACTS(TIME DURATION OF RUDUCED SENSITIVI
0D35                        1259 ..OR NOT PROCESSING MODES)
0D35 1E                    1260 ,RS    ..40 COLUMNS:
0D36 41                    1261 ,T'A'
0D37 203D20                 1262 ,SP,T'=',SP
0D3A 1D                    1263 ,GS    ..80 COLUMNS:
0D3B 415254494641435354     1264 ,T'ARTIFACTS'
0D44 20                    1265 ,SP
0D45 2854494D45             1266 ,T'(TIME'
0D4A 20                    1267 ,SP
0D4B 4455524154494F4E       1268 ,T'DURATION'
0D53 20                    1269 ,SP
0D54 4F46                   1270 ,T'OF'
0D56 20                    1271 ,SP
0D57 5245444543454            1272 ,T'REDUCED'
0D5E 20                    1273 ,SP
0D5F 53454E5349544956       1274 ,T'SENSITIVITY'
0D6A 20                    1275 ,SP
0D6B 4F52                   1276 ,T'OR'
0D6D 20                    1277 ,SP
0D6E 4E4F54                 1278 ,T'NOT'
0D71 20                    1279 ,SP
0D72 50524F43455353349      1280 ,T'PROCESSING'
0D7C 20                    1281 ,SP
0D7D 4D4F44455329           1282 ,T'MODES)'
0D83 0A                    1283 ,LF
0D84                        1284 ..(H) (M) (L) ( ) INDICATE HIGH,MEDIUM,LOW,NO AR
0D84 2848292C284D292C       1285 ,T'(H),(M),(L),('
0D91 20                    1286 ,SP
0D92 29                    1287 ,T')'
0D93 20                    1288 ,SP
0D94 494E44494341544      1289 ,T'INDICATE'
0D9C 20                    1290 ,SP
0D9D 484947482C             1291 ,T'HIGH,'
0DA2 4D454449554D2C         1292 ,T'MEDIUM,'
0DA9 4C4F572C               1293 ,T'LOW,'
0DAD 4E4F                   1294 ,T'NO'
0DAF 20                    1295 ,SP
0DB0 415254494641435354     1296 ,T'ARTIFACTS'
0DB9 0A                    1297 ,LF
0DBA                        1298 ..SVEB=HIGHEST ONE MINUTE SVEB COUNT
0DBA 1E                    1299 ,RS    ..40 COLUMNS:
0DBB 53564542               1300 ,T'SVEB'
0DBF 203D20                 1301 ,SP,T'=',SP
0DC2 1D                    1302 ,GS    ..80 COLUMNS:
0DC3 4849474845535354       1303 ,T'HIGHEST'
0DCA 20                    1304 ,SP
0DCB 4F4E45                 1305 ,T'ONE'
0DCE 20                    1306 ,SP
0DCF 4D494E555445           1307 ,T'MINUTE'
0DD5 20                    1308 ,SP
0DD6 53564542               1309 ,T'SVEB'
0DDA 20                    1310 ,SP
0DDB 434F554E54             1311 ,T'COUNT'
0DE0 0A                    1312 ,LF
0DE1                        1313 ..VEB=HIGHEST ONE MINUTE VEB COUNT
0DE1 1E                    1314 ,RS    ..40 COLUMNS:
0DE2 564542                 1315 ,T'VEB'
0DE5 203D20                 1316 ,SP,T'=',SP
0DE8 1D                    1317 ,GS    ..80 COLUMNS:
0DE9 4849474845535354       1318 ,T'HIGHEST'
0DF0 20                    1319 ,SP
0DF1 4F4E45                 1320 ,T'ONE'
0DF4 20                    1321 ,SP
0DF5 4D494E555445           1322 ,T'MINUTE'
0DFB 20                    1323 ,SP
0DFC 564542                 1324 ,T'VEB'
0DFF 20                    1325 ,SP
0E00 434F554E54             1326 ,T'COUNT'
0E05 0A                    1327 ,LF
0E06                        1328 ..HR=HIGHEST RATE
0E06 1E                    1329 ,RS    ..40 COLUMNS
0E07 4852                   1330 ,T'HR'
0E09 203D20                 1331 ,SP,T'=',SP
```

```
OEOC  1D                    1332  ,GS   ..30 COLUMNS
OEOD  4849474845535 4        1333  ,T'HIGHEST'
OE14  20                    1334  ,SP
OE15  484541525 4            1335  ,T'HEART'
OE1A  20                    1336  ,SP
OE1B  52415445              1337  ,T'RATE'
OE1F  0A                    1338  ,LF
OE20                        1339  ..LR=LOWEST HEART RATE
OE20  1E                    1340  ,RS   ..40 COLUMNS
OE21  4C52                  1341  ,T'LR'
OE23  203D20                1342  ,SP,T'=',SP
OE26  1D                    1343  ,GS   ..80 COLUMNS:
OE27  4C4F57455354          1344  ,T'LOWEST'
OE2D  20                    1345  ,SP
OE2E  4845415254            1346  ,T'HEART'
OE33  20                    1347  ,SP
OE34  52415445              1348  ,T'RATE'
OE38  0A                    1349  ,LF
OE39                        1350  ..AVG=AVERAGE HEART RATE
OE39  1E                    1351  ,RS   ..40 COLUMNS:
OE3A  415647                1352  ,T'AVG'
OE3D  203D20                1353  ,SP,T'=',SP
OE40  1D                    1354  ,GS   ..80 COLUMNS
OE41  4156455241474 5        1355  ,T'AVERAGE'
OE48  20                    1356  ,SP
OE49  484541525 4            1357  ,T'HEART'
OE4E  20                    1358  ,SP
OE4F  52415445              1359  ,T'RATE'
OE53  0A0A0A0A0A0A0A0AFF    1360  ,LF,LF,LF,LF,LF,LF,LF,8FF
OE5B                        1361  ..
OE5B                        1362  ..NO DATA ON CASSETTE MESSAGE:
OE5B  1E0E070A              1363  ERRMSG:  ,RS,30,BEL,LF
OE5F  45525 24F523A204E      1364  ,T'ERROR:',SP,T'NO',SP
OE69  4441544412 04F4E20     1365  ,T'DATA',SP,T'ON',SP,T'THIS',SP
OE76  534944452 04F4620      1366  ,T'SIDE',SP,T'OF',SP,T'CASSETTE!'
OE87  070A070A070A070A      1367  ,BEL,LF,BEL,LF,BEL,LF,BEL,LF
OE8F  070A070A07 0AFF        1368  ,BEL,LF,BEL,LF,BEL,LF,8FF
OE95                        1369  ..
OE95                        1370  ..NO CASSETTE MESSAGE:
OE95  1E0E070A              1371  NCMSG:   ,RS,30,BEL,LF
OE9A  070A07 0A              1372  ,BEL,LF,BEL,LF
OE9E  504C45415 34520        1373  ,T'PLEASE',SP
OEA5  43484543 4B20          1374  ,T'CHECK',SP
OEA8  4341535345545445      1375  ,T'CASSETTE',SP
OEB4  070A070A070A          1376  ,BEL,LF,BEL,LF,BEL,LF
OEBA  070A070A070A          1377  ,BEL,LF,BEL,LF,BEL,LF
OEC0  070A070A070AFF        1378  ,BEL,LF,BEL,LF,BEL,LF,HALT
OEC7                        1379  ..............................
OEC7                        1380  END
```

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or the scope of the invention as defined in the appended claims.

What is claimed is:

1. An ambulatory cardiac monitoring system to event record and monitor ECG signals from a patient for a predetermined time interval on a recording medium, said recording medium being removed from said patient subsequent to said predetermined time interval for insert into scanner means for producing printed outputs of said events recorded on said recording medium wherein the improvement comprises:

recorder means to be coupled to said patient during said predetermined time interval, said recorder means being electrically coupled to said patient for (1) continuously monitoring said ECG signals of said patient during said predetermined time interval, and (2) entering a record signal on said recording medium responsive to prior ECG signals monitored from said patient during said predetermined time interval, said recorder means including analog pre-processor means having means for detecting a QRS signal wave complex of said monitored ECG signal for (1) normalization, (2) filtering, and (3) gain control of said monitored ECG signals to produce a plurality of analog pre-processor output signals.

2. The ambulatory cardiac monitoring system as recited in claim 1, where said recorder means includes:
microcomputer means being connected to said analog pre-processor means in a feedback circuit for producing said record signals responsive to said prior ECG signals inserted to said analog pre-processor means during said predetermined time interval, said analog pre-processor means being coupled to said microcomputer means in a feed forward circuit.

3. The ambulatory cardiac monitoring system as recited in claim 2 where said means for detecting a QRS signal wave complex of said ECG signal input from said patient excludes a P wave complex signal and a T wave complex signal of said ECG signal for inserting predetermined portions of said QRS signal wave complex into said microcomputer means.

4. The ambulatory cardiac monitoring system as recited in claim 3 where said QRS signal wave detection means includes automatic gain control means coupled to said patient ECG signal output for maintaining an automatic gain control output signal responsive to signal amplitudes input to said automatic gain control means, said automatic gain control output signal being inserted into said microcomputer means.

5. The ambulatory cardiac monitoring system as recited in claim 4 including differentiator means coupled to said automatic gain control means for differentiating said automatic gain control output signal, said differentiator means for producing a differentiated ECG output pulse signal being inserted into said microcomputer means, said differentiated ECG output pulse signal for determining initiation and termination of predetermined sections of said ECG signal.

6. The ambulatory cardiac monitoring system as recited in claim 5 where said differentiator means produced differentiated ECG output pulse signal is a biphase signal having a positive portion and a negative pulse portion.

7. The ambulatory cardiac monitoring system as recited in claim 5 where said QRS signal wave detection means includes:
   (a) first adaptive threshold detector means coupled to said differentiator means for producing (1) a high positive lobe pulse, and, (2) a low positive lobe pulse output; and,
   (b) second adaptive threshold detector means coupled to said differentiator means for producing (3) a high negative lobe pulse, and (4) a low negative lobe pulse output, said high positive lobe pulse, low positive lobe pulse, high negative lobe pulse, and low negative lobe pulse, said first and second adaptive threshold detector means being coupled to said microcomputer means for insertion of said pulses to said microcomputer means.

8. The ambulatory cardiac monitoring system as recited in claim 7 including long term negative lobe automatic gain control means coupled to said differentiator means for standardizing a negative pulse portion of said differentiated ECG output pulse signal, said standardized negative pulse for establishing a base line negative pulse portion of said differentiated ECG output pulse signal.

9. The ambulatory cardiac monitoring system as recited in claim 7 where said first and second adaptive threshold detector means includes predetermined threshold boundary level signals for elimination of a signal output responsive to said P wave complex and said T wave complex of said differentiated ECG signal.

10. The ambulatory cardiac monitoring system as recited in claim 5 including a diminished sensitivity circuit coupled to said differentiator means for adjusting said signal level of said differentiated ECG signal.

11. The ambulatory cardiac monitoring system as recited in claim 10 including a four pole Bessel filter circuit coupled to said diminished sensitivity circuit, said four pole Bessel filter having a value approximately 40.0 Hertz.

12. The ambulatory cardiac monitoring system as recited in claim 5 including frequency response control network means having an ECG signal inserted thereto and being coupled to said automatic gain control means for inputting predetermined frequency bounded signals to said automatic gain control means, said frequency response control network means having a frequency boundary approximately 0.5 Hertz to 0.05 Hertz.

13. The ambulatory cardiac monitoring system as recited in claim 12 including differential input amplifier means to be coupled on opposing ends to said patient for receiving said ECG signal and said frequency response control network means for insert of an amplified ECG signal into said frequency response control network means.

14. The ambulatory cardiac monitoring system as recited in claim 2 where said analog pre-processor means includes morphology detection means for producing a plurality of output signals response to prior ECG signal information from said patient during said predetermined time interval, said morphology detection means being feedback coupled to said microcomputer means.

15. The ambulatory cardiac monitoring system as recited in claim 14 where said morphology detection means includes:
   (a) automatic gain control means coupled to said patient ECG signal output for producing an analog output signal being amplitude gain controlled as a function of signal amplitudes input thereto; and,
   (b) analog to digital conversion means connected to said automatic gain control means at an input thereof for producing a digital automatic gain controlled ECG signal for insert into said microcomputer means.

16. The ambulatory cardiac monitoring system as recited in claim 15 including microcomputer delaying means for maintaining said digital automatic gain controlled ECG signal within said microcomputer means for a predetermined time interval.

17. The ambulatory cardiac monitoring system as recited in claim 16 where said morphology detection means includes high frequency variation detection means for producing (1) a high frequency increase signal and (2) a high frequency decrease signal responsive to spectral variations between one of said ECG signals and at least one preceding ECG signal during said monitoring predetermined time interval.

18. The ambulatory cardiac monitoring system as recited in claim 17 where said high frequency variation detection means is operable within an approximate 40.0 Hertz band pass.

19. The ambulatory cardiac monitoring system as recited in claim 17 where said high frequency variation detection means includes first morphological adaptive threshold means for producing said (1) high frequency increase signal, and (2) high frequency decrease signal, said first morphological adaptive threshold means being operable on said delayed automatic gain controlled signal from said microcomputer means.

20. The ambulatory cardiac monitoring system as recited in claim 19 where said high frequency variation detection means includes delayed digital to analog converter means coupled to said microcomputer means for producing an analog delayed automatic gain controlled signal.

21. The ambulatory cardiac monitoring system as recited in claim 20 where said high frequency variation detection means includes high frequency band pass filter means for filtering a frequency band pass approximating 40.0 Hertz of said analog delayed automatic gain controlled signal.

22. The ambulatory cardiac monitoring system as recited in claim 21 including first full wave rectifier means for rectifying said filtered signal from said high frequency band pass filter means, said first full wave rectifier means being coupled to said high frequency band pass filter means.

23. The ambulatory cardiac monitoring system as recited in claim 22 including a first gated integrator circuit coupled on opposing ends to said first full wave rectifier means for signal input therefrom and to said first morphological adaptive threshold detector means, said first gated integrator circuit being coupled to said microcomputer means for receiving an actuating signal during a predetermined time interval.

24. The ambulatory cardiac monitoring system as recited in claim 14 where said morphological detection means includes:
(a) automatic gain control means coupled to said patient ECG signal output for producing an analog output signal being substantially amplitude independent as a function of signal amplitudes input thereto; and,
(b) low frequency variation detection means for producing (1) a low frequency increase signal and (2) a low frequency decrease signal responsive to spectral variations above and below a predetermined set of signal threshold signal levels.

25. The ambulatory cardiac monitoring system as recited in claim 24 where said low frequency variation detection means is operable in an approximate frequency range between 2.0 to 30.0 Hertz band pass.

26. The ambulatory cardiac monitoring system as recited in claim 25 where said low frequency variation detection means includes second morphological adaptive threshold detector means being actuated during a predetermined time interval for producing said (1) low frequency increase signal, and, (2) low frequency decrease signal, said second morphological adaptive threshold means being operable on said automatic gain controlled signal from said automatic gain control means.

27. The ambulatory cardiac monitoring system as recited in claim 26 where said low frequency variation detection means includes low frequency band pass filter means coupled to said automatic gain control means for filtering a frequency band pass approximating 2.0 to 30.0 Hertz of said automatic gain control signal.

28. The ambulatory cardiac monitoring system as recited in claim 27 including second full wave rectifier means for rectifying said filtered signal from said low frequency band pass filter means, said second full wave rectifier means being coupled to said low frequency band pass filter means.

29. The ambulatory cardiac monitoring system as recited in claim 28 including a second gated integrator circuit coupled on opposing ends thereof to said second full wave rectifier means for signal input therefrom and to said second morphological adaptive threshold detector means, said second gated integrator circuit being coupled to said microcomputer means for receiving an actuating signal during a predetermined time interval.

30. The ambulatory cardiac monitoring system as recited in claim 14 where said morphology detection means includes:
(a) automatic gain control means coupled to said patient signal output for producing an analog output signal being substantially amplitude gain controlled as a function of signal amplitudes input thereto; and,
(b) analog to digital conversion means coupled to said automatic gain control means at an input thereof for producing a digital automatic gain controlled ECG signal for insert into said micro-computer means.

31. The ambulatory cardiac monitoring system as recited in claim 30 including microcomputer delaying means for storing said digital automatic gain controlled ECG signal within a memory means within said microcomputer means for a predetermined time interval.

32. The ambulatory cardiac monitoring system as recited in claim 31 where said morphology detection means includes QRS wave complex variation detection means for producing (1) a positive peak differential decrease signal and (2) a negative peak differential decrease signal responsive to a differentiated delayed automatic gain controlled signal from said micro-computer means.

33. The ambulatory cardiac monitoring system as recited in claim 32 where said QRS wave complex variation detection means includes:
(a) third morphological adaptive threshold means being actuated during a predetermined time interval for producing said positive peak differential signal; and,
(b) fourth morphological adaptive threshold means being actuated during said predetermined time interval for producing said negative peak differential signal, said positive peak differential signal and said negative peak differential signal being inserted into said microcomputer means.

34. The ambulatory cardiac monitoring means as recited in claim 33 where said QRS wave complex variation detection means includes delayed digital to analog converter means for producing an analog delayed automatic gain controlled signal.

35. The ambulatory cardiac monitoring means as recited in claim 34 where said QRS wave complex variation detection means includes second differentiator means for differentiating said analog delayed automatic gain controlled signal from said digital to analog converter means.

36. The ambulatory cardiac monitoring system as recited in claim 35 where said QRS wave complex variation detection means includes first gated peak detector circuit coupled on opposing ends thereof to said second differentiator means and said third morphological adaptive threshold detector means for charging to a predetermined voltage signal level of a particular QRS wave complex signal, said first gated peak detector circuit for discharging said voltage signal level to said third morphological adaptive threshold detector means responsive to a signal from said microcomputer means.

37. The ambulatory cardiac monitoring system as recited in claim 35 where said QRS wave complex variation detection means includes inverter means coupled to said second differentiator means for inverting said differentiated delayed automatic gain controlled signal emitted from said second differentiator means.

38. The ambulatory cardiac monitoring system as recited in claim 37 where said QRS wave complex variation detection means includes second gated peak detector circuit coupled on opposing ends to said inverter means and said fourth morphological adaptive threshold detector means for input of a signal thereto responsive to a signal introduced from said micro-computer means.

39. The ambulatory cardiac monitoring system as recited in claim 2 where said analog pre-processor means includes base line artifact detector means for sensing (1) an excursion of a base line signal external of predetermined boundary signal level, and (2) a rate of change of said base line signal external a predetermined boundary rate of change, said base line artifact detector means being coupled to said micro-computer means for insertion thereto of a base line signal.

40. The ambulatory cardiac monitoring system as recited in claim 39 where said base line artifact detector means includes automatic gain control means coupled to said patient ECG signal output for maintaining an automatic gain control output signal responsive to signal amplitude input to said automatic gain control means, said automatic gain control output signals providing a base line signal level for said patient ECG signal.

41. The ambulatory cardiac monitoring system as recited in claim 40 where said base line artifact detector means includes base line filter means coupled to said automatic gain control means for substantial removal of (1) a T wave signal component, (2) a QRS wave complex signal component, and (3) a P wave signal component of said ECG signal, said base line filter means outputting said base line signal.

42. The ambulatory cardiac monitoring system as recited in claim 41 where said base line filter means is a 2.0 Hertz low pass Bessel filter circuit.

43. The ambulatory cardiac monitoring system as recited in claim 41 where said base line artifact detector means includes:
 (a) base line positive threshold detector means coupled to said base line filter means for outputting a signal when said base line signal exceeds a predetermined positive threshold level; and,
 (b) base line negative threshold detector means coupled to said base line filter means for outputting a signal when said base line signal exceeds a predetermined negative threshold level.

44. The ambulatory cardiac monitoring system as recited in claim 41 where said base line artifact detector means includes base line differentiator means coupled to said base line filter means for outputting a differentiated base line signal for producing enhanced base line signal variations.

45. The ambulatory cardiac monitoring system as recited in claim 44 including base line rectification means coupled to said base line differentiator means for providing full wave rectification of said differentiated base line signal.

46. The ambulatory cardiac monitoring system as recited in claim 45 including:
 (a) baseline absolute low threshold detector means; and,
 (b) baseline absolute high threshold detector means coupled in parallel relation with said baseline absolute low threshold detector means to said baseline rectification means, each of said baseline low and high threshold detector means for outputting a baseline detect signal when said rectified differentiated baseline signal exceeds a predetermined low and high valve respectively.

47. The ambulatory cardiac monitoring system as recited in claim 46 where said base line artifact detector means includes dual rate integrator means coupled to said base line absolute low threshold detector means and said base line absolute high threshold detector means for producing an integrated output signal.

48. The ambulatory cardiac monitoring system as recited in claim 47 including integrated base line detector means coupled to said dual rate integrator means and said microcomputer means for outputting a signal to said microcomputer means responsive to said integrated output signal exceeding a predetermined signal level.

* * * * *